United States Patent
Anderson et al.

(10) Patent No.: US 10,328,207 B2
(45) Date of Patent: *Jun. 25, 2019

(54) ANTISEPTIC CAP

(71) Applicant: Excelsior Medical Corporation, San Clemente, CA (US)

(72) Inventors: William Anderson, Cary, IL (US); Mark Wilson, Rochester, NY (US); Gary Henniger, Belmar, NJ (US); Larry Colquitt, West Henrietta, NY (US); Christopher E. Gardner, Manalapan, NJ (US); Chirag Sanjay Walawalkar, Jackson, NJ (US)

(73) Assignee: Excelsior Medical Corporation, San Clemente, CA (US)

( * ) Notice: Subject to any disclaimer, the term of this patent is extended or adjusted under 35 U.S.C. 154(b) by 94 days.

This patent is subject to a terminal disclaimer.

(21) Appl. No.: 15/637,998

(22) Filed: Jun. 29, 2017

(65) Prior Publication Data

US 2017/0361023 A1 Dec. 21, 2017

Related U.S. Application Data

(63) Continuation of application No. 14/799,022, filed on Jul. 14, 2015, now Pat. No. 9,707,350, which is a
(Continued)

(51) Int. Cl.
*A61M 5/31* (2006.01)
*A61M 5/315* (2006.01)
(Continued)

(52) U.S. Cl.
CPC .......... *A61M 5/31511* (2013.01); *A61M 5/31* (2013.01); *A61M 25/04* (2013.01);
(Continued)

(58) Field of Classification Search
CPC .... A61M 5/31511; A61M 5/31; A61M 39/20; A61M 39/162; A61M 39/02;
(Continued)

(56) References Cited

U.S. PATENT DOCUMENTS

| 877,946 A | 2/1908 | Overton |
| 1,793,068 A | 2/1931 | Dickinson |

(Continued)

FOREIGN PATENT DOCUMENTS

| CA | 2 148 847 | 12/1995 |
| CA | 2 169 689 | 8/1996 |

(Continued)

OTHER PUBLICATIONS

Baxter Minicap: Photographs of the Baxter Minicap (Sep. 1, 1998) (4 pages).
(Continued)

*Primary Examiner* — Bradley J Osinski
(74) *Attorney, Agent, or Firm* — Knobbe Martens Olsen & Bear, LLP

(57) ABSTRACT

A syringe assembly including: (1) a syringe barrel defining a chamber; (2) a plunger mounted in the chamber and moveable with respect to the barrel; and (3) a cap holder assembly containing a cap and an absorbent material removably attached to the syringe.

16 Claims, 45 Drawing Sheets

Related U.S. Application Data continuation of application No. 13/547,650, filed on Jul. 12, 2012, now Pat. No. 9,259,535, which is a continuation-in-part of application No. 13/288,529, filed on Nov. 3, 2011, now Pat. No. 9,700,710, which is a continuation-in-part of application No. 11/821,190, filed on Jun. 22, 2007, now Pat. No. 8,167,847, and a continuation-in-part of application No. 12/214,526, filed on Jun. 19, 2008, now Pat. No. 9,707,348, which is a continuation-in-part of application No. 11/821,190.

(60) Provisional application No. 60/815,806, filed on Jun. 22, 2006.

(51) Int. Cl.
*A61M 25/04* (2006.01)
*A61M 39/16* (2006.01)
*A61M 39/02* (2006.01)
*A61M 39/20* (2006.01)
A61M 25/00 (2006.01)
A61M 5/00 (2006.01)
A61M 5/34 (2006.01)
A61M 39/10 (2006.01)

(52) U.S. Cl.
CPC ............ *A61M 39/02* (2013.01); *A61M 39/16* (2013.01); *A61M 39/162* (2013.01); *A61M 39/20* (2013.01); *A61M 5/001* (2013.01); *A61M 5/002* (2013.01); *A61M 5/3135* (2013.01); *A61M 5/3137* (2013.01); *A61M 5/31513* (2013.01); *A61M 5/347* (2013.01); *A61M 2005/3104* (2013.01); *A61M 2005/31506* (2013.01); *A61M 2025/0019* (2013.01); *A61M 2039/1033* (2013.01)

(58) Field of Classification Search
CPC .................. A61M 39/16; A61M 5/002; A61M 2005/3104; A61M 5/001
See application file for complete search history.

(56) References Cited

U.S. PATENT DOCUMENTS

| | | |
|---|---|---|
| 2,098,340 A | 11/1937 | Henahan |
| 2,436,297 A | 2/1948 | Guarnaschelli |
| 2,457,052 A | 12/1948 | Le Clair |
| 2,771,644 A | 11/1956 | Martin |
| 3,270,743 A | 9/1966 | Gingras |
| 3,301,392 A | 1/1967 | Eddingfield |
| 3,411,665 A | 11/1968 | Blum |
| 3,538,950 A | 11/1970 | Porteners |
| 3,882,858 A | 5/1975 | Klemm |
| 3,977,401 A | 8/1976 | Pike |
| 3,987,930 A | 10/1976 | Fuson |
| 4,041,934 A | 8/1977 | Genese |
| 4,095,810 A | 6/1978 | Ku lie |
| 4,133,441 A | 1/1979 | Mittleman et al. |
| 4,192,443 A | 3/1980 | McLaren |
| 4,243,035 A | 1/1981 | Barrett |
| 4,280,632 A | 7/1981 | Yuhara |
| 4,294,370 A | 10/1981 | Toeppen |
| 4,317,446 A | 3/1982 | Ambrosio et al. |
| 4,335,756 A | 6/1982 | Sharp et al. |
| 4,384,589 A | 5/1983 | Morris |
| 4,402,691 A | 9/1983 | Rosenthal et al. |
| 4,417,890 A | 11/1983 | Dennehey et al. |
| 4,427,126 A | 1/1984 | Ostrowsky |
| 4,432,764 A | 2/1984 | Lopez |
| 4,432,766 A | 2/1984 | Bellotti et al. |
| 4,439,184 A | 3/1984 | Wheeler |
| 4,440,207 A * | 4/1984 | Genatempo .............. A61L 31/16 150/154 |
| 4,444,310 A | 4/1984 | Odell |
| 4,461,368 A | 7/1984 | Plourde |
| 4,480,940 A | 11/1984 | Woodruff |
| 4,507,111 A | 3/1985 | Gordon et al. |
| 4,624,664 A | 11/1986 | Peluso et al. |
| 4,666,057 A | 5/1987 | Come et al. |
| 4,666,427 A | 5/1987 | Larsson et al. |
| 4,671,306 A | 6/1987 | Spector |
| 4,703,762 A | 11/1987 | Rathbone et al. |
| 4,728,075 A | 3/1988 | Paradis |
| 4,728,321 A | 3/1988 | Chen |
| 4,747,502 A | 5/1988 | Luenser |
| 4,752,983 A | 6/1988 | Crieshaber |
| 4,778,447 A | 10/1988 | Velde et al. |
| 4,799,926 A | 1/1989 | Haber |
| 4,810,241 A | 3/1989 | Rogers |
| 4,811,847 A | 3/1989 | Reif et al. |
| 4,813,933 A | 3/1989 | Turner |
| 4,834,271 A | 5/1989 | Litwin |
| 4,927,019 A | 5/1990 | Haber et al. |
| 4,957,637 A | 9/1990 | Cornell |
| 4,983,161 A | 1/1991 | Dadson et al. |
| 4,989,733 A | 2/1991 | Patry |
| 4,991,629 A | 2/1991 | Ernesto et al. |
| 5,065,783 A | 11/1991 | Ogle, II |
| 5,143,104 A | 9/1992 | Iba et al. |
| 5,184,742 A | 2/1993 | DeCaprio et al. |
| 5,190,534 A | 3/1993 | Kendell |
| 5,205,821 A | 4/1993 | Kruger et al. |
| 5,242,421 A | 9/1993 | Chan |
| 5,242,425 A | 9/1993 | White et al. |
| 5,246,011 A | 9/1993 | Caillouette |
| D342,134 S | 12/1993 | Mongeon |
| 5,352,410 A | 10/1994 | Hansen et al. |
| 5,471,706 A | 12/1995 | Wallock et al. |
| 5,536,258 A | 7/1996 | Folden |
| 5,552,115 A | 9/1996 | Malchesky |
| 5,554,135 A | 9/1996 | Menyhay |
| 5,580,530 A | 12/1996 | Kowatsch et al. |
| 5,620,088 A | 4/1997 | Martin et al. |
| 5,624,402 A | 4/1997 | Imbert |
| 5,688,253 A | 11/1997 | Lundquist |
| 5,694,978 A | 12/1997 | Heilmann et al. |
| 5,702,017 A | 12/1997 | Goncalves |
| 5,722,537 A | 3/1998 | Sigler |
| 5,776,116 A | 7/1998 | Lopez |
| 5,792,120 A | 8/1998 | Menyhay |
| 5,810,792 A | 9/1998 | Fangrow, Jr. et al. |
| 5,820,604 A | 10/1998 | Fox et al. |
| 5,827,244 A | 10/1998 | Boettger |
| 5,839,715 A | 11/1998 | Leinsing |
| 5,941,857 A * | 8/1999 | Nguyen .............. A61M 5/3213 604/195 |
| 5,954,957 A | 9/1999 | Chin-Loy et al. |
| 5,971,972 A | 10/1999 | Rosenbaum |
| D416,086 S | 11/1999 | Parris et al. |
| 5,989,229 A | 11/1999 | Chiappetta |
| 6,041,805 A | 3/2000 | Gydesen et al. |
| 6,045,539 A * | 4/2000 | Menyhay ............ A61M 39/162 138/89 |
| 6,068,475 A | 5/2000 | Stoyka, Jr. et al. |
| 6,116,468 A | 9/2000 | Nilson |
| 6,117,114 A | 9/2000 | Paradis |
| 6,126,640 A | 10/2000 | Tucker et al. |
| 6,152,913 A | 11/2000 | Feith et al. |
| 6,158,614 A | 12/2000 | Haines et al. |
| 6,170,522 B1 | 1/2001 | Tanida |
| 6,179,141 B1 | 1/2001 | Nakamura |
| 6,202,870 B1 | 3/2001 | Pearce |
| 6,206,134 B1 | 3/2001 | Stark et al. |
| 6,227,391 B1 | 5/2001 | King |
| 6,245,056 B1 | 6/2001 | Walker et al. |
| 6,250,315 B1 | 6/2001 | Ernster |
| 6,315,761 B1 | 11/2001 | Shcherbina et al. |
| 6,394,983 B1 | 5/2002 | Mayoral et al. |
| 6,402,207 B1 | 6/2002 | Segal et al. |
| 6,550,493 B2 | 4/2003 | Williamson et al. |

(56) References Cited

U.S. PATENT DOCUMENTS

| | | |
|---|---|---|
| 6,555,504 B1 | 4/2003 | Ayai et al. |
| 6,585,691 B1 | 7/2003 | Vitello |
| 6,679,395 B1 | 1/2004 | Pfefferkorn et al. |
| 6,679,870 B1 | 1/2004 | Finch et al. |
| 6,681,803 B2 | 1/2004 | Taneya et al. |
| 6,685,694 B2 | 2/2004 | Finch et al. |
| 6,692,468 B1 | 2/2004 | Waldenburg |
| 6,716,396 B1 | 4/2004 | Anderson |
| 6,827,766 B2 | 12/2004 | Carnes et al. |
| 6,911,025 B2 | 6/2005 | Miyahar |
| 6,943,035 B1 | 9/2005 | Davies et al. |
| 7,056,308 B2 | 6/2006 | Utterberg |
| 7,083,605 B2 | 8/2006 | Miyahara |
| 7,160,272 B1 | 1/2007 | Eyal et al. |
| 7,198,611 B2 | 4/2007 | Connell et al. |
| 7,282,186 B2 | 10/2007 | Lake, Jr. et al. |
| 7,309,326 B2 | 12/2007 | Fangrow, Jr. |
| 7,431,712 B2 | 10/2008 | Kim |
| 7,452,349 B2 | 11/2008 | Miyahar |
| 7,516,846 B2 | 4/2009 | Hansen |
| 7,614,426 B2 | 11/2009 | Kitani et al. |
| 7,635,344 B2 | 12/2009 | Tennican et al. |
| D607,325 S | 1/2010 | Rogers et al. |
| 7,708,714 B2 | 5/2010 | Connell et al. |
| 7,731,678 B2 | 6/2010 | Tennican et al. |
| 7,731,679 B2 | 6/2010 | Tennican et al. |
| 7,749,189 B2 | 7/2010 | Tennican et al. |
| 7,753,891 B2 | 7/2010 | Tennican et al. |
| 7,763,006 B2 | 7/2010 | Tennican |
| 7,766,182 B2 | 8/2010 | Trent et al. |
| 7,766,897 B2 | 8/2010 | Ramsey et al. |
| 7,776,011 B2 | 8/2010 | Tennican et al. |
| 7,780,794 B2 | 8/2010 | Rogers et al. |
| 7,794,675 B2 | 9/2010 | Lynn |
| 7,799,010 B2 | 9/2010 | Tennican |
| 7,815,614 B2 | 10/2010 | Fangrow, Jr. |
| 7,857,793 B2 | 12/2010 | Raulerson et al. |
| 7,922,701 B2 | 4/2011 | Buchman |
| 7,959,026 B2 | 6/2011 | Bertani |
| 7,985,302 B2 | 7/2011 | Rogers et al. |
| 7,993,309 B2 | 8/2011 | Schweikert |
| 8,065,773 B2 | 11/2011 | Vaillancourt et al. |
| 8,066,670 B2 | 11/2011 | Cluff et al. |
| 8,069,523 B2 | 12/2011 | Vaillancourt et al. |
| 8,113,837 B2 | 2/2012 | Zegarelli |
| 8,162,899 B2 | 4/2012 | Tennican |
| 8,167,847 B2 | 5/2012 | Anderson et al. |
| 8,172,825 B2 | 5/2012 | Solomon et al. |
| 8,206,514 B2 | 6/2012 | Rogers et al. |
| 8,231,587 B2 | 7/2012 | Solomon et al. |
| 8,231,602 B2 | 7/2012 | Anderson et al. |
| 8,262,628 B2 | 9/2012 | Fangrow, Jr. |
| 8,262,643 B2 | 9/2012 | Tennican |
| 8,273,303 B2 | 9/2012 | Ferlic et al. |
| 8,281,824 B2 | 10/2012 | Molema et al. |
| 8,361,408 B2 | 1/2013 | Lynn |
| 8,372,045 B2 | 2/2013 | Needle et al. |
| 8,377,040 B2 | 2/2013 | Burkhoiz et al. |
| 8,480,968 B2 | 7/2013 | Lynn |
| 8,523,831 B2 | 9/2013 | Solomon et al. |
| 8,545,479 B2 | 10/2013 | Kitani et al. |
| 8,647,326 B2 | 2/2014 | Solomon et al. |
| 8,740,864 B2 | 6/2014 | Hoang et al. |
| 8,777,504 B2 | 7/2014 | Shaw et al. |
| 8,845,593 B2 | 9/2014 | Anderson et al. |
| 8,910,919 B2 | 12/2014 | Bonnal et al. |
| 8,968,268 B2 | 3/2015 | Anderson et al. |
| 9,095,500 B2 | 8/2015 | Brandenburger et al. |
| 9,095,667 B2 | 8/2015 | Von Schuckmann |
| 9,101,750 B2 | 8/2015 | Solomon et al. |
| 9,114,915 B2 | 8/2015 | Solomon et al. |
| 9,125,600 B2 | 9/2015 | Steube et al. |
| 9,149,624 B2 | 10/2015 | Lewis |
| 9,192,449 B2 | 11/2015 | Kerr et al. |
| 9,216,440 B2 | 12/2015 | Ma et al. |
| 9,242,084 B2 | 1/2016 | Solomon et al. |
| 9,259,284 B2 | 2/2016 | Rogers et al. |
| 9,259,535 B2 | 2/2016 | Anderson et al. |
| 9,283,367 B2 | 3/2016 | Hoang et al. |
| 9,283,368 B2 | 3/2016 | Hoang et al. |
| 9,289,588 B2 | 3/2016 | Chen |
| 9,302,049 B2 | 4/2016 | Tekeste |
| 9,320,858 B2 | 4/2016 | Grimm et al. |
| 9,320,859 B2 | 4/2016 | Grimm et al. |
| 9,320,860 B2 | 4/2016 | Grimm et al. |
| 9,352,140 B2 | 5/2016 | Kerr et al. |
| 9,352,141 B2 | 5/2016 | Wong |
| 9,399,125 B2 | 7/2016 | Burkholz |
| 9,408,971 B2 | 8/2016 | Carlyon |
| 9,527,660 B2 | 12/2016 | Tennican |
| 9,592,375 B2 | 3/2017 | Tennican |
| 9,700,676 B2 | 7/2017 | Anderson et al. |
| 9,700,677 B2 | 7/2017 | Anderson et al. |
| 9,700,710 B2 * | 7/2017 | Anderson .......... A61M 5/31511 |
| 9,707,350 B2 | 7/2017 | Anderson et al. |
| 9,809,355 B2 | 11/2017 | Solomon et al. |
| 9,867,975 B2 | 1/2018 | Gardner et al. |
| 9,933,094 B2 | 4/2018 | Fangrow |
| 10,016,587 B2 | 7/2018 | Gardner et al. |
| 10,046,156 B2 | 8/2018 | Gardner |
| 10,166,381 B2 | 1/2019 | Gardner et al. |
| 2002/0193752 A1 | 12/2002 | Lynn |
| 2003/0082376 A1 | 4/2003 | Sears et al. |
| 2003/0153865 A1 | 8/2003 | Connell et al. |
| 2004/0034042 A1 | 2/2004 | Tsuji et al. |
| 2004/0048542 A1 | 3/2004 | Thomascheisky et al. |
| 2004/0215148 A1 | 10/2004 | Hwang et al. |
| 2005/0013836 A1 | 1/2005 | Raad |
| 2005/0065479 A1 | 3/2005 | Schiller et al. |
| 2005/0124970 A1 | 6/2005 | Kunin et al. |
| 2005/0147524 A1 | 7/2005 | Bousquet |
| 2005/0148930 A1 | 7/2005 | Hseih et al. |
| 2005/0214185 A1 | 9/2005 | Castaneda |
| 2006/0261076 A1 | 11/2006 | Anderson |
| 2007/0167910 A1 | 7/2007 | Tennican et al. |
| 2007/0187353 A1 | 8/2007 | Fox et al. |
| 2007/0249996 A1 | 10/2007 | Tennican et al. |
| 2007/0265578 A1 | 11/2007 | Tennican et al. |
| 2007/0287989 A1 | 12/2007 | Crawford et al. |
| 2008/0027399 A1 | 1/2008 | Harding et al. |
| 2008/0033371 A1 | 2/2008 | Updegraff et al. |
| 2008/0039803 A1 | 2/2008 | Lynn |
| 2008/0058733 A1 | 3/2008 | Vogt et al. |
| 2008/0093245 A1 | 4/2008 | Periasamy et al. |
| 2008/0095680 A1 | 4/2008 | Steffens et al. |
| 2008/0097315 A1 | 4/2008 | Miner et al. |
| 2008/0147047 A1 | 6/2008 | Davis et al. |
| 2008/0177250 A1 | 7/2008 | Howlett et al. |
| 2008/0287920 A1 | 11/2008 | Fangrow et al. |
| 2009/0008393 A1 | 1/2009 | Howlett et al. |
| 2009/0012426 A1 | 1/2009 | Tennican |
| 2009/0062766 A1 | 3/2009 | Howlett et al. |
| 2009/0093757 A1 | 4/2009 | Tennican |
| 2009/0099529 A1 | 4/2009 | Anderson et al. |
| 2009/0137969 A1 | 5/2009 | Colantonio et al. |
| 2009/0205151 A1 | 8/2009 | Fisher et al. |
| 2009/0205656 A1 | 8/2009 | Nishibayashi et al. |
| 2009/0259194 A1 | 10/2009 | Pinedjian et al. |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0064456 A1 | 3/2010 | Ferlic |
| 2010/0152670 A1 | 6/2010 | Low |
| 2010/0160894 A1 | 6/2010 | Julian et al. |
| 2010/0172794 A1 | 7/2010 | Ferlic et al. |
| 2010/0242993 A1 | 9/2010 | Hoang et al. |
| 2010/0253070 A1 | 10/2010 | Cheon et al. |
| 2010/0306938 A1 | 12/2010 | Rogers et al. |
| 2011/0030726 A1 | 2/2011 | Vaillancourt et al. |
| 2011/0044850 A1 | 2/2011 | Solomon et al. |
| 2011/0046564 A1 | 2/2011 | Zhong |
| 2011/0046603 A1 | 2/2011 | Felsovalyi et al. |
| 2011/0062703 A1 | 3/2011 | Lopez |
| 2011/0064512 A1 | 3/2011 | Shaw et al. |

(56) References Cited

U.S. PATENT DOCUMENTS

| | | |
|---|---|---|
| 2011/0082431 A1 | 4/2011 | Burgess et al. |
| 2011/0217212 A1 | 9/2011 | Solomon et al. |
| 2011/0232020 A1 | 9/2011 | Rogers et al. |
| 2011/0265825 A1 | 11/2011 | Rogers et al. |
| 2011/0314619 A1 | 12/2011 | Schweikert |
| 2012/0031904 A1 | 2/2012 | Kuhn et al. |
| 2012/0109073 A1 | 5/2012 | Anderson et al. |
| 2012/0157965 A1 | 6/2012 | Wotton et al. |
| 2012/0195807 A1 | 8/2012 | Ferlic |
| 2012/0216359 A1 | 8/2012 | Rogers et al. |
| 2012/0216360 A1 | 8/2012 | Rogers et al. |
| 2012/0283696 A1 | 11/2012 | Cronenberg et al. |
| 2012/0296284 A1 | 11/2012 | Anderson et al. |
| 2012/0302970 A1 | 11/2012 | Tennican |
| 2012/0302997 A1 | 11/2012 | Gardner et al. |
| 2013/0030414 A1 | 1/2013 | Gardner et al. |
| 2013/0035667 A1 | 2/2013 | Anderson et al. |
| 2013/0053751 A1 | 2/2013 | Holtham |
| 2013/0098938 A1 | 4/2013 | Efthimiadis |
| 2013/0171030 A1 | 7/2013 | Ferlic et al. |
| 2013/0183635 A1 | 7/2013 | Wilhoit |
| 2014/0101876 A1 | 4/2014 | Rogers et al. |
| 2014/0155868 A1 | 6/2014 | Nelson et al. |
| 2015/0018774 A1 | 1/2015 | Anderson et al. |
| 2015/0217106 A1 | 8/2015 | Banik et al. |
| 2015/0237854 A1 | 8/2015 | Mills et al. |
| 2015/0258324 A1 | 9/2015 | Chide et al. |
| 2015/0314119 A1 | 11/2015 | Anderson et al. |
| 2015/0314120 A1 | 11/2015 | Gardner et al. |
| 2015/0374968 A1 | 12/2015 | Solomon et al. |
| 2016/0001058 A1 | 1/2016 | Ziebol et al. |
| 2016/0045629 A1 | 2/2016 | Gardner et al. |
| 2016/0067471 A1 | 3/2016 | Ingram et al. |
| 2016/0088995 A1 | 3/2016 | Ueda et al. |
| 2016/0089530 A1 | 3/2016 | Sathe |
| 2016/0101276 A1 | 4/2016 | Tekeste |
| 2016/0106969 A1 | 4/2016 | Neftel |
| 2016/0121097 A1 | 5/2016 | Steele |
| 2016/0144118 A1 | 5/2016 | Solomon et al. |
| 2016/0158521 A1 | 6/2016 | Hoang et al. |
| 2016/0158522 A1 | 6/2016 | Hoang et al. |
| 2016/0184527 A1 | 6/2016 | Tekeste |
| 2016/0213912 A1 | 7/2016 | Daneluzzi |
| 2016/0250420 A1 | 9/2016 | Maritan et al. |
| 2017/0239443 A1 | 8/2017 | Abitabilo et al. |
| 2018/0369562 A1 | 12/2018 | Gardner |
| 2019/0038888 A1 | 2/2019 | Gardner |

FOREIGN PATENT DOCUMENTS

| | | |
|---|---|---|
| CA | 2 583 601 | 4/2006 |
| CA | 2 626 864 | 5/2007 |
| CA | 2 651 192 | 11/2007 |
| CA | 2 615 146 | 6/2008 |
| CN | 2402327 Y | 10/2000 |
| CN | 2815392 Y | 9/2006 |
| CN | 201150420 Y | 11/2008 |
| CN | 201519335 U | 7/2010 |
| DE | 89 06 628 U1 | 9/1989 |
| DE | 29617133 | 1/1997 |
| EP | 0 108 785 | 5/1984 |
| EP | 0 227 219 | 7/1987 |
| EP | 0 245 872 | 11/1987 |
| EP | 0 639 385 | 2/1995 |
| EP | 0 769 265 | 4/1997 |
| EP | 1 061 000 | 10/2000 |
| EP | 1 331 020 | 7/2003 |
| EP | 1 977 714 | 10/2008 |
| EP | 2 444 117 | 4/2012 |
| EP | 2 606 930 | 6/2013 |
| FR | 2 493 149 A | 5/1982 |
| FR | 2 782 910 | 3/2000 |
| GB | 123221 | 2/1919 |
| GB | 2 296 182 | 6/1996 |
| GB | 2 333 097 | 7/1999 |
| GB | 2 387 772 | 10/2003 |
| JP | 04-99950 | 2/1992 |
| JP | 2000157630 A | 6/2000 |
| JP | 2002-291906 | 10/2002 |
| JP | 2006-182663 A | 7/2006 |
| RU | 2 246 321 C1 | 2/2005 |
| WO | WO 1983/03975 | 11/1983 |
| WO | WO 1985/05040 | 11/1985 |
| WO | WO 1998/12125 | 3/1998 |
| WO | WO 2004/035129 | 4/2004 |
| WO | WO 2004/112846 | 12/2004 |
| WO | WO 2006/007690 | 1/2006 |
| WO | WO 2006/044236 | 4/2006 |
| WO | WO 2007/008511 | 1/2007 |
| WO | WO 2007/056773 | 5/2007 |
| WO | WO 2007/137056 | 11/2007 |
| WO | WO 2008/042285 | 4/2008 |
| WO | WO 2008/086631 | 7/2008 |
| WO | WO 2008/089196 | 7/2008 |
| WO | WO 2008/100950 | 8/2008 |
| WO | WO 2008/140807 | 11/2008 |
| WO | WO 2009/002474 | 12/2008 |
| WO | WO 2009/117135 | 9/2009 |
| WO | WO 2009/123709 | 10/2009 |
| WO | WO 2009/136957 | 11/2009 |
| WO | WO 2009/153224 | 12/2009 |
| WO | WO 2010/002757 | 1/2010 |
| WO | WO 2010/002808 | 1/2010 |
| WO | WO 2010/034470 | 4/2010 |
| WO | WO 2010/039171 | 4/2010 |
| WO | WO 2011/028722 | 3/2011 |
| WO | WO 2011/119021 | 9/2011 |
| WO | WO 2012/162006 | 11/2012 |
| WO | WO 2012/184716 | 12/2013 |
| WO | WO 2013/192574 | 12/2013 |
| WO | WO 2014/140949 | 9/2014 |
| WO | WO 2015/119940 | 8/2015 |
| WO | WO 2017/015047 | 1/2017 |
| WO | WO 2018/009653 | 1/2018 |
| WO | WO 2018/071717 | 4/2018 |
| WO | WO 2018/237090 | 12/2018 |

OTHER PUBLICATIONS

Baxter, "Peritoneal Dialysis Patient Connectology," Product Descriptions in 1 page, downloaded Jul. 1, 2011.

Catheter Connections, "Introducing DualCap," Product Brochure in 1 page, Copyright 2011.

Conical Fittings: International Standard, "Conical fittings with 6% (Luer) Taper for Syringes, Needles and certain Other Medical Equipment—Part 2: Lock Fittings", Ref. No. ISO 594-2:1998. International Organization for Standardization (Sep. 1, 1998) 2nd ed. (16 pages).

Devine, redacted version of letter from David A. Divine, Esq. of Lee & Hayes, dated May 16, 2011 (3 pages).

Devine, redacted version of letter from David A. Divine, Esq. of Lee & Hayes, dated May 27, 2011 (3 pages).

Hospira, "You Work in Neverland," Lifeshield Product Brochure in 2 pages, Published 2009.

Hyprotek, "Port Protek," Product Brochure in 1 page, downloaded Sep. 19, 2011 from http://www.hyprotek.com/products.html.

Menyhay et al., "Disinfection of Needleless Catheter Connectors and Access Ports with Alcohol May Not Prevent Microbial Entry: The Promise of a Novel Antiseptic-Barrier Cap" Infection Control Hospital and Epidemiology, vol. 27, No. 1 (Jan. 2006) (5 pages).

Photographs of the Baxter Minicap (Sep. 1, 1998) (4 pages).

European Exam Report, re EP Application No. 12845250.5, dated Sep. 1, 2017.

Charney, "Baxter Healthcare InterlinkTM IV Access System" in 1 page, from Handbook of Modern Hospital Safety. Published Mar. 1999.

* cited by examiner

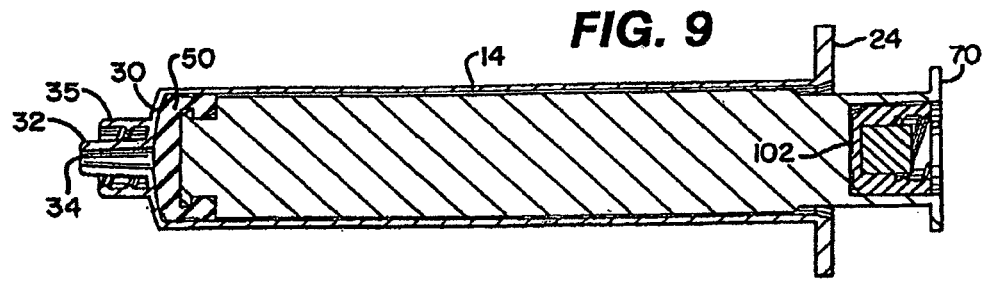
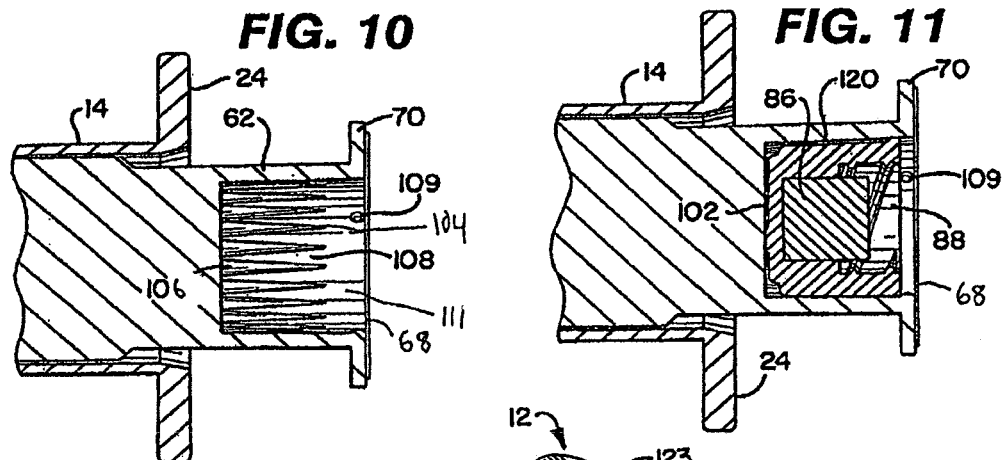
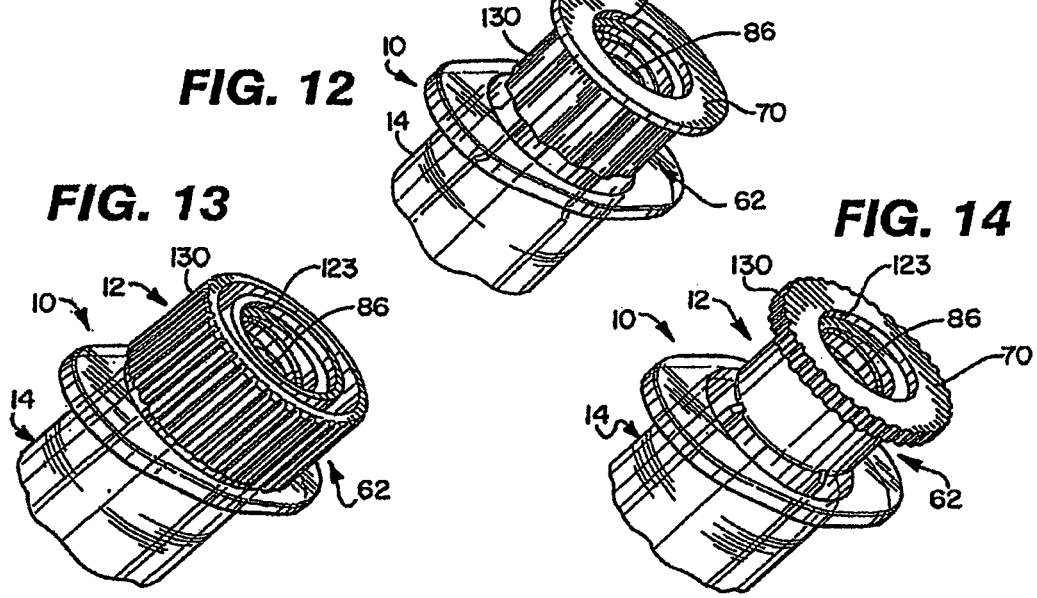

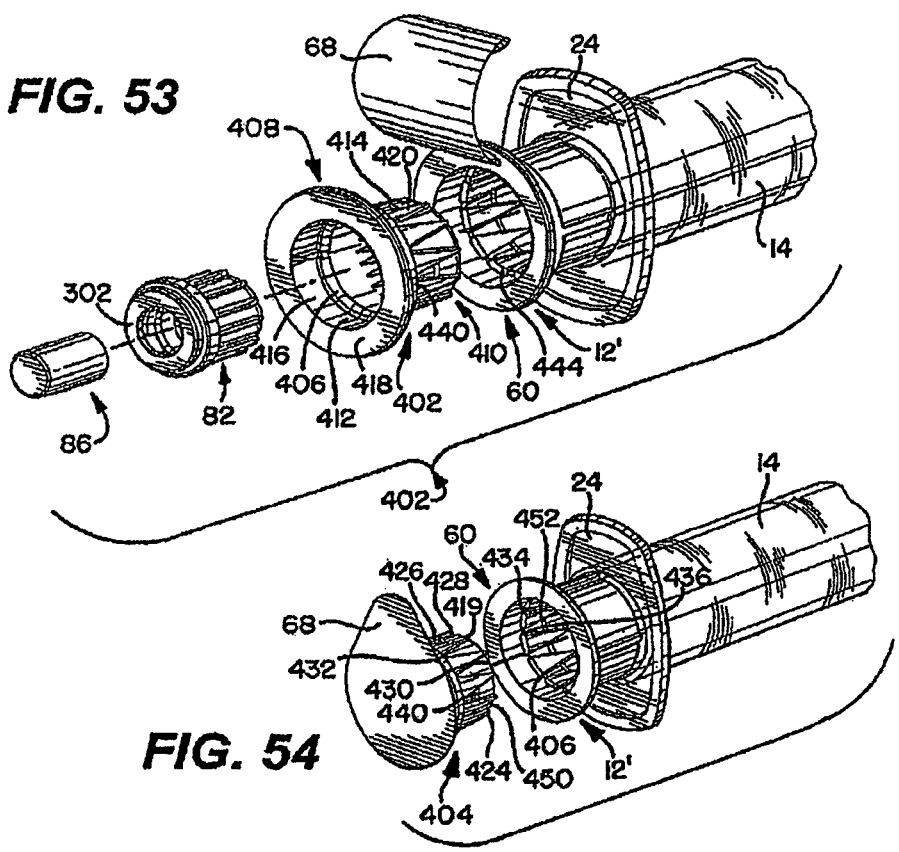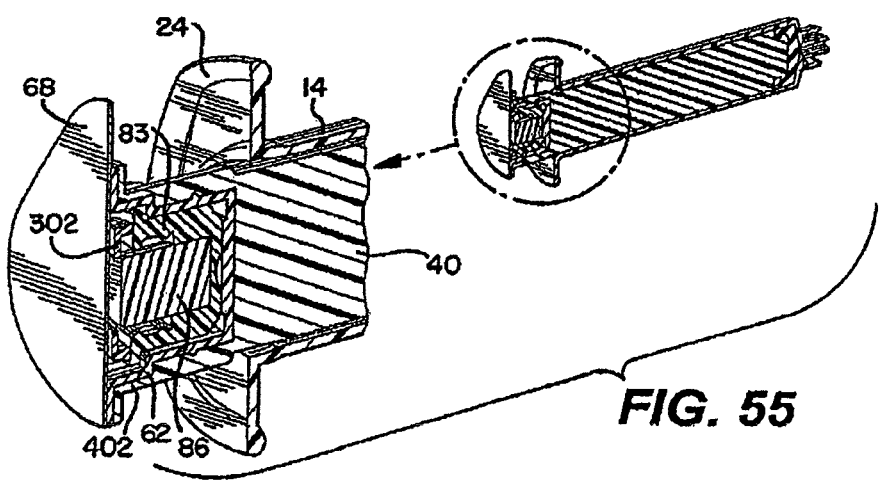

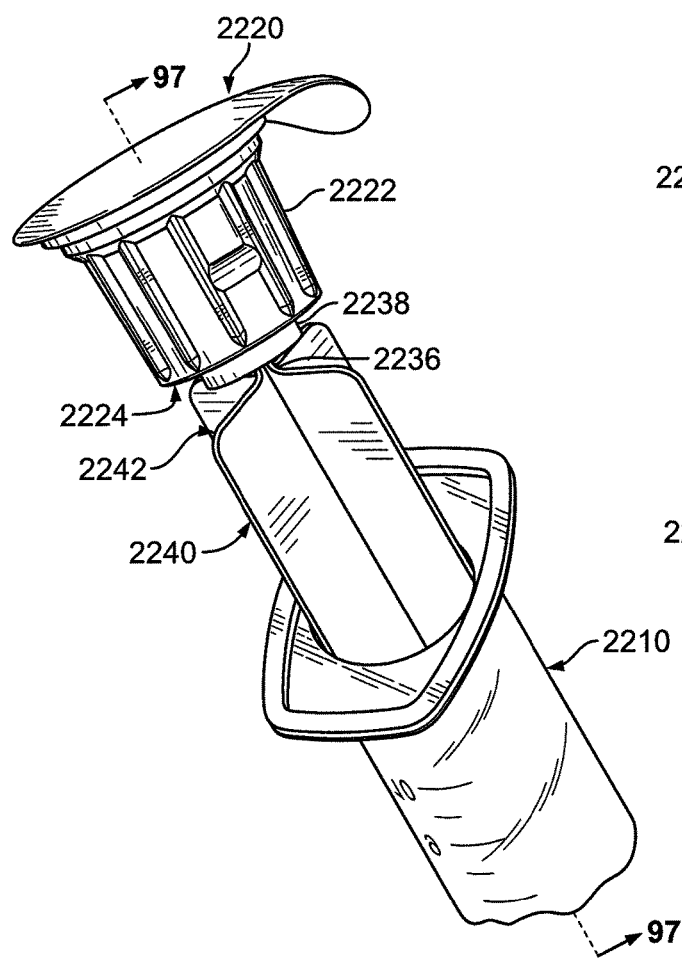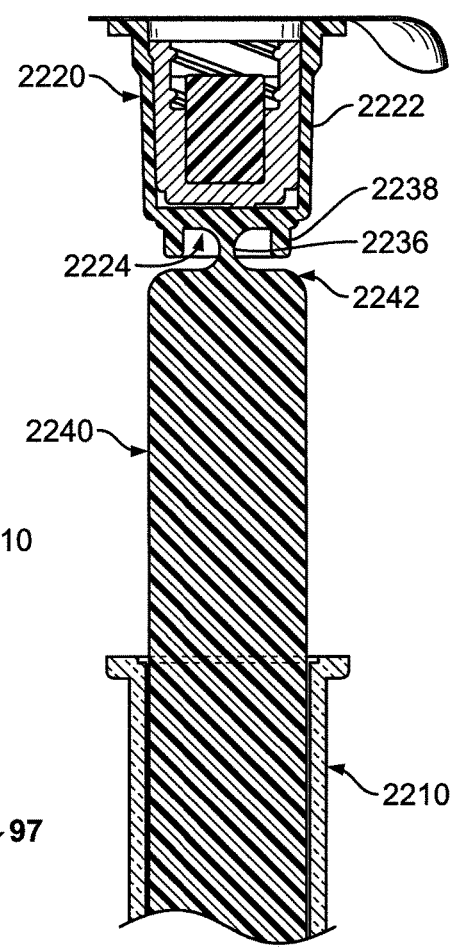
FIG. 96
FIG. 97

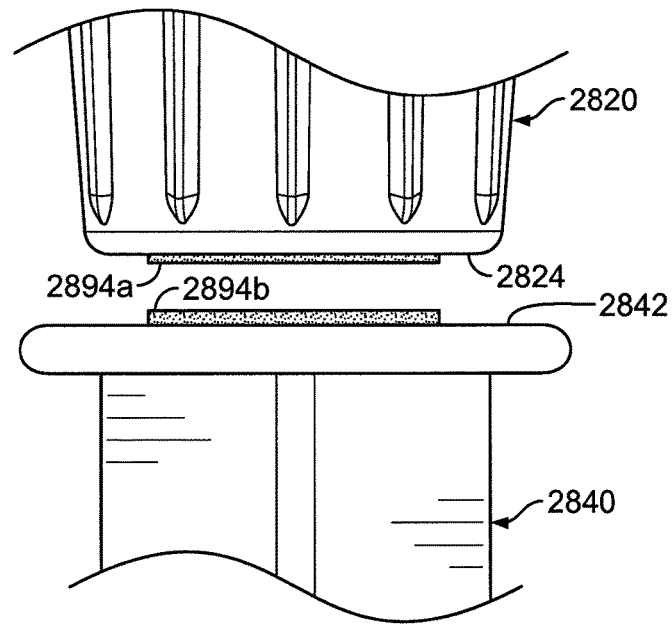
FIG. 111
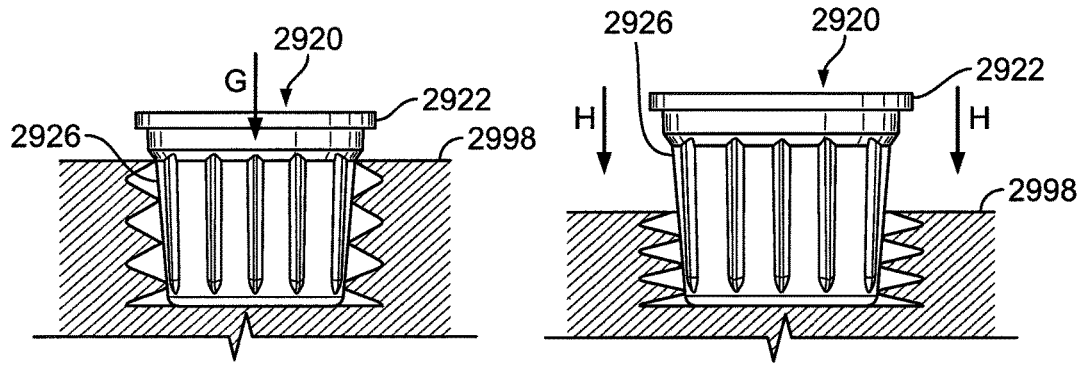
FIG. 112  FIG. 113

ANTISEPTIC CAP

CROSS-REFERENCE TO RELATED APPLICATIONS

This application is a continuation application of U.S. patent application Ser. No. 14/799,022, filed on Jul. 14, 2015, now U.S. Pat. No. 9,707,350, which is a continuation application of U.S. patent application Ser. No. 13/547,650, filed on Jul. 12, 2012, now U.S. Pat. No. 9,259,535, which is a continuation-in-part of U.S. patent application Ser. No. 13/288,529, filed on Nov. 3, 2011, now U.S. Pat. No. 9,700,710, which is a continuation-in-part of U.S. application Ser. No. 12/214,526, filed on Jun. 19, 2008, now U.S. Pat. No. 9,707,348, which is a continuation-in-part of U.S. application Ser. No. 11/821,190 filed on Jun. 22, 2007, now U.S. Pat. No. 8,167,847, which claims the benefit of U.S. Provisional Application Ser. No. 60/815,806 filed on Jun. 22, 2006, and U.S. patent application Ser. No. 13/288,529 is a continuation-in-part of U.S. application Ser. No. 11/821,190 filed on Jun. 22, 2007, now U.S. Pat. No. 8,167,847, which claims the benefit of U.S. Provisional Application Ser. No. 60/815,806 filed on Jun. 22, 2006, the entire disclosures of which are all expressly incorporated herein by reference.

BACKGROUND OF THE INVENTION

Technical Field

The present invention relates to an antiseptic cap equipped syringe, and more specifically to antiseptic caps disposed on syringes.

Background Art

Catheters are widely used to treat patients requiring a variety of medical procedures. Catheters can either be acute, or temporary, for short-term use or chronic for long-term treatment. Catheters are commonly inserted into central veins (such as the vena cava) from peripheral vein sites to provide access to a patient's vascular system. Catheters offer many advantages for patients; for example, chronic catheters provide ready access without repeated punctures or repeated vessel cannulation for administration of large volumes of fluids, nutrients and medications and for withdrawal of blood on an intermittent basis. With respect to the use of catheters for infusion of fluids, examples include the infusion of drugs, electrolytes or fluids used in chemotherapy. In chemotherapy, catheters are used for infusion of drugs on an intermittent basis, ranging from daily to weekly. Another example includes the use of catheters in hyperalimentation treatment, wherein the catheters are usually used for infusion of large volumes of fluids.

For hemodialysis, catheters are commonly used—usually three times per week—for aspiration of blood for dialysis treatment and rapid return of the blood to circulation after treatment. Although a preferred mode of vascular access for a hemodialysis patient involves using an arteriovenous (AV) fistula of either the upper or lower extremities or an arteriovenous "bridge" graft (typically utilizing PTFE), use of these access devices is not always possible or desirable. When either of these modes of vascular access is not available, for example, due to a paucity of adequate blood vessels for creation of AV "shunts" or due to nonoptimally functioning established AV shunts, a large bore venous line catheter is typically required for hemodialysis. Catheters used for hemodialysis usually include two relatively large diameter lumens (usually molded as one catheter) for aspiration and rapid return of blood required during the hemodialysis procedure. One lumen of such a catheter is used for aspiration, or removal, of blood, while the other lumen is used for returning the blood to the patient's bloodstream.

Catheter connections, such as, for example, connections of catheters to dialysis machine tubing, to IV line tubing, to infusion ports and to catheter caps, which are used to seal the end of a catheter to protect the sterility of the catheter and prevent fluid loss and/or particle contamination, are most often made utilizing the medical industry's standardized Luer taper fittings. These fittings, which may either be male couplings or female couplings, include a tapered end of standardized dimensions. Coupling is made by the press-fit of mating parts. A threaded lock-fit or other type of securing mechanism is commonly utilized to ensure the integrity of the pressure fit of the Luer fittings.

Catheters, especially chronic venous catheters, provide challenges in their use. One such challenge is that such catheters can become occluded by a thrombus. In order to prevent clotting of catheters in blood vessels between uses, such as, for example, between dialysis treatments when the catheter is essentially nonfunctioning and dwells inside a "central" vein (i.e. superior vena cava, inferior vena cava, iliac, etc.), the lumens of the catheter are often filled with a lock solution of a concentrated solution of the commonly used anticoagulant, heparin (up to 10,000 units of heparin per catheter lumen).

As used herein, the terms "lock solution" or "locking solution" refer to a solution that is injected or otherwise infused into a lumen of a catheter with the intention of allowing a substantial portion of the lock solution to remain in the lumen and not in the systemic blood circulation until it is desired or required to access that particular lumen again, typically for additional treatment, i.e., infusion or withdrawal of fluid. In addition, attention has been given to the development of alternative lock solutions with the goal of improving the patency rates of vascular catheters. For example, lower-alcohol containing locking solutions are under development wherein the lower alcohols include ethanol, propanol and butanol. Anti-microbial and/or anti-coagulant additives can optionally be added to the lower-alcohol containing locking solution. Preferably the lock solution can remain in the lumen for a desired amount of time lasting from about 1 hour to 3 or 4 days or longer.

For the reasons set forth above, significant care must be taken when infusing medications, nutrients and the like into a catheter, and when "locking" a catheter between uses, to minimize the risks associated with an indwelling catheter, including the risk of thrombosis or clotting, the risk of excessive anticoagulating and the risk of infection. Syringes are typically used to administer the required amount of catheter lock solution (determined by the catheter manufacturer) into an indwelling catheter after a given use. Flush procedures also require that care be taken to prevent blood reflux into the catheter. Reflux in I.V. therapy is the term commonly used to describe the fluid that is drawn back into the catheter after a flush procedure. The concern is that the reflux fluid contains blood or solution that could cause the catheter to occlude. To ensure that reflux does not occur, flush procedures suggest two techniques: 1) at the end of the flush solution delivery, the user maintains pressure on the syringe plunger while clamping the I.V. line; or 2) while delivering the last 0.5 ml of flush solution disconnect the syringe from the I.V. port or clamp the I.V. line. Either technique maintains positive pressure on the fluid in the catheter to prevent reflux of fluid and blood.

It has been found that the use of antiseptic caps, such as the cap manufactured and sold by Excelsior under the trademark SwabCap, greatly reduce the incidence of infections, resulting in, among other things, significant health benefits for patients and vast cost savings.

In light of the above-described problems, there is a continuing need for advancements in catheter lock techniques, devices and procedures to improve the safety and efficacy of catheter locking procedures and of overall patient care.

SUMMARY OF THE INVENTION

The present invention relates to an antiseptic cap and syringe combination. The combination includes a syringe barrel having an access point connection, and a tip cap having a proximal chamber and a distal chamber. The proximal chamber releasably receives and engages the access point connection of the syringe. The distal chamber removably receives and engages an antiseptic cap. In one embodiment, the distal chamber has a plurality of ribs for coacting with a plurality of ribs on the antiseptic cap to prevent relative rotational movement between the distal chamber and the antiseptic cap.

In one embodiment, a combination syringe tip cap and antiseptic cap includes a first chamber having means for releasably engaging an access point connection on a syringe. A second chamber is formed integrally with the first chamber. An antiseptic cap is positioned within the second chamber, and means for releasably engaging the antiseptic cap is provided in the second chamber.

A method of storing an antiseptic cap of a syringe is provided. The method includes the steps of providing a syringe having a barrel, a plunger, an access point connection and a tip cap, providing a chamber on the syringe, and releaseably engaging an antiseptic cap within the chamber.

A method of using an antiseptic cap disposed on a tip cap of a syringe having a barrel, a plunger, an access point connection and a tip cap is also provided. The method includes the steps of removing the tip cap from the syringe, and using the syringe. The method further includes the step of removing a cover over the antiseptic cap. Steps of using a tip cap to position the antiseptic cap on an access point, and removing the tip cap from engagement with the antiseptic cap, leaving the antiseptic cap on the access point are included.

In one embodiment, a combination syringe tip cap and antiseptic cap includes a first chamber having means for releasably engaging an access point connection on a syringe, and a second chamber formed integrally with the first chamber. An antiseptic cap assembly has an antiseptic cap, and the antiseptic cap assembly is removably positioned within the second chamber.

In another embodiment, an antiseptic cap and syringe combination includes a syringe barrel having an access point connection, and a plunger received at one end by the barrel. The plunger has a chamber removeably receiving an antiseptic cap assembly at a second end. A tip cap has a proximal chamber for releasably receiving the access point connection of the syringe, and a distal chamber for removeably receiving a second antiseptic cap assembly.

In another embodiment, an antiseptic cap and syringe combination includes a syringe barrel having an access point connection, and a plunger received at one end by the barrel. A chamber is interconnected with the syringe barrel for removeably receiving an antiseptic cap assembly.

In another embodiment, an antiseptic cap and syringe combination includes a syringe barrel having an access point connection and an antiseptic cap. A flexible ring for engaging the access point, and a chamber interconnected with the syringe barrel for removeably receiving an antiseptic cap are provided.

In another embodiment, an antiseptic cap and syringe combination includes a syringe barrel having an access point connection and a tip cap including a proximal chamber releasably receiving and engaging the access point connection of the syringe. A distal projection extends from the tip cap, and an antiseptic cap assembly has a chamber for receiving the distal projection of the tip cap at one end and an antiseptic cap at the other end.

In another embodiment, an antiseptic cap and syringe combination includes a syringe barrel having an access point connection, a tip cap including a proximal chamber for engaging the access point connection and a distal attachment chamber, and a cap assembly. The cap assembly includes an engagement protrusion for removeably engaging the tip cap.

BRIEF DESCRIPTION OF THE DRAWINGS

FIG. 9 is a side view in cutaway of an antiseptic cap equipped plunger and syringe barrel assembly;

FIG. 10 shows an exploded view of a detail of FIG. 9 of one embodiment of the antiseptic cap equipped plunger and syringe barrel assembly;

FIG. 11 shows an exploded view of a detail of FIG. 9 of another embodiment of the antiseptic cap equipped plunger and syringe barrel assembly;

FIGS. 12-14 show various embodiments of grips of the antiseptic cap equipped plunger assembly;

FIG. 53 is an assembly view of an antiseptic cap and cup holder equipped plunger and syringe barrel system;

FIG. 54 is an assembly view of a cup-holder-antiseptic cap assembly adjacent a plunger and syringe barrel system;

FIG. 55 is a side view in cross-section of an antiseptic cap and cup holder equipped plunger and syringe barrel assembly;

FIG. 96 is a perspective view of a plunger and cap holder assembly connected by a frangible attachment;

FIG. 97 is a cross-sectional view of the plunger and cap holder assembly of FIG. 96;

FIG. 111 is a side view of a cap holder assembly and a plunger each having an adhesive material thereon;

FIG. 112 is a side view of a cap holder assembly and a plunger with compressible material in an uncompressed state;

FIG. 113 is a side view of a cap holder assembly and plunger with the compressible material in a compressed state;

DETAILED DESCRIPTION OF THE INVENTION

Figure 1:
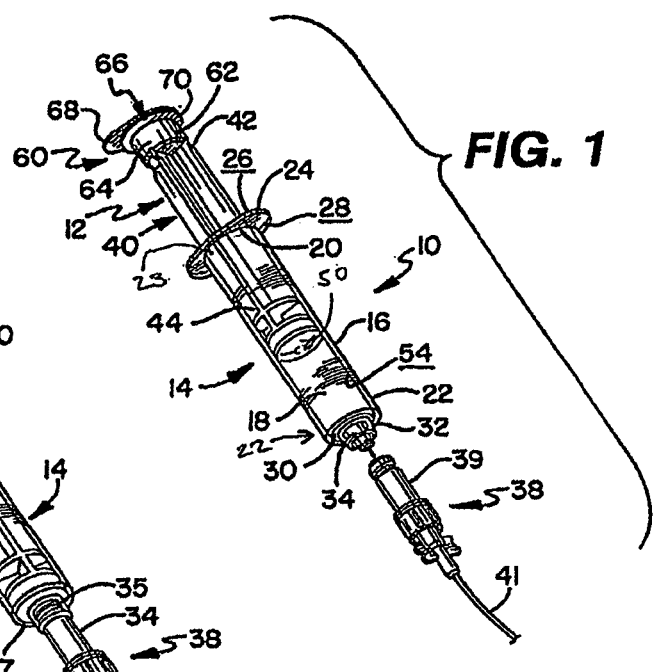
FIG. 1 is a perspective view of an antiseptic cap equipped plunger and syringe barrel assembly prior to connection of a syringe tip to an access point to a central venous catheter.

While this invention is susceptible of embodiment in many different forms, there is shown in the drawings, and will be described herein in detail, specific embodiments thereof with the understanding that the present disclosure is to be considered as an exemplification of the principles of the invention and is not intended to limit the invention to the specific embodiments illustrated.

Figure 2:
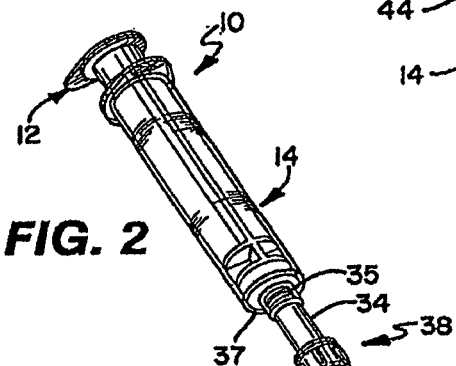
FIG. 2 is a perspective view of an antiseptic cap equipped plunger and syringe barrel assembly with the syringe tip connected to an access point to a central venous catheter.

FIGS. 1 and 2 show an antiseptic cap equipped plunger and syringe barrel assembly 10 having an antiseptic cap equipped plunger (or piston) assembly 12 and a syringe barrel 14. The barrel 14 has a side wall 16 defining a chamber 18 and the barrel has a proximal end 20 and a distal end 22. The proximal end 20 has an opening 22 to the chamber 18 and a flange 24 extending radially outwardly from the wall 16. The flange 24 has upper and lower surfaces 26, 28 and provides gripping surfaces for a user of the assembly 10. The distal end 22 of the barrel 14 has an end wall 30 and an elongate tip 32 extending distally therefrom and having a passageway 34 therethrough and in fluid communication with the chamber 18. The distal end wall 30, in one preferred form of the invention, is generally conically shaped and, as is well known in the art, can have a locking luer collar 35 concentrically surrounding the tip 32 and having a set of threads 37 on an inside surface thereof. The luer collar 35 allows for attaching a needle or a cannula to the syringe assembly and for docking the assembly to mating threads located on other devices such as valves and injection sites. FIG. 1 shows the syringe assembly proximate an access site 38 having a valve 39 controlling access to a lumen of a tubing 41.

In one preferred form of the invention the chamber 18 of the syringe assembly 10 will be filled with a locking solution or a flush solution for use with an indwelling, central venous catheter. The manner of using a locking or flush solution with a catheter is well known in the art. Suitable locking or flushing solutions will be set forth below. The flush or locking solution is injected into a fluid access site of the catheter to clean and disinfect the catheter and can be withdrawn from the catheter or allowed to remain in an end portion of the catheter to serve as a barrier to the ingress of pathogens and contaminants.

The antiseptic cap plunger assembly 12 has an elongate shaft 40, a proximal end 42 and a distal end 44. The elongate shaft 40, in one preferred form of the invention, is generally cruciform in cross-sectional shape. A stopper or piston 50 is connected to the distal end 44 of the plunger 12. The piston 50 is dimensioned such that when inserted into the syringe barrel chamber 18 an outer circumferential surface of the piston is in fluid-tight engagement with an inner surface 54 of the syringe barrel. The piston assembly 12 when moved proximally (or when being withdrawn) can draw fluid into the chamber and when moved distally (or when inserted into the syringe chamber) can drive fluid out of the chamber. FIG. 1 shows the piston assembly 12 partially inserted into the syringe chamber and FIG. 2 shows the piston assembly fully inserted into the syringe chamber to deliver fluid to the tubing 41.

A housing 60 is located at the proximal end of the plunger assembly 12 and has a wall 62 defining a chamber 64 having an open end 66 which can be sealed by any suitable structure or material such as a cap or by a foil material 68. An optional annular flange 70 extends radially outwardly from the wall 62 and provides a surface upon which the sealing structure can be attached.

Figure 5:
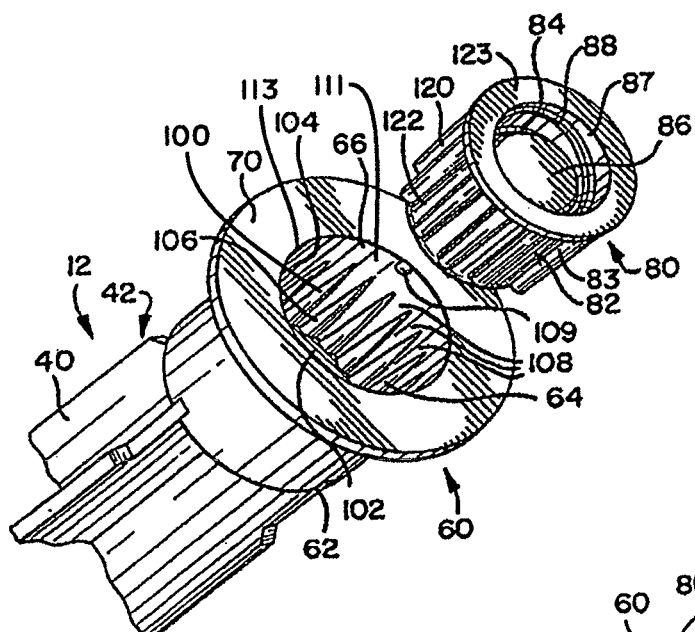
FIG. 5 is a perspective view assembly drawing of an antiseptic cap equipped plunger.
Figure 6:
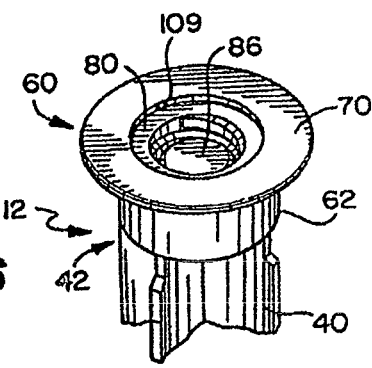
FIG. 6 is a perspective view of an antiseptic cap equipped plunger in a partially assembled state.

FIG. 5 shows a cap assembly 80 proximate the chamber 64 of the housing 60 and FIG. 6 shows the cap assembly 80 positioned within the chamber 64. In one preferred form of the invention, the cap assembly 80 has a cap 82 having a wall 83 defining a chamber 84 containing an absorbent material 86 such as a sponge. The sponge 86, in a preferred form of the invention, is wetted or soaked with an agent such as an antiseptic, anticoagulant or antimicrobial ("antiseptic solution") and can be selected from the locking and flushing solutions set forth below or the antiseptic solutions set forth below. The cap 82 has an interior surface 87 with a set of threads 88 for mating with a set of threads on the access site 38.

Figure 7:
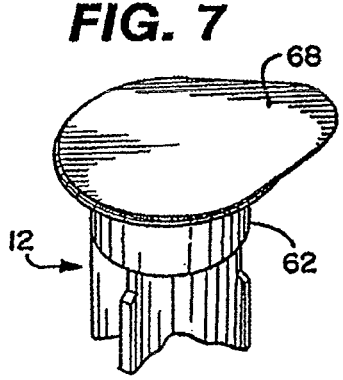
FIG. 7 is a perspective view of the antiseptic cap equipped plunger of FIG. 6 with a top seal.
Figure 8:
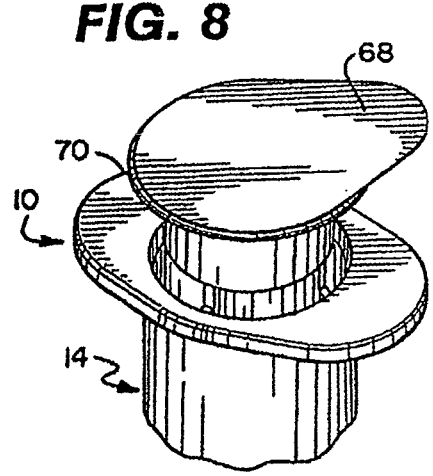
FIG. 8 is a perspective view of an antiseptic cap equipped plunger of FIG. 7 mounted in a lumen of a syringe barrel.
Figure 15:
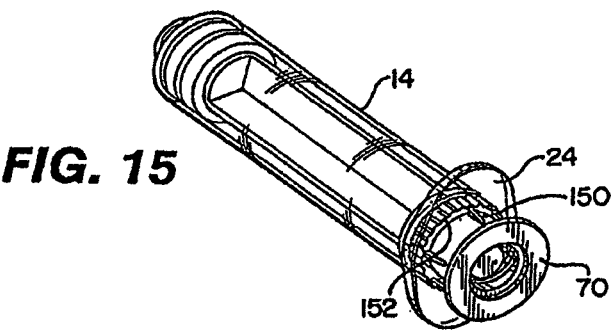
FIGS. 15-17 show various views of one embodiment antiseptic cap equipped plunger and syringe barrel assembly with a barrel lock to resist rotation of the plunger assembly with respect to the syringe barrel.
Figure 16:
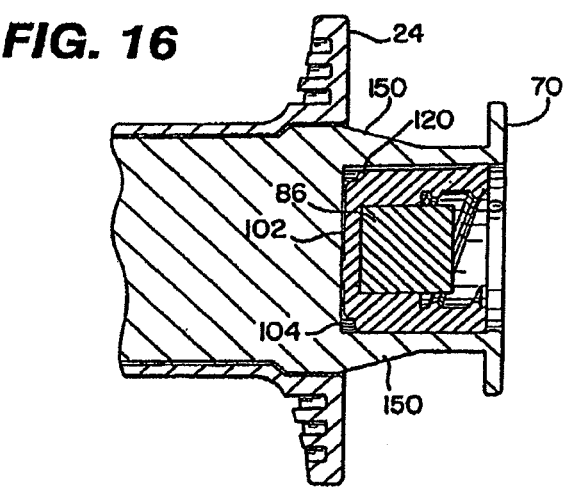
Figure 17:
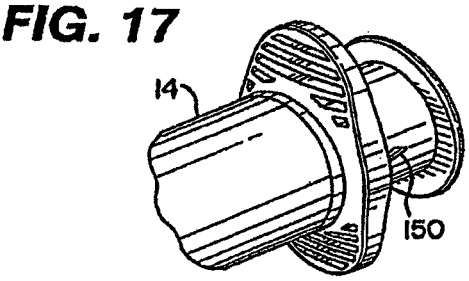

FIGS. 7 and 8 show the cap assembly 80 sealed with a foil material or lid stock material 68 which can be attached to the flange 70 by any suitable method such as by adhesives or by conductive or inductive heat sealing techniques. FIG. 7 shows the antiseptic cap piston assembly 12 and FIG. 8 shows the antiseptic cap equipped piston assembly 12 inserted into the chamber of the syringe barrel 14 to define the antiseptic cap equipped piston and syringe barrel assembly 10.

Figure 3:
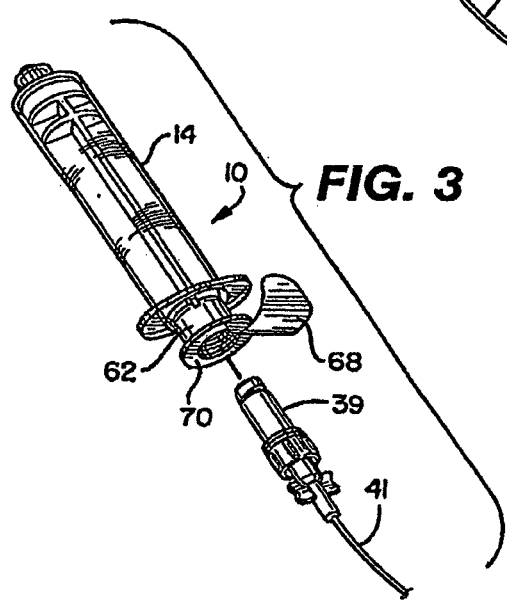
FIG. 3 is a perspective view of an antiseptic cap equipped plunger and syringe barrel assembly prior to connection of the antiseptic cap to an access point to a central venous catheter.
Figure 4:
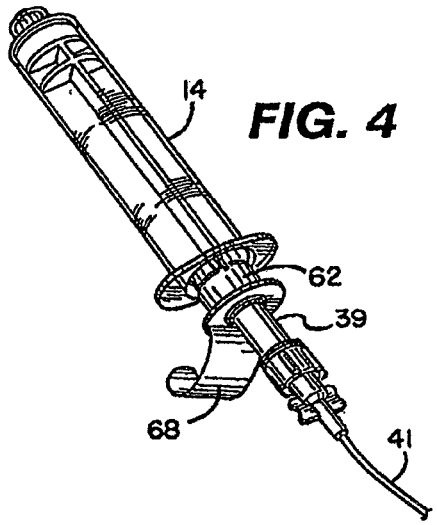
FIG. 4 is a perspective view of an antiseptic cap equipped plunger and syringe barrel assembly after connection of the antiseptic cap to an access point to a central venous catheter.

FIGS. 3 and 4 show one possible method for utilizing the cap assembly 80 by docking with the access device 38. FIG. 3 shows the lid stock 68 peeled away from the flange 70 and FIG. 4 shows docking the antiseptic cap assembly 80 to the valve 39. The syringe barrel is rotated clockwise or counterclockwise to engage the threads 88 of the antiseptic cap assembly 80 with the threads of the access site 38. After engagement, the syringe barrel 14 will be moved away from the access site 38 and the antiseptic cap assembly 80 will slide outward from the housing 60 and remain docked to the access site 38. The antiseptic cap assembly 80 can remain docked to the valve 39 of the access site 38 for any suitable period of time from a few minutes to numerous hours. When the antiseptic cap assembly 80 is docked to the valve 39 the tubing or catheter 41 is sealed to block the ingress into the catheter of pathogens and contaminants and a portion of the access site 38 is exposed to the antiseptic material in the sponge 86.

It is desirable that during the rotation of the syringe barrel that the antiseptic cap assembly 80 does not rotate with respect to the housing and/or optionally that the plunger assembly 12 does not rotate with respect to the syringe barrel 14 so that the threads 88 of the antiseptic cap can fully engage the threads of the access site. The present invention provides a mechanism associated with the assembly 10 for preventing the rotation of the antiseptic cap assembly 80 with respect to the plunger assembly 12 and more preferably a mechanism on either the plunger assembly or on the antiseptic cap 80 to prevent relative rotational movement between the antiseptic cap 80 and the plunger assembly 12. In an even more preferred form of the invention, the mechanism for preventing relative rotation of the antiseptic cap 80 with respect to the plunger assembly 12 has mating portions on both parts that when assembled cooperatively engage one another to prevent relative rotation. It is also contemplated that a separate mechanism, device or member could be used to lock the two parts together to achieve this purpose.

If a user of the assembly 10 grasps the assembly 10 by the antiseptic cap and plunger assembly 12 then the interlocking structures between the piston assembly 12 and the syringe barrel 12 would not necessarily be needed. Accordingly, FIGS. 5, 9-11 show exemplary structures for locking the antiseptic cap assembly 80 inside the housing 60 so that these parts rotate together and one part does not rotate in a direction or at a rate different from that of the other part. Further, FIGS. 15-18 show exemplary structures for interlocking the antiseptic cap plunger assembly 12 with the syringe barrel 14.

In one preferred form of the invention the housing 60 will have a feature or structure that forms an interference fit with an external surface 83 of the antiseptic cap 80. Even more preferably, an internal surface 63 of the side wall 62 of the housing 60 will have a feature or structure to form an interference fit with a portion of the antiseptic cap assembly 80. In another preferred form of the invention the antiseptic cap assembly 80 will have a feature to form an interference fit with the housing 60 and even more preferably the outer surface 83 of the antiseptic cap 80 will have a feature to contact the inner surface 63 of the housing side wall 62.

In another preferred form of the invention the plunger housing 60 and the cap assembly 80 each will have a feature or structure that cooperatively engage one another to prevent relative rotation of the cap assembly 80 and the housing 60. FIG. 5 shows one preferred form of the invention having a plurality of circumferentially spaced and axially extending ribs 100 on the internal surface 63 of the housing side wall 62 (internal ribs 100) for engaging the wall 83 of the antiseptic cap 82 to lock the cap assembly 80 in place to prevent rotation of the cap assembly 80 when positioned inside the housing 60. In a preferred form of the invention, the internal ribs 100 extend from a bottom wall 102 up to an intermediate height of the housing sidewall 62. In a preferred form of the invention the internal ribs 100 will have a height roughly equal to a height of the cap 82. A plurality of internal slots 108 are defined between each set of adjacent internal ribs 100. The internal ribs 100, in a preferred form of the invention, will have a width that tapers inwardly from proximate the bottom wall 102 to a top 104 of the internal ribs 100 so that the width of the internal ribs decrease from a bottom 106 of a rib to the top 104 of the rib. Also, it is preferable that the top of the internal ribs 100 have a generally arcuate profile to act as a lead-in during insertion of the antiseptic cap assembly 80 into the housing 60. In a preferred form of the invention, the internal ribs 100 will terminate short of a top 113 of the housing sidewall 62 to define an annular gap 111 between the top of the rib 104 and the top 113. Also, extending radially inwardly from the internal surface 63 of the cap 82 is a detent 109 positioned proximate a top portion 113 of the side wall 62.

The antiseptic cap 82 has a plurality of circumferentially spaced and axially extending ribs 120 extending along an external surface 122 of the cap 82 (external ribs 120) from an annular flange 123. The external ribs 120 are dimensioned for engaging a portion of the interior wall of the housing 62 to prevent relative rotation of the cap and the plunger assembly 14 and define a plurality of external slots one of each between each adjacent pair of external ribs. When the cap 82 is positioned within the chamber 64 (FIGS. 9 and 11) each of the external ribs 120 are positioned within an internal slot 108 and each of the internal ribs are positioned within an external slot to lock together these parts to assure that the cap rotates in the same direction as the plunger rod. FIGS. 6 and 11 also show that when the cap 82 is positioned within the housing 60, the detent 109 contacts the annular flange 123 to hold the cap in the housing to prevent or resist inadvertent dropping of the cap from the housing prior to docking of the cap with the access site. In one preferred form of the invention, the external ribs 120 are specifically designed in conjunction with internal slots 108 so that the antiseptic cap is guided out of the storage chamber 64 as the cap is screwed onto the threads of the access site.

FIGS. 12-14 show several embodiments of gripping surfaces on the housing 60 (with lid stock 68 removed) to facilitate use of the assembly 10 or the plunger assembly 12. FIG. 12 shows axially extending and circumferentially spaced protuberances 130 on an outer surface of the wall 62. The protuberances 130 can have numerous different cross-sectional shapes including circular, polygonal, oval and irregular and, in a preferred form of the invention, extend from the flange 70 to a bottom of the housing.

FIG. 13 shows a housing 60 that has no flange 70 and has protuberances 130 on the wall 62 extending substantially the entire height of the housing 60. FIG. 14 shows a housing 60 where the outer surface of the wall 62 is relatively smooth but has a series of circumferentially spaced and axially extending protuberances 130 on a circumferential edge of the flange 70.

As with the cap and plunger assembly rotational locking features or structures, the optional plunger assembly 12 and syringe barrel 14 locking feature or structure can be positioned alone on the plunger assembly 12, or alone on the syringe barrel 14 or have cooperating structures on both the plunger assembly 12 and the syringe barrel 14. It is also contemplated that a separate mechanism, device or member could be used to lock the two parts together to achieve this purpose.

FIGS. 15-18 show various embodiments for the optional feature of locking the plunger assembly 12 from rotational motion with respect to the syringe barrel 14. In one embodiment shown in FIGS. 15-17 and 21 a wing 150 extending axially along an outside surface of the housing side wall 62 engages a tooth 152 positioned on an interior surface of the syringe barrel at is proximal end. More preferably, the plunger assembly 14 will have more than one wing 150 with each wing being circumferentially spaced from the other. In an even more preferred form of the invention the plunger assembly will have four wings 150 spaced 90 degrees from one another. Also, in a more preferred form of the invention, the syringe barrel will have a plurality of circumferentially spaced teeth. When the plunger assembly is nearly fully inserted into the syringe barrel each of the wings will extend into a tooth to prevent rotation of the plunger assembly 12 with respect to the syringe barrel 14.

Figure 18:
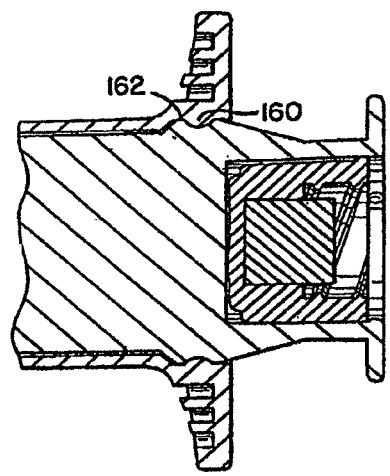
FIG. 18 shows another embodiment of a barrel lock to resist rotation of the plunger assembly with respect to the syringe barrel.

FIG. 18 shows another embodiment of a locking feature to prevent rotation of the plunger assembly 12 with respect to the syringe barrel 14 and also prevents relative translational motion of the parts. In this embodiment an annular protuberance 160 positioned on an interior surface of the syringe barrel at its proximal end 20 engages an annular detent 162 on an outside surface of the plunger rod.

Figure 19:
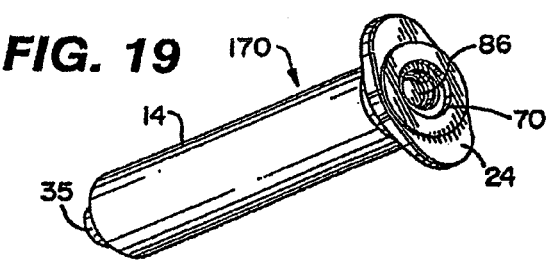
FIGS. 19-20 show various views of another embodiment antiseptic cap equipped plunger and anti-reflux syringe barrel assembly with a barrel lock to resist rotation of the plunger assembly with respect to the syringe barrel.
Figure 20:
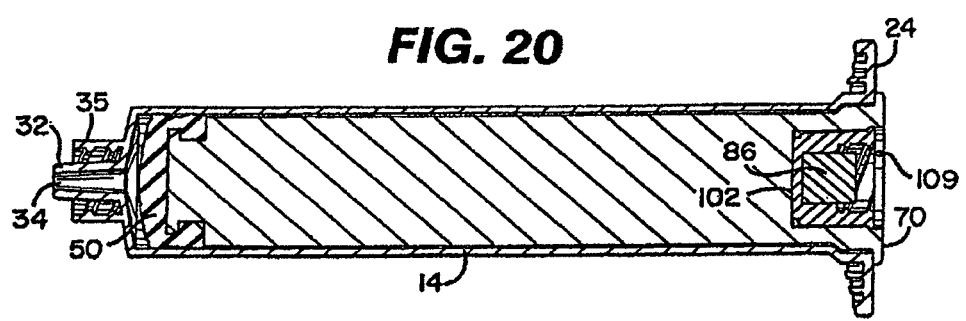
Figure 21:
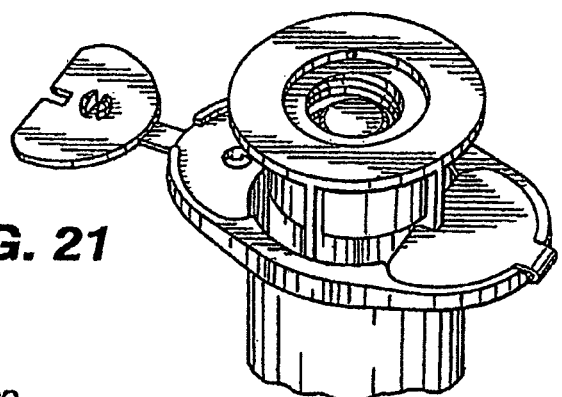
FIG. 21 shows a perspective view of another embodiment antiseptic cap equipped plunger and syringe barrel assembly with a barrel lock to resist rotation of the plunger assembly with respect to the syringe barrel.

FIGS. 19 and 20 show an antiseptic cap equipped plunger assembly 12 and non-refluxing syringe assembly 170. Non-refluxing syringes are well known in the art and there are numerous methodologies for reducing reflux while accessing the access site of a central venous catheter. In this embodiment the annular flange 70 of the plunger assembly 12 abuts the flange 24 of the syringe barrel prior to the piston 50 contacting an interior surface of the syringe distal end wall 30.

Figure 22A:
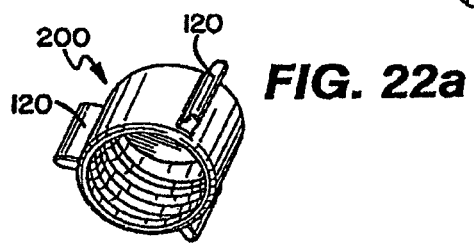
FIGS. 22a,b are respectively a perspective view of an antiseptic cap without a sponge and with a sponge.
Figure 22B:
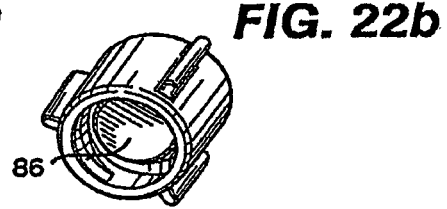
Figure 23:
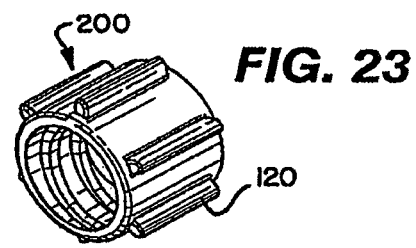
FIGS. 23 and 24 are different embodiments of the antiseptic cap with varying gripping features.
Figure 24:
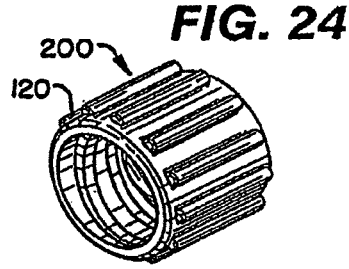

It is contemplated that the antiseptic cap assembly 80 of the present invention need not be coupled or combined with a plunger or a syringe barrel. FIGS. 22a, b show a stand-alone antiseptic cap assembly 200 having three circumferentially spaced ribs 120 for grasping by the hand of a user of the cap assembly. FIG. 22a shows the cap 82 without an absorbent material 86 and FIG. 22b shows the cap with an absorbent material. The cap 200 can be used for the same purposes of the cap assembly 80 described above but will be used by hand. All other features of the cap 200 are essentially the same as described above with the exception that the cap 200 does not have to be dimensioned to fit within a chamber carried by a syringe plunger. FIGS. 23 and 24 show varying frequency of ribs 120 and varying shapes and sizes.

Figure 25:
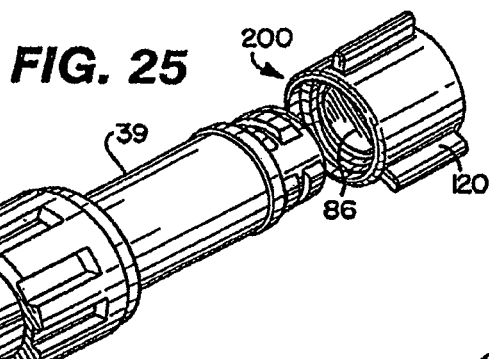
FIG. 25 is a perspective view of the antiseptic cap of FIG. 22b prior to docking with a valve.
Figure 26:
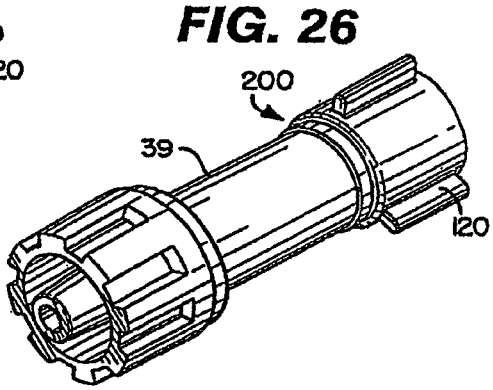
FIG. 26 is a perspective view of the antiseptic cap of FIG. 22b docked with a valve.
Figure 27:
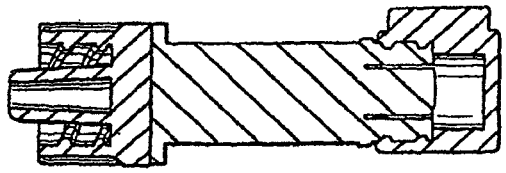
FIG. 27 is a side view in cutaway of the antiseptic cap and valve assembly shown in FIG. 26.

FIG. 25 shows the cap 200 proximate the access site 38 and FIGS. 26 and 27 show the cap 200 docked to the access site 38.

Figure 28:
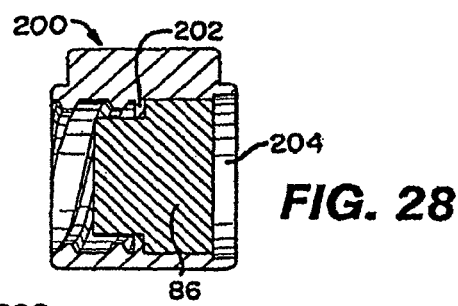
FIGS. 28-30 are side views in cutaway of two different embodiments of the antiseptic cap.

A suitable absorbent material 86 includes medical grade materials capable of storing and releasing an antiseptic liquid, or liquid having other medical purposes, and includes materials such as sponges, rupturable capsules and other materials or devices capable of serving this purpose. Suitable sponges can include any sponge suitable for use for medical purposes and can be naturally occurring or synthetic. The sponges can be die cut into suitable shapes or can be molded into the desired shape. It is desirable that the sponge 86 be attached to the antiseptic cap 82 to prevent the sponge 86 from inadvertently falling out of the cap 82. FIG. 28 shows the sponge 86 is captured between an annular wall 202 and a disc 204 attached to the cap 82 by any suitable method such as ultrasonic or vibrational welding or other techniques well known in the art.

Figure 29:
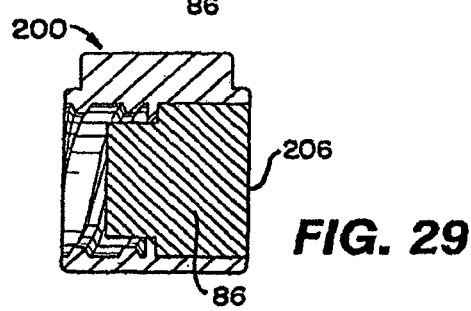
Figure 30:
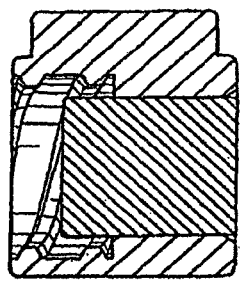

FIGS. 29 and 30 show a variation on the cap assembly 200 of FIG. 28. In this embodiment, the sponge is retained in the cap 82 with a plastic sheet 206 heat welded to the cap. In one preferred form of the invention the sponge is attached by an adhesive or by other method to form an assembly which is then attached to the cap.

Figure 31A:
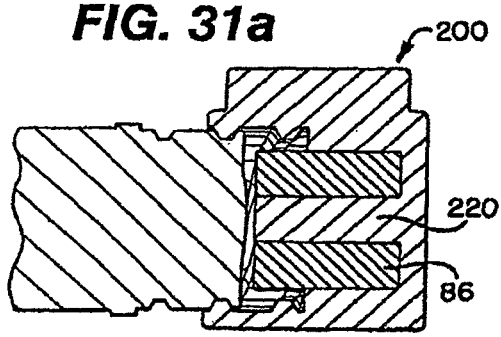
FIGS. 31 a,b are, respectively, side views in cutaway showing an antiseptic cap with a centrally disposed actuation post mounted on a valve with the valve in the unactivated and activated positions.
Figure 31B:
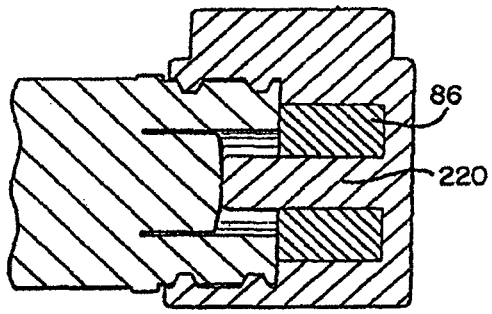

FIGS. 31 a, b show the cap 200 having a coaxially disposed and axially extending actuating post 220 circumferentially surrounded by a sponge 86 having a centrally positioned hole to fit over the post 220. FIG. 31a shows the cap 200 in initial engagement with the access site 38 and FIG. 31b shows the cap threaded onto the access site 38 and the actuating post opens the valve 39 and antiseptic fluid is allowed to flow into the valve.

Figure 32:
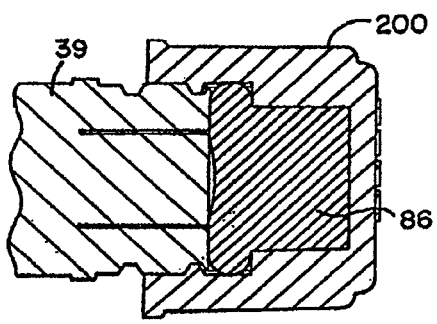
FIGS. 32 and 33 are side views in cutaway showing two different embodiments of an antiseptic cap having a molded sponge.
Figure 33:
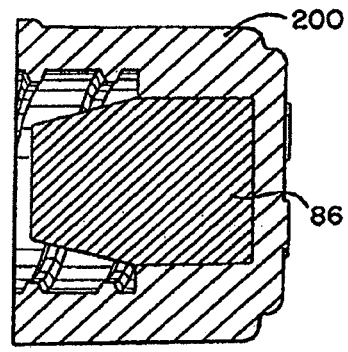
Figure 34:
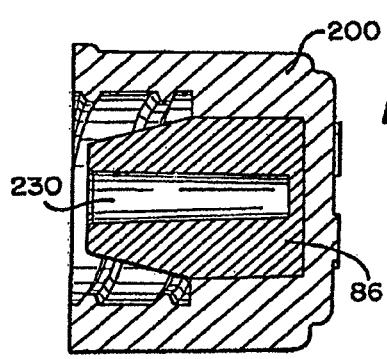
FIG. 34 is a side view in cutaway showing another embodiment of an antiseptic cap having a molded sponge docked to a valve.
Figure 35:
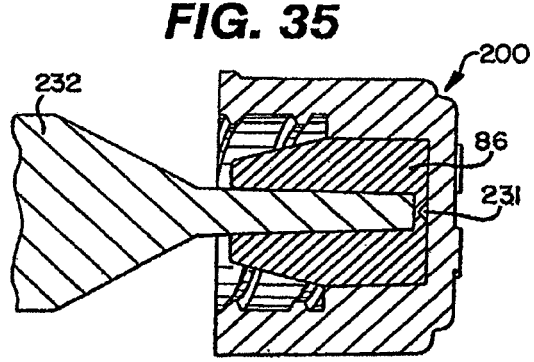
FIG. 35 is a side view in cutaway showing a step of attaching a molded sponge to an antiseptic cap.
Figure 36:
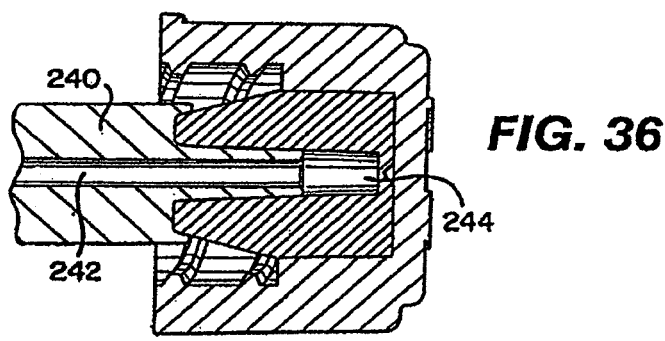
FIG. 36 is a side view in cutaway showing a step of delivering an antiseptic compound to a molded sponge positioned within a cap.

FIGS. 32-34 show varying shaped sponges that, in one preferred form of the invention, were molded into various desirable shapes. The sponge of FIG. 34 has a central opening 230 to facilitate attaching the sponge to the cap and to filling the sponge with antiseptic, anticoagulant or other suitable fluids set forth above. FIG. 35 shows the cap having a centrally disposed energy director 231, an ultrasonic welder 232 being brought into cooperative engagement with the sponge on a side of the sponge opposite the energy director 231. By applying ultrasonic energy the energy director 231 melts and attaches the sponge to the cap. FIG. 36 shows a filling device 240, having a lumen 242 and a dispensing head 244 in fluid communication with a source of antiseptic, anticoagulant or the like for dispensing a metered amount of such fluid into the interior portion of the sponge.

Figure 37:
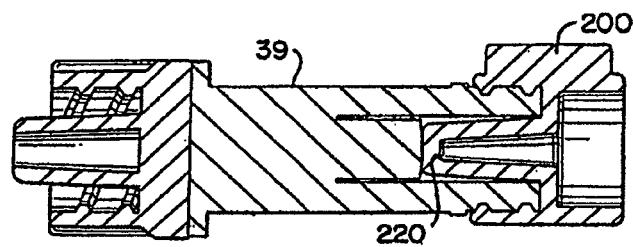
FIG. 37 shows a side view in cutaway of an antiseptic cap docking to a valve with the antiseptic cap having an antiseptic coating.

FIG. 37 shows an alternative embodiment of the antiseptic cap 200 where the sponge is replaced by an antiseptic coating on the actuating post 220.

Figure 38:
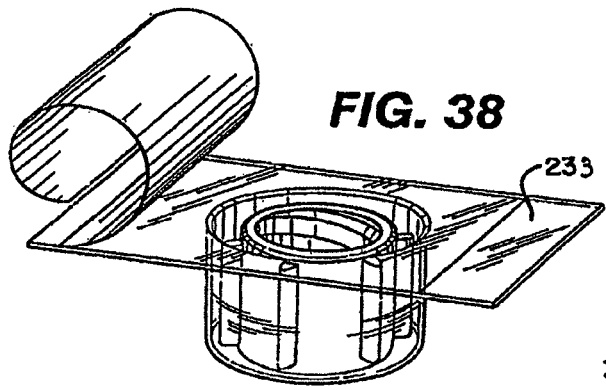
FIG. 38 shows a perspective view of an antiseptic cap in a blister package.

FIG. 38 shows the antiseptic cap 200 positioned in a blister pack 233 prior to sealing the blister pack.

Figure 39:
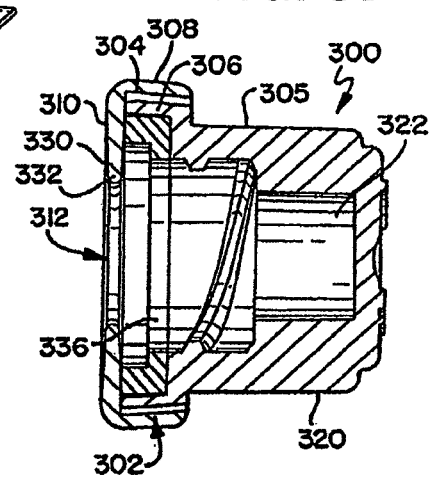
FIG. 39 is a side cross-sectional view of an antiseptic cap with a thread cover.

FIG. 39 shows an antiseptic cap 300 with a thread cover 302. The thread cover 302 can be part of any of the antiseptic caps discussed herein. The thread cover 302 is made of a deformable material capable of flexing upon application of moderate force applied by hand. In one preferred form of the invention the thread cover 302 is made from a polymeric containing material and more preferably a polymeric material having a modulus of elasticity of less than 20,000 psi. In another preferred form of the invention the polymeric material will be an elastomer or plastomer or like material. The thread cover 302 enhances the connection between the antiseptic cap 300 and a device such as a valve or other access devices 38. The thread cover 302 provides a physical barrier to the ingress of pathogens, dust or other contaminants through the mating threads of the antiseptic cap 300 and the access device or valve to which it is docked. The thread cover 302 also serves to retain antiseptic fluids from the antiseptic cap 300 from leaking out through the threads. The thread cover can be made a part of the antiseptic cap 300 using techniques well known in the art such as overmolding, or by attaching as a separate part using welding techniques such as heat conductive welding, heat induction welding, vibrational welding, stretch or friction fit, or by using a suitable adhesive.

The thread cover 302 can provide a universal fit to most commercially available valves, connectors and access devices, or the thread cover 302 can be customized to dock with a particular access device.

FIG. 39 shows, as is described above, the antiseptic cap 300 has an annular wall 305 having a first end 306 and a second end 320 with the first end having a greater diametrical dimension than the second end. The annular wall defines a central chamber 322 having an open end 323. In one preferred form of the invention, the chamber 322 will have a sponge 86 positioned therein as shown in FIGS. 5 and 6 above, although it is not shown in FIG. 39. The thread cover 302 is shown attached by an optional bonding layer 304 to the first end 306 of the annular wall 305. The thread cover 302 has a first leg 308 and a second leg 310. The first leg 308 extends parallel to the annular wall 305 and the second leg 310 extends radially inwardly from the annular wall 305 in a direction transverse to the first leg 308 and across a portion of the open end 323 and defines a central opening 312, having a reduced diameter when compared to the open end 323, into the chamber 322. The second leg 310 terminates at a distal end 330 with a rounded outer surface 332.

Figure 40:
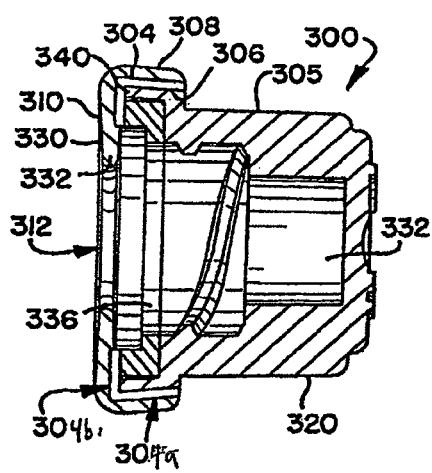
FIG. 40 is a side cross-sectional view of an antiseptic cap with a thread cover.

FIG. 40 shows an alternative embodiment of the antiseptic cap 300 having the thread cover 302 having both the first and second legs 308, 310 attached to the first end 306 of the annular wall 305 through bonding layers 304 a,b. A top surface 340 of the first end 306 is shown having the same thickness or diametrical dimension as the remainder of the first end but it is contemplated the top surface could have a radially extending flange 123 as shown in FIG. 5.

Figure 41:
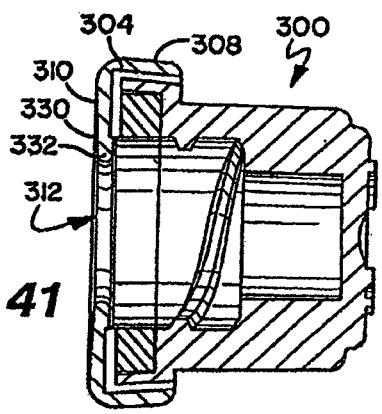
FIG. 41 is a side cross-sectional view of an antiseptic cap with a thread cover.

FIG. 41 shows an alternative embodiment of the antiseptic cap 300 that differs from the antiseptic cap shown in FIGS. 39 and 40 by not including a counterbore 336 shown in these figures. The counterbore 336 provides a chamber of reduced diameter and, therefore, will form a tighter fit with access devices with a narrower outer diameter when compared to the cap shown in FIG. 41 which does not include the counterbore. This is just one example of the modifications that can be made to the geometry of the antiseptic cap to enhance the connection between the cap and an access site.

Figure 42A:
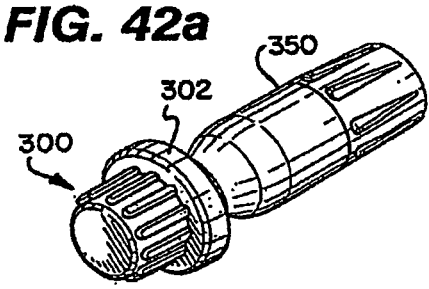
FIGS. 42a,b are perspective front and back views of an antiseptic cap with a thread cover connected to a Cardinal SMART SITE access site.
Figure 42B:
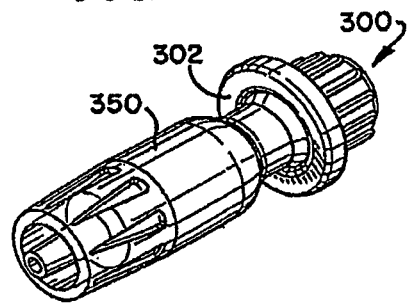
Figure 43A:
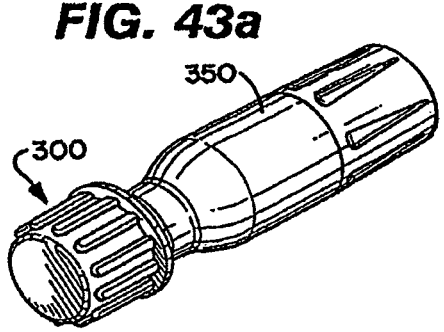
FIGS. 43 a,b are perspective front and back views of an antiseptic cap without a thread cover connected to a Cardinal SMART SITE access site.
Figure 43B:
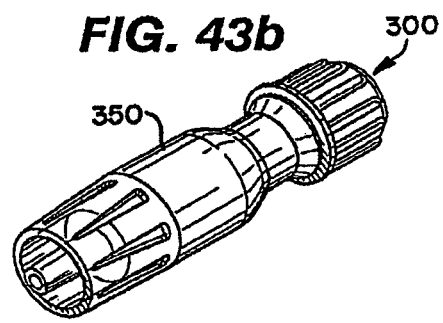

FIGS. 42a,b show front and back views of the antiseptic cap 300 with the thread cover 302 connected to a Cardinal SMART SITE access site 350. FIGS. 43 a,b are perspective front and back views of the antiseptic cap without the thread cover 302 connected to the Cardinal SMART SITE access site.

Figure 44A:
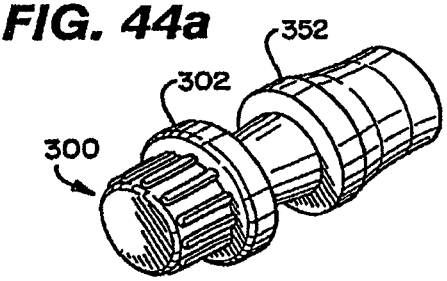
FIGS. 44 a,b are perspective front and back views of an antiseptic cap with a thread cover connected to a Hospira (ICU) C1000 Clave access device.
Figure 44B:
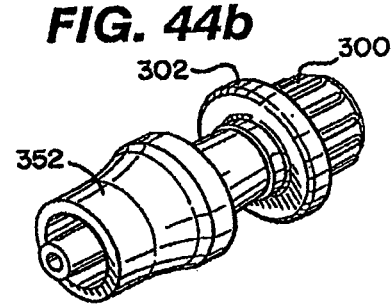
Figure 45A:
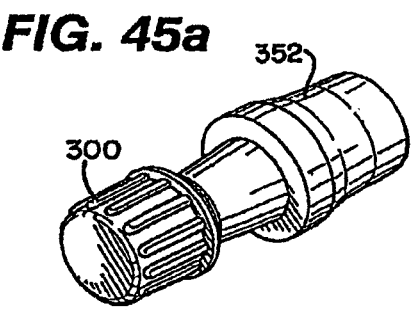
FIGS. 45 a,b are perspective front and back views of an antiseptic cap without a thread cover connected to a Hospira (ICU) C1000 Clave access device.
Figure 45B:
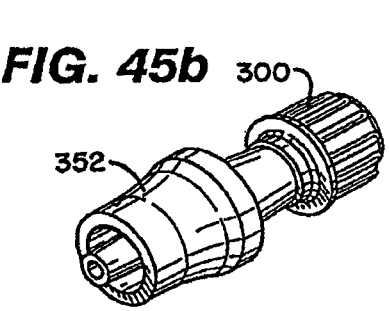

FIGS. 44a,b are perspective front and back views of the antiseptic cap 300 with the thread cover 302 connected to a Hospira (ICU) C1000 Clave access device 352. FIGS. 45a,b are perspective front and back views of the antiseptic cap, without a thread cover 302, connected to the Hospira (ICU) C1000 Clave access device.

Figure 46A:
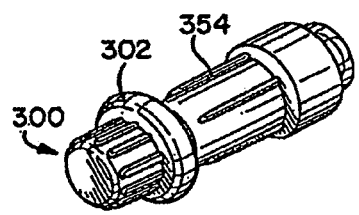
FIGS. 46 a,b are perspective front and back views of an antiseptic cap with a thread cover connected to a B. Braun ULTRASITE access device.
Figure 46B:
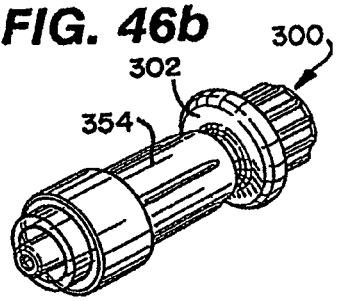
Figure 47A:
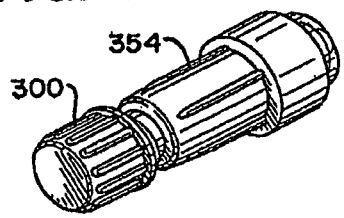
FIGS. 47 a,b are perspective front and back views of an antiseptic cap without a thread cover connected to a B. Braun ULTRASITE access device.
Figure 47B:
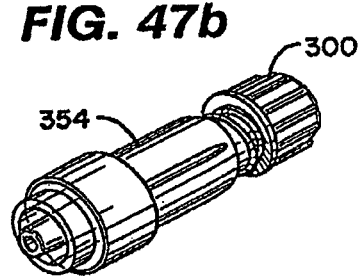

FIGS. 46a,b are perspective front and back views of the antiseptic cap 300 with the thread cover 302 connected to a B. Braun ULTRASITE access device 354. FIGS. 47a,b are perspective front and back views of the antiseptic cap without the thread cover 302 connected to the B. Braun ULTRASITE access device.

Figure 48A:
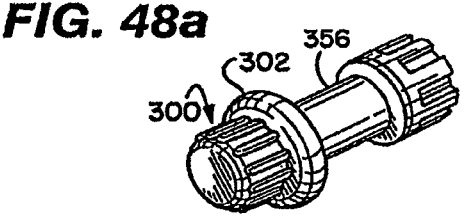
FIGS. 48 a,b are perspective front and back views of an antiseptic cap with a thread cover connected to a Rymed INVISION PLUS access device.
Figure 48B:
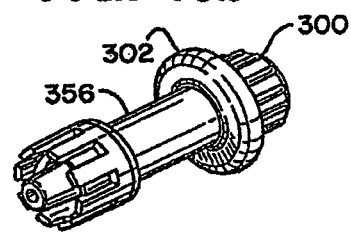
Figure 49A:
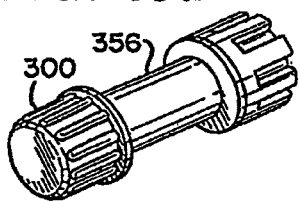
FIGS. 49 a,b are perspective front and back views of an antiseptic cap without a thread cover connected to a Rymed INVISION PLUS access device.
Figure 49B:
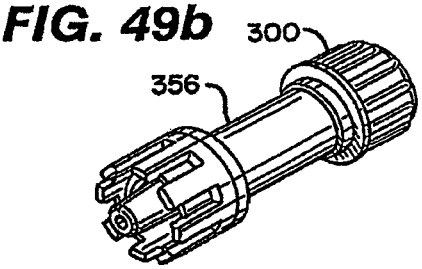

FIGS. 48a,b are perspective front and back views of the antiseptic cap with the thread cover 302 connected to a Rymed INVISION PLUS access device; 356. FIGS. 49a,b are perspective front and back views of the antiseptic cap without the thread cover 302 connected to a Rymed INVISION PLUS access device.

Figure 50:
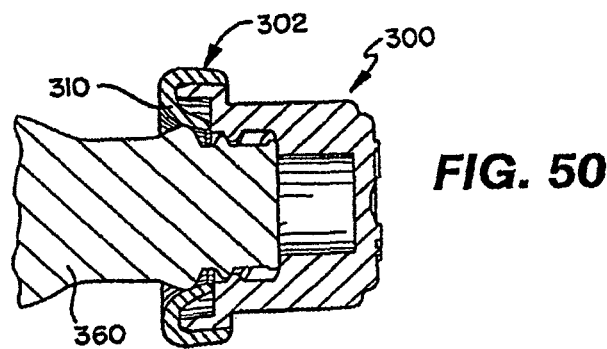
FIG. 50 is a side cross-sectional view of an antiseptic cap with a thread cover connected to a Cardinal SMARTSITE PLUS access device.
Figure 51:
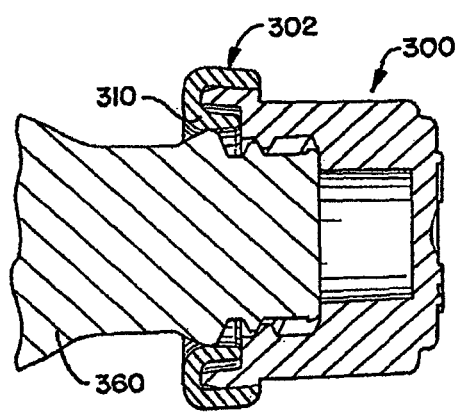
FIG. 51 is a side cross-sectional view of an antiseptic cap with a thread cover connected to a Cardinal SMARTSITE PLUS access device and the thread cover having a reduced diameter when compared to the thread cover shown in FIG. 50.
Figure 52:
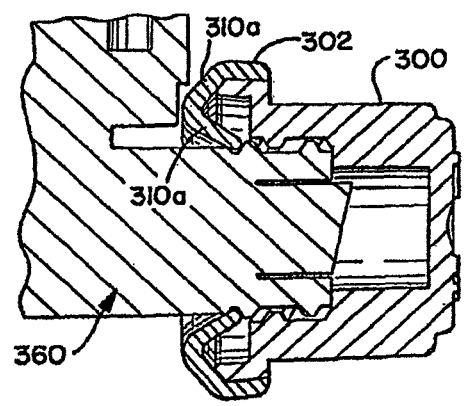
FIG. 52 is a side cross-sectional view of an antiseptic cap with a thread cover connected to a Hospira (ICU) C1000 Clave access device having a thread cover with an alternative profile.

FIGS. 50-52 show various embodiments of the thread cover 302. FIG. 50 differs from FIG. 51 in that the second leg 310 extends farther across the opening of the chamber in FIG. 51 than shown in FIG. 50. FIG. 52 shows another embodiment of the thread cover 302 having a segmented second leg 310a,b. This embodiment may be desirable to provide a more effective seal for certain access devices.

FIG. 53 shows an exploded view of an alternative embodiment 400 of the syringe barrel assemblies 10, discussed above, incorporating a cap holder 402 into the system of parts. Thus, the alternative assembly and system 400 has an antiseptic cap and cap holder equipped plunger assembly 12', a syringe barrel 14, an antiseptic cap 82 (shown with an optional thread cover 302), an absorbent material 86, and peelable lid stock 68. FIG. 54 shows an exploded view of an antiseptic cap holder assembly 404 including the cap holder 402 with the antiseptic cap assembly 80 positioned within a chamber 406 of the cap holder 402. This embodiment 400 allows for the separate manufacture, assembly, and sterilization of the assembly 400 from the plunger assembly and the syringe barrel.

The cap holder 402 has a proximal and distal ends 408, 410, and an inner wall surface 412 and an outer wall surface 414, an opening 416 into the chamber 406, and a radially outwardly extending flange 418 circumjacent the opening 416 and extending from the proximal end 408 of the cap holder 402. The cap holder 402 will also have an optional bottom wall 419.

In a preferred form of the invention, the cap holder 402 or the antiseptic cap 82 will have a structure, element or the like that prevents the relative rotation of the cap holder 402 and the antiseptic cap 82 until the antiseptic cap assembly 80 is securely docked to the access device 38. Also, in a preferred form of the invention the cap holder 402 or the plunger assembly 12' will have a structure, element or the like for preventing the relative rotation of the cap holder 402 and the plunger assembly 12' until the antiseptic cap assembly 80 is securely docked to the access device 38. Any of the anti-rotation devices discussed above to stop the rotation of the antiseptic cap assembly 80 with the plunger assembly 12 would be suitable for, these purposes. Also, it is contemplated the devices discussed above in reference to FIGS. 15-21 to prevent the relative rotation of the plunger assembly 12 and the syringe barrel 14 could be incorporated into this embodiment 400.

FIG. 53 shows the inner wall surface 412 of the cap holder 402 carries the internal ribs 100 and the internal slots 108 that interact with the external ribs and external slots 120, 122 of the cap 82 as is described above with respect to FIG. 5. These structures prevent or resist the relative rotation of the cap holder 402 with respect to the antiseptic cap assembly 80. The term "ribs" referred to herein are structures that are raised or extend outward from a surface. The term "slots" refer to structures that extend below a surface or is defined between two ribs and is at a lower level than the ribs.

FIG. 53 also shows an interlocking structure for preventing the relative rotation of the cap holder 402, or the cap holder assembly 404, with respect to the plunger assembly 12'. The outer wall surface 414 has a plurality of circumferentially spaced and axially extending ribs 420 defining slots 424 between each pair of adjacent ribs. In a preferred form of the invention, the ribs 420 are generally triangular in shape having a base portion 426 and an apex portion 428. The slots 424 are oppositely-oriented triangularly shaped areas having slot base portions 430 extending between two adjacent rib apex portions 428 and slot apex portions 432 separating adjacent rib base portions 426. On the internal wall surface 63 of the plunger chamber 64 are similarly shaped plunger ribs 434 and plunger slots 436. The ribs 420 are dimensioned to fit within the plunger slots 436 and the slots 424 are dimensioned to fit over and receive the plunger ribs 434. Thus, when the cap holder 402 or the cap holder assembly 404 is inserted in the plunger chamber 64 the cap holder ribs 420 are interdigitated with the plunger ribs 434 to prevent or resist the relative rotation of the cap holder 402, or cap holder assembly 404, with respect to the plunger assembly 12'.

In yet another preferred form of the invention, the cap holder 402, the cap holder assembly 404 or the plunger assembly 12' will have a structure, element or the like that resists the relative axial movement of these parts when the cap holder 402 or the cap holder assembly 404 is positioned fully within the plunger assembly 12'. In one preferred form of the invention the cap holder 402 has an annular protuberance 440 that is dimensioned to fit within an annular groove 442 on the inner wall surface 414 of the cap holder and preferably extends in line with the base portions of the plunger ribs 434. A second locking structure is provided having a plurality of teeth 450 which extend axially outward from the outer wall surface 414 of the cap holder and are positioned in slots 424. In a preferred form of the invention the teeth extend axially outwardly to a height beyond the height of the ribs 434. The teeth 450 can be positioned in one or more of the slots or in each of the slots 424 or in alternating slots or, as is shown, circumferentially spaced 90° from one another. The teeth 450 preferably are positioned at an intermediate portion, between the base and the apex, of a slot 424. The teeth 450 are dimensioned to fit within a segmented annular groove 452 that extends circumferentially about the inner surface 412 crossing through the plunger ribs 434 at an intermediate portion, between the base and the apex, of the plunger ribs 434.

Figure 56A:
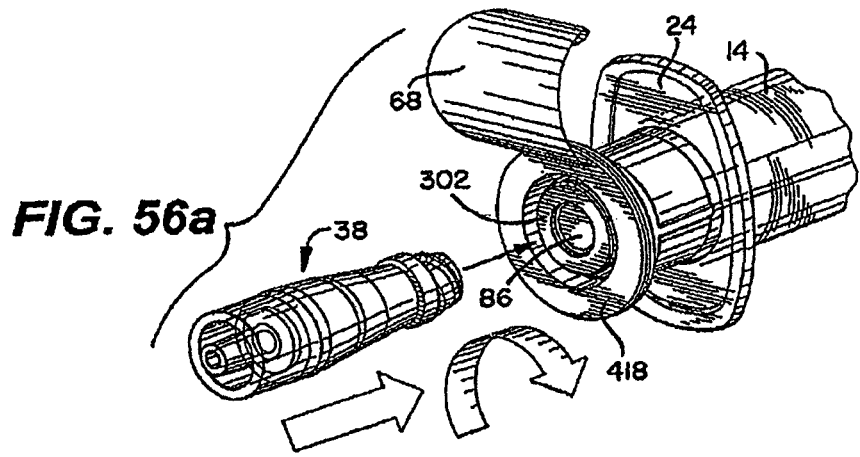
FIG. 56a is a perspective view of a medical access device adjacent an antiseptic cap equipped plunger and syringe barrel assembly with a lid stock peeled back in preparation for docking.
Figure 56B:
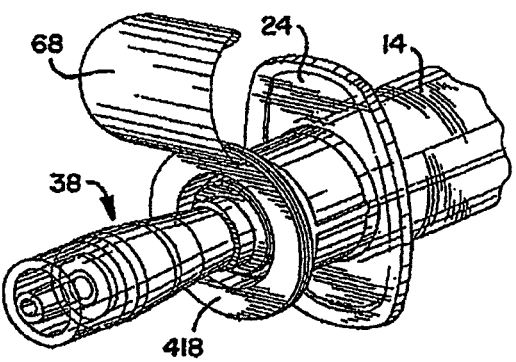
FIG. 56b is a perspective view of a medical access device docked to an antiseptic cap equipped plunger and syringe barrel assembly.
Figure 56C:
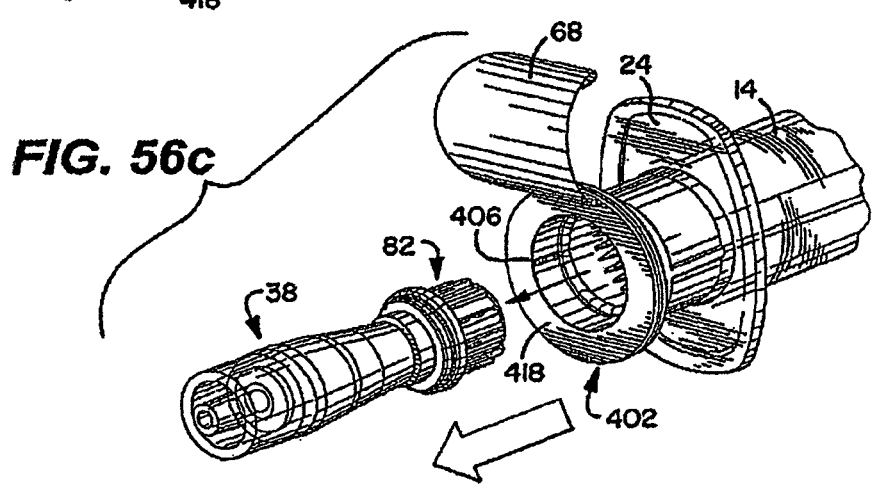
FIG. 56c is a perspective view of a medical access device docked to an antiseptic cap adjacent a plunger and syringe barrel assembly.
Figure 57:
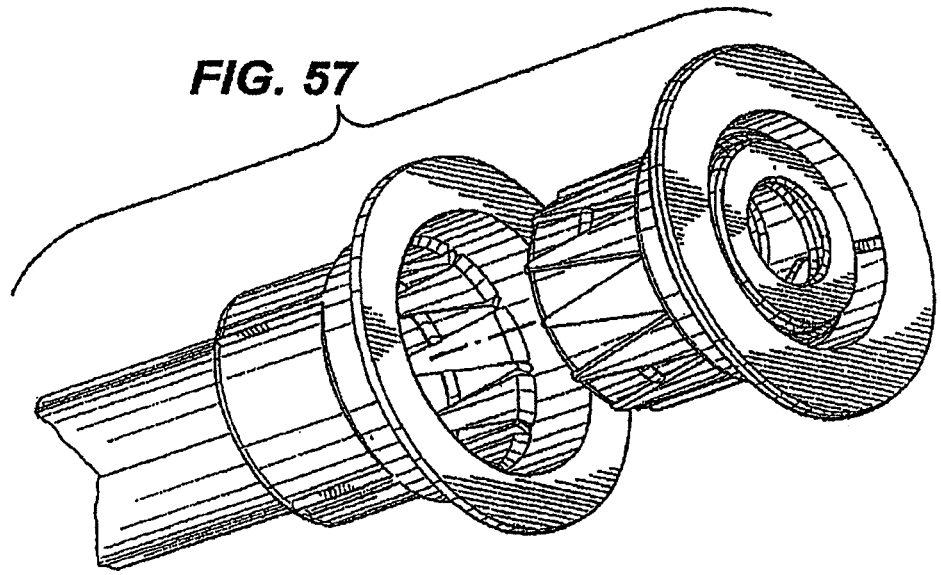
FIG. 57 is an enlarged view of a cup holder and antiseptic cap assembly adjacent an open and empty chamber of a syringe plunger.
Figure 58:
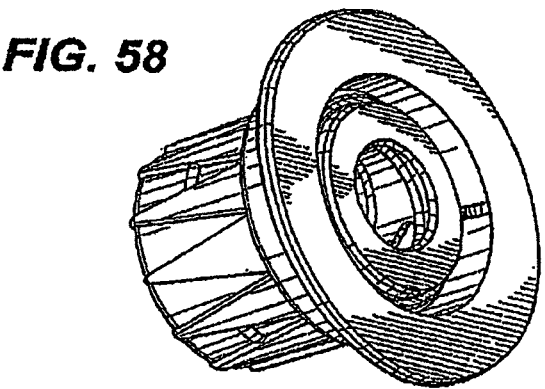
FIG. 58 is an enlarged view of a cup holder and antiseptic cap assembly positioned within a chamber of a syringe plunger.

FIGS. 56a,b,c respectively show the assembly 400 in a ready-for-use position, docked position, and used position. The assembly 400 is used in essentially the same fashion as described above with respect to FIGS. 3 and 4 except that when the assembly 400 is in the used position the cap holder 402 remains in the plunger assembly 12'.

The syringe barrel and plunger can be fabricated from any material suitable for its purpose and includes glass and polymeric material. Suitable polymeric materials include, but are not limited to, homopolymers, copolymers and terpolymers formed from monomers such as olefins, cyclic olefins, amides, esters, and ethers. The polymeric material may be a blend of more than one polymeric material and can be a monolayer structure or a multilayer structure. In one preferred form of the invention the syringe barrel and the plunger are injection molded from a polypropylene material.

Figure 59:
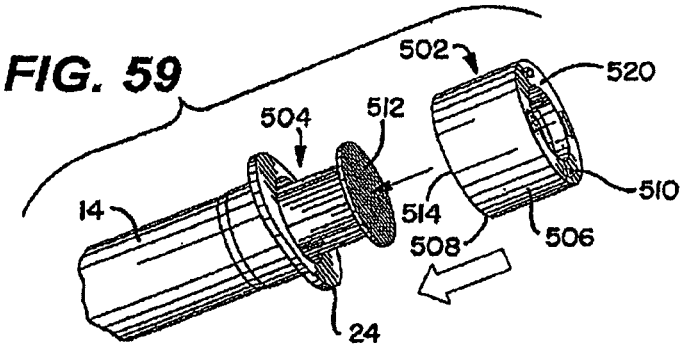
FIG. 59 is a perspective view of an alternative embodiment of an antiseptic cap assembly adjacent a syringe plunger and barrel assembly.
Figure 60:
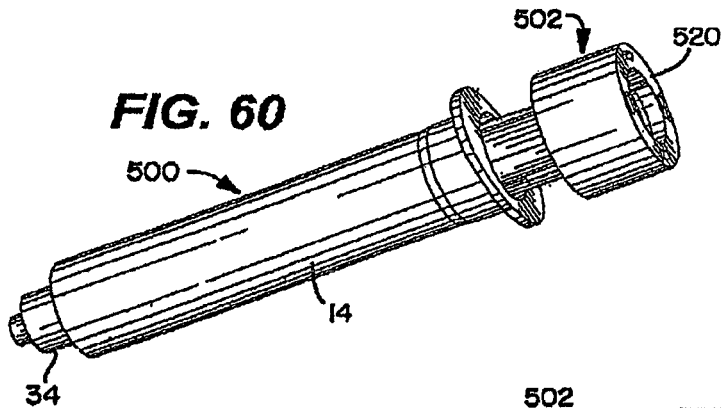
FIG. 60 is a perspective view of an alternative embodiment of an antiseptic cap assembly docked to a syringe plunger and barrel assembly.
Figure 61:
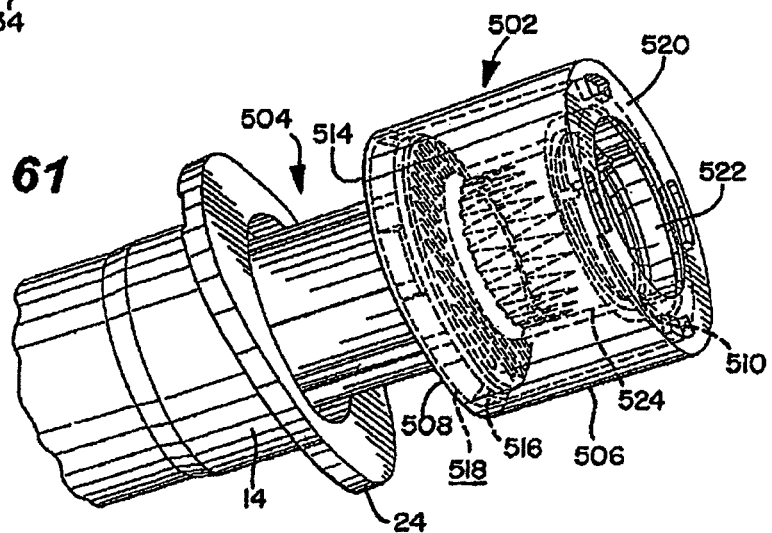
FIG. 61 is a perspective view of an alternative embodiment of an antiseptic cap assembly docked to a syringe plunger and barrel assembly with an outer wall being transparent to reveal interior portions of the assembly.

FIGS. 59-61 show a third embodiment 500 of an antiseptic cap equipped syringe plunger and barrel assembly with the antiseptic cap assembly 80 and lid stock 68 removed for clarity. The third embodiment 500 provides for retrofitting an antiseptic cap assembly 502 to a standard plunger 504. The antiseptic cap 502 has a first generally cylindrical outer wall 506 having a proximal end 508 and a distal end 510. The proximal end 508 is removably or fixedly attached to a button 512 of the plunger 504. The proximal end has an opening 514 dimensioned to fit about the button 512 and has a member for attaching to the button. In one preferred form of the invention, the attaching member includes a plurality of circumferentially spaced, and axially inwardly directed tabs 516 extending from an inner wall surface 518 and the tabs engage a lower surface of the button 512 to attach the antiseptic cap assembly 502 to the plunger 504.

The distal end of the antiseptic cap 502 has a top annular flange 520 extending radially inwardly from the first cylindrical wall 506 and defines a generally circular opening 522. A second cylindrical wall 524 extends axially downwardly from the top annular flange 520 and is coaxially disposed within the first cylindrical wall 506. When the antiseptic cap 502 is attached to the plunger button 512 a bottom peripheral edge of the second cylindrical wall 524 will abut a top surface of the plunger button 512 thereby capturing, by oppositely directed axially forces, the plunger button 512 between the tabs 516 and the second cylindrical wall. It is contemplated, however, that a second set of tabs could be provided spaced axially away from the first set of tabs and the piston button 512 could be trapped between the two sets of tabs. Further, it is contemplated other attaching means could be used that are well known in the art and the attaching member shown is merely exemplary.

The second cylindrical wall 524 defines a chamber as is shown in greater detail in FIG. 5 above with the ribs and slots as described for engaging the antiseptic cap assembly 80 to prevent relative rotational movement and to resist relative axial movement of the parts when the antiseptic cap assembly 80 is fully inserted into the chamber. Further, it is contemplated adapting the plunger and syringe as described above to prevent or resist the relative rotational movement of the plunger with respect to the barrel.

The piston 50 can be formed from any suitable material including a polymeric material or a silicone material. The stopper can be selected from a material with a desired durometer so that reflux is reduced when the stopper engages an inner surface of the distal end wall of the syringe barrel.

Suitable locking and flush solutions include a lower alcohol selected from ethanol, propanol and butanol. The locking solution can be a single lower alcohol or a blend of lower alcohols.

Suitable locking solutions can also include a lower alcohol with an antimicrobial and/or an anticoagulant. Suitable locking solutions can contain at least one lower alcohol in a range from 1% to 99% by volume and at least one other anti-microbial and/or anti-coagulant compound in a range from 1% to 99% by volume. The lower alcohol will usually be in aqueous solution, typically at 1% to 99% by volume, usually from 5% to 95% by volume. The at least one other anti-microbial is selected from the group consisting of taurolidine and triclosan, and the at least one anti-coagulant is selected from the group consisting of riboflavin, sodium citrate, ethylene diamine tetraacetic acid, and citric acid.

In one preferred form of the invention, the syringe assembly 10 will be pre-filled with one of the locking solutions and will be packaged by a manufacture and shipped to a health care provider. A cannula or needle will be attached to the distal end of the barrel and placed into fluid communication with the fluid access site of an indwelling central venous catheter. The flush solution will be injected into the catheter to clean or lock the catheter. Afterwards, the cap assembly 80 will be removed from the plunger 17 and the cap will be docked to the fluid access site of the catheter.

Citrate Salt Containing Antiseptic Solutions

In one form, the antiseptic is a solution a citrate salt and in another form of the invention the citrate salt solution is a hypertonic solution. The term hypertonic is used herein to refer to a fluid having an osmotic concentration and a density greater than the osmotic concentration and density of the blood of the patient. The antiseptic solution preferably comprises a citrate salt with a concentration range, in weight percent, of from about 1.5% to about 50% with an osmolality of about 300 to about 6400 mOsm. More preferably, the antiseptic solution comprises citrate salt in a concentration range of from about 10% to about 40%, yet more preferably, in a concentration range of from about 20% to about 30%.

In a preferred embodiment, the antiseptic solution is prepared to have a pH lower than that of the pH of the patient's blood. The citrate salt solution may be prepared to have a pH lower than about 6.5, more preferably, from about 4.5 to about 6.5. Also, the citrate salt solution can include pharmaceutically acceptable agents such as sodium chloride and sodium heparin. The citrate salt solution can also include a variety of other antibacterial, antimicrobial and anticoagulant agents such as gentamicin, vancomycin, and mixtures of these agents. Additional anticoagulant agents include, for example heparin, urokinase, tissue plasminogen activation (tPA) and mixtures of these agents.

By "pharmaceutically acceptable," it is meant that the citrate salt solution and the included salts and other additives which are, within the scope of sound medical judgment, suitable for use in contact with tissues of humans and lower animals without undue toxicity, irritation, and allergic response. It is also typically necessary that a composition be sterilized to reduce the risk of infection.

Antibacterial Agent Containing Antiseptic Solutions

An antimicrobial agent containing antiseptic solution of the present invention may contain at least one alcohol, at least one antimicrobial agent and at least one chelator and/or anticoagulant. Various antimicrobial substances as disclosed herein and that are well known to one of ordinary skill in the art may be combined with the locking solution in order to inhibit infection. The antimicrobial locking solution of the present invention may be use for filling or flushing a medical device such as an indwelling device such as an implanted catheter. Other medical devices that are contemplated for use in the present invention are disclosed herein.

In another preferred form of the invention, the antiseptic agent can contain antibacterial agents such as those classified as aminoglycosides, beta lactams, quinolones or fluoroquinolones, macrolides, sulfonamides, sulfamethoxazoles, tetracyclines, streptogramins, oxazolidinones (such as linezolid), clindamycins, lincomycins, rifamycins, glycopeptides, polymyxins, lipopeptide antibiotics, as well as pharmacologically acceptable sodium salts, pharmacologically acceptable calcium salts, pharmacologically acceptable potassium salts, lipid formulations, derivatives and/or analogs of the above.

The aminoglycosides are bactericidal antibiotics that bind to the 30S ribosome and inhibit bacterial protein synthesis. They are typically active against aerobic gram-negative *bacilli* and *staphylococci*. Exemplary aminoglycosides that may be used in some specific aspects of the invention include amikacin, kanamycin, gentamicin, tobramycin, or netilmicin.

Suitable beta lactams are selected from a class of antibacterials that inhibit bacterial cell wall synthesis. A majority of the clinically useful beta-lactams belong to either the penicillin group (penam) or cephalosporin (cephem) groups. The beta-lactams also include the carbapenems (e.g., imipenem), and monobactams (e.g., aztreonam). Inhibitors of beta-lactamase such as clavulanic acid and its derivatives are also included in this category.

Non-limiting examples of the penicillin group of antibiotics that may be used in the solutions of the present invention include amoxicillin, ampicillin, benzathine penicillin G, carbenicillin, cloxacillin, dicloxacillin, piperacillin, or ticarcillin, etc. Examples of cephalosporins include ceftiofur, ceftiofur sodium, cefazolin, cefaclor, ceftibuten, ceftizoxime, cefoperazone, cefuroxime, cefprozil, ceftazidime, cefotaxime, cefadroxil, cephalexin, cefamandole, cefepime, cefdinir, ceftriaxone, cefixime, cefpodoximeproxetil, cephapirin, cefoxitin, cefotetan etc. Other examples of beta lactams include imipenem or meropenem which are extremely active parenteral antibiotics with a spectrum against almost all gram-positive and gram-negative organisms, both aerobic and anaerobic and to which *Enterococci, B. fragilis*, and *P. aeruginosa* are particularly susceptible.

Suitable beta lactamase inhibitors include clavulanate, sulbactam, or tazobactam. In some aspects of the present invention, the antibacterial solutions may comprise a combination of at least one beta lactam and at least one beta lactamase inhibitor.

Macrolide antibiotics are another class of bacteriostatic agents that bind to the 50S subunit of ribosomes and inhibit bacterial protein synthesis. These drugs are active against aerobic and anaerobic gram-positive cocci, with the exception of enterococci, and against gramnegative anaerobes. Exemplary macrolides include erythromycin, azithromycin, clarithromycin.

Quinolones and fluoroquinolones typically function by their ability to inhibit the activity of DNA gyrase. Examples include nalidixic acid, cinoxacin, trovafloxacin, ofloxacin, levofloxacin, grepafloxacin, trovafloxacin, sparfloxacin, norfloxacin, ciprofloxacin, moxifloxacin and gatifloxacin.

Sulphonamides are synthetic bacteriostatic antibiotics with a wide spectrum against most gram-positive and many gram-negative organisms. These drugs inhibit multiplication of bacteria by acting as competitive inhibitors of p-aminobenzoic acid in the folic acid metabolism cycle. Examples include mafenide, sulfisoxazole, sulfamethoxazole, and sulfadiazine.

The tetracycline group of antibiotics include tetracycline derivatives such as tigecycline which is an investigational new drug (IND), minocycline, doxycycline or demeclocycline and analogs such as anhydrotetracycline, chlortetracycline, or epioxytetracycline.

Suitable streptogramin class of antibacterial agents include quinupristin, dalfopristin or the combination of two streptogramins.

Drugs of the rifamycin class typically inhibit DNA-dependent RNA polymerase, leading to suppression of RNA synthesis and have a very broad spectrum of activity against most gram-positive and gram-negative bacteria including *Pseudomonas aeruginosa* and *Mycobacterium* species. An exemplary rifamycin is rifampicin.

Other antibacterial drugs are glycopeptides such as vancomycin, teicoplanin and derivatives thereof. Yet other antibacterial drugs are the polymyxins which are exemplified by colistin.

In addition to these several other antibacterial agents such as prestinomycin, chloramphenicol, trimethoprim, fusidic acid, metronidazole, bacitracin, spectinomycin, nitrofurantoin, daptomycin or other lipopeptides, oritavancin, dalbavancin, ramoplanin, ketolide etc. may be used in preparing the antiseptic solutions described herein. Of these, metronidazole is active only against protozoa, such as *Giardia lamblia, Entamoeba histolytica* and *Trichomonas vaginalis*, and strictly anaerobic bacteria. Spectinomycin, is a bacteriostatic antibiotic that binds to the 30S subunit of the ribosome, thus inhibiting bacterial protein synthesis and nitrofurantoin is used orally for the treatment or prophylaxis of UTI as it is active against *Escherichia coli, Klebsiella-Enterobacter* species, *staphylococci*, and *enterococci*.

In other embodiments, the antimicrobial agent is an antifungal agent. Some exemplary classes of antifungal agents include imidazoles or triazoles such as clotrimazole, miconazole, ketoconazole, econazole, butoconazole, omoconazole, oxiconazole, terconazole, itraconazole, fluconazole, voriconazole, posaconazole, ravuconazole or flutrimazole; the polyene antifungals such as amphotericin B, liposomal amphotericin B, natamycin, nystatin and nystatin lipid formulations; the cell wall active cyclic lipopeptide antifungals, including the echinocandins such as caspofungin, micafungin, anidulafungin, cilofungin; LY121019; LY303366; the allylamine group of antifungals such as terbinafine. Yet other non-limiting examples of antifungal agents include naftifine, tolnaftate, mediocidin, candicidin, trichomycin, hamycin, aureofungin, ascosin, ayfattin, azacolutin, trichomycin, levorin, heptamycin, candimycin, griseofulvin, BF-796, MTCH 24, BTG-137586, pradimicins (MNS 18184), benanomicin; ambisome; nikkomycin Z; flucytosine, or perimycin.

In another preferred form of the invention, the antimicrobial agent is an antiviral agent. Non-limiting examples of antiviral agents include cidofovir, amantadine, rimantadine, acyclovir, gancyclovir, penciclovir, famciclovir, foscarnet, ribavirin, or valaciclovir. In some forms of the invention the antimicrobial agent is an innate immune peptide or proteins. Some exemplary classes of innate peptides or proteins are transferrins, lactoferrins, defensins, phospholipases, lysozyme, cathelicidins, serprocidins, bactericidal permeability increasing proteins, amphipathic alpha helical peptides, and other synthetic antimicrobial proteins.

In other embodiments of the invention, the antimicrobial agent is an antiseptic agent. Several antiseptic agents are known in the art and these include a taurinamide derivative, a phenol, a quaternary ammonium surfactant, a chlorine-containing agent, a quinaldinium, a lactone, a dye, a thiosemicarbazone, a quinone, a carbamate, urea, salicylamide, carbanilide, a guanide, an amidine, an imidazoline biocide, acetic acid, benzoic acid, sorbic acid, propionic acid, boric acid, dehydroacetic acid, sulfurous acid, vanillic acid, esters of p-hydroxybenzoic acid, isopropanol, propylene glycol, benzyl alcohol, chlorobutanol, phenylethyl alcohol, 2-bromo-2-nitropropan-1,3-diol, formaldehyde, glutaraldehyde, calcium hypochlorite, potassium hypochlorite, sodium hypochlorite, iodine (in various solvents), povidone-iodine, hexamethylenetetramine, noxythiolin, 1-(3-chloroallyl)-3,5,7-triazo 1-azoniaadamantane chloride, taurolidine, taurultam, N(5-nitro-2-furfurylidene)-1-amino-hydantoin, 5-nitro-2-furaldehyde semicarbazone, 3,4,4'-trichlorocarbanilide, 3,4',5-tribromosalicylanilide, 3-trifluoromethyl-4,4'-dichlorocarbanilide, 8-hydroxyquinoline, 1-cyclopropyl-6-fluoro-1,4-dihydro-4-oxo-7-(1-piperazinyl)-3-quinolinecarboxylic acid, 1,4-dihydro-1-ethyl-6-fluoro-4-oxo-7-(1-piperazinyl)-3-quinolinecarboxylic acid, hydrogen peroxide, peracetic acid, phenol, sodium oxychlorosene, parachlorometaxylenol, 2,4,4'-trichloro-2'-hydroxydiphenol, thymol, chlorhexidine, benzalkonium chloride, cetylpyridinium chloride, silver sulfadiazine, or silver nitrate.

In another preferred form of the invention, the antiseptic solution includes a basic reagent and a dye. The basic reagent may be a guanidium compound, a biguanide, a bipyridine, a phenoxide antiseptic, an alkyl oxide, an aryl oxide, a thiol, a halide, an aliphatic amine, or an aromatic amine. In some specific aspects, the basic reagent is a guanidium compound. Non-limiting examples of guanidium compounds include chlorhexidine, alexidine, hexamidine. In other specific embodiments, the basic reagent is a bipyridine. One example of a bipyridine is octenidine. In yet other aspects, the basic reagent is a phenoxide antiseptic.

The dye may be a triarylmethane dye, a monoazo dye, a diazo dye, an indigoid dye, a xanthene dye, an anthraquinone dye, a quinoline dye, an FD&C dye. Non-limiting examples of triarylmethane dye include gentian violet, crystal violet, ethyl violet, or brilliant green. Exemplary monoazo dyes include FD&C Yellow No. 5, or FD&C Yellow No. 6. Other non-limiting examples of FD&C dye include Blue No. 1 or Green No. 3. One non-limiting example of diazo dyes is D&C Red No. 17. An example of an indigoid dye is FD&C Blue No. 2. An example of a xanthene dye is FD&C Red No. 3; of an anthraquinone dye is D&C Green No. 6; and of an quinoline dye is D&C Yellow No. 1.

Other examples of antiseptics that may be used to the solutions of the invention are the phenoxide antiseptics such as clofoctol, chloroxylenol or triclosan. Still other antiseptic agents that may be used to prepare the antimicrobial solutions of the invention are gendine, genlenol, genlosan, or genfoctol.

One of skill in the art will appreciate that one can use one or more of the antimicrobial agents including one or more antibacterial agent, and/or one or more antifungal agent, and/or one or more antiviral agent, and/or one or more antiseptic agent, and/or combinations thereof.

A wide variety of chelator agents are contemplated as useful in preparing the antiseptic solutions of the invention. This includes chelators such as EDTA free acid, EDTA 2Na, EDTA. 3Na, EDTA 4Na, EDTA 2K, EDTA 2Li, EDTA 2NH$_4$, EDTA 3K, Ba(II)-EDTA, Ca(II)-EDTA, Co(II)-EDTACu(II)-EDTA, Dy(III)-EDTA, Eu(III)-EDTA, Fe(III)-EDTA, In(III-EDTA, La(III)-EDTA, CyDTA, DHEG, diethylenetriamine penta acetic acid (DTPA), DTPA-OH, EDDA, EDDP, EDDPO, DTPA-OH, EDTPO, EGTA, HBED, HDTA, HIDA, IDA, MethylEDTA, NTA, NTP, NTPO, O-Bistren, TTHA, EGTA, DMSA, deferoxamine, dimercaprol, zinc citrate, a combination of bismuth and citrate, penicillamine, succimer or Etidronate. It is contemplated that any chelator which binds barium, calcium, cerium, cobalt, copper, iron, magnesium, manganese, nickel, strontium, or zinc will be acceptable for use in the present invention.

Alternatively, one may use at least one anticoagulant such as heparin, hirudin, EGTA, EDTA, urokinase, streptokinase, hydrogen peroxide etc., in the preparation of the antimicrobial solutions of the invention.

In addition to the alcohols set forth above, a variety of alcohols are contemplated as useful in the preparation of the instant antiseptic solution, and include any antimicrobially active alcohol. Non-limiting examples of alcohols include ethanol, methanol, isopropanol, propylene glycol, benzyl alcohol, chlorobutanol, phenylethyl alcohol, and the like.

One of skill in the art will appreciate that the solutions of the instant invention can comprise various combinations of at least one alcohol, at least one antimicrobial agent, and at least one chelator/anticoagulant. In some specific embodiments, the solution of the invention comprises at least one alcohol, at least one tetracycline and at least one chelator/anticoagulant. In a specific aspect, such an antimicrobial solution comprises ethanol, at least one tetracycline and EDTA or heparin.

In other specific aspects, such a solution comprises ethanol, minocycline and EDTA or heparin. In one embodiment of this aspect, the concentration of minocycline is 0.001 mg/ml to 100 mg/ml. In another embodiment, the concentration of minocycline is about 3 mg/ml. In another aspect, the concentration of EDTA is in the range of 10-100 mg/ml. In one embodiment of this aspect, the concentration of EDTA is about 30 mg/ml.

In another preferred form of the invention, the antiseptic solution includes a pharmacologically acceptable sodium salt, a pharmacologically acceptable calcium salt, a pharmacologically acceptable potassium salt and about one milligram per milliliter polyhexamethylene biguanide hydrochloride in an aqueous admixture. Additionally, the solution of the invention may also contain a pharmacologically acceptable salt of lactic acid.

Salt Containing Antiseptic Solutions

One preferred antiseptic solution includes a pharmacologically acceptable sodium salt such as sodium chloride or the like in a concentration of between about 820 mg to about 900 mg, a pharmacologically acceptable calcium salt, such as calcium chloride dihydrate or the like in a concentration between about 30.0 mg to about 36.0 mg, a pharmacologically acceptable potassium salt, such as potassium chloride or the like in a concentration between about 28.5 to about 31.5 mg and about one milligram per milliliter polyhexamethylene biguanide hydrochloride in an aqueous admixture with one hundred milliliters of water for injection U.S.P. For particular applications, the solution of the invention may also include sodium lactate in a concentration between about 290 mg and about 330 mg in the one hundred milliliter aqueous admixture.

Photo-oxidant Solutions

In another preferred form of the present invention, the antiseptic solution contains an anticoagulant and a photo-oxidant. In certain embodiments, a photo-oxidant is selected that has an antiseptic effect. As used herein, the term "photo-oxidant" is intended to refer to a compound (usually an organic dye) that has photo-oxidation properties, in which the compound exhibits an increased oxidizing potential upon exposure to radiant energy such as light. The term "photo-oxidant" also refers to a composition that releases one or more electrons when struck by light.

In one preferred aspect of the invention, the photo-oxidant is methylene blue, which advantageously provides antibiotic and antifungal activity, and also provides a color to make the antiseptic solution clearly identifiable. In addition to methylene blue, other photo-oxidants may include Rose Bengal, hypericin, methylene violet, proflavine, rivanol, acriflavine, toluide blue, trypan blue, neutral red, a variety of other dyes or mixtures thereof. Therefore, in alternate aspects of the invention, one or more alternative photo-oxidants, preferably a colored photo-oxidant is used in accordance with the invention in place of methylene blue.

Enhanced Viscosity Solutions

In another preferred form of the invention, the antiseptic solution includes a low viscosity antibacterial agent mixed with a viscosity increasing agent. Examples of antibacterial agents which may be used, in addition to those described above, comprise alcohols, chlorhexidine, Clorpactin, iodine, tauroline, citric acid, and soluble citric acid salts, particularly sodium citrate, optionally mixed with water.

Suitable viscosity increasing agents include Carbopol, starch, methylcellulose, carboxypolymethylene, carboxymethyl cellulose, hydroxypropylcellulose, or the like. Carbopol is a cross-linked polyacrylic acid based polymer sold by Noveon, Inc. It is preferably neutralized to about pH 7 with a base material such as tetrahydroxypropyl ethylene diamine, triethanolamine, or sodium hydroxide. Derivatives of starch may also be used, such as hydroxyethylstarch, hydroxypropylstarch, or starch having bonded organic acid ester groups, to improve compatibility with antibacterial agents such as alcohols, for example, ethanol or isopropanol. Such ester groups may be the reaction product of two to twelve carbon organic acids with the starch, for example. Also, the elevated viscosity antiseptic solution may be created by the use of a fat emulsion, or other dispersions in water/alcohol of glycerol mono or di esters of fatty acids, or fatty acid esters of other polyols such as sugars having one or more bonded fatty acid groups per molecule. Analogous compounds with ether linkages may also be used.

Also, other materials such as alginic acid, with or without calcium citrate may be used, or polyvinyl alcohol, with or without borax, povidone, polyethylene glycol alginate, sodium alginate, and/or tragacanth. If desired, the fluid of this invention may also contain an effective amount of an antithrombogenic agent such as heparin, and a diluent such as water, along with other desired ingredients.

In one preferred form of the invention, the antiseptic solution contains a mixture of isopropyl alcohol and neutralized Carbopol, with other optional ingredients being present such as water, antithrombogenic agents such as heparin, and the like. Preferably, about 0.4 to 2 weight percent of Carbopol is present. Citric acid may also be present as an antibacterial agent, either with or as a substitute for another anti-bacterial agent such as isopropyl alcohol or ethanol.

In another embodiment, the antiseptic solution is a gel of an isopropyl alcohol, optionally with up to about 30 weight percent water, and about 2.2 weight percent hydroxypropylcellulose, to form a high viscosity antiseptic solution.

In yet another preferred form of the invention, the antiseptic solution contains carbohydrates and/or glucose degradation products. Suitable carbohydrates are chosen form the group of glucose and/or fructose. Suitable degradation products include 3-deoxyglucosone (3-DG), acetaldehyde, formaldehyde, acetaldehyde, glyoxal, methylglyoxal; 5-hydroxymethyl-2-furaldehyde (5-HMF), 2-furaldehyde, and 3,4-dideoxyglucosone-3-ene (3,4-DGE).

Other suitable agents to be used in this embodiment of the antiseptic solution includes substances having anticoagulatory properties i.e., inhibitors of the coagulation cascade such as heparin of standard and low molecular weight, fractionated heparin, synthetic inhibitors in the coagulation cascade, Futhan as a broad protease inhibitor, complexing and chelating substances such as citrate, EDTA, EGTA, substances and mixtures used for preservation of blood products (platelets or plasma), CDPA (citrate, sodium phosphate, dextrose, adenine), synthetic or natural thrombin inhibitor substances. Other suitable additives include fucosidan, riboflavin, vitamin E, alphatocopherol, folic acid and amino acids. Furthermore, antiinflammatory compounds and drugs could also be used, e.g. cortison, mycophenolic acid (MPA) and derivatives thereof, sirolimus, tacrolimus and cyclosporin, diclofenac, etc.

Inhibitory peptides can also be used in the antiseptic solution such as defensins, (dermcidine), and others. Radicals, such as reactive oxygen species, NO-releasing systems or nitric oxide (NO), and peroxynitrite may also be used. A buffer composition may also be included in the antiseptic solution, and in one preferred form of the invention, the buffer contains lactate, bicarbonate, pyruvate, ethyl pyruvate and citric acid in combination and mixtures including adjustment of pH by acetic acid, hydrochloric acid or sulphuric acid. Furthermore, viscosity enhancing additives may be added, such as lipids or lipidic substances (also to get water insoluble vitamins or complexes into solution), nutrients in high concentration density gradient e.g. aminoacid containing fluids, polyglucose, icodextrin, pectin, hydroxyethyl starch (HES), alginate, hyaluronic acid, etc.

Taurolidine Antiseptic Solutions and Gels

The antiseptic solutions of the present invention can include Taurolidine and/or Taurultam to prevent clotting and Biofilm formation or the elements can be combined with other antimicrobial agents. One embodiment of the present invention is a gel with thixotropic properties to keep the solution inside the antiseptic cap and not spill out during the time interval between uses. This is accomplished by making a hydrogel matrix as a drug delivery vehicle containing a biocompatible antimicrobial agent alone or with another active agent, which may be useful for particular purposes. The hydrogel matrix is biocompatible and, biodegradable in the bloodstream. The matrix can be a hydrogel (e.g., pectin, gelatin, etc), a protein (e.g., collagen, hemoglobin, etc), a colloidal substance (e.g., serum albumin etc.), an emulsion or other adjuvant. Preferably, the matrix shall have structural integrity and be thixotropic. Thixotropy is a property, which is exhibited by certain gels. It is a property characterized by a solid or semisolid substance that when shaken, stirred or subject to high shear forces becomes fluid like and can flow and then returns to the semisolid state when the forces and/movement are stopped. Alternatively, the gel could have the properties similar to that of the colloidal dispersion which resists movement, or flow until a high shear force is imparted to the fluid and then it flows easily.

Other ingredients may be added to the gel matrix to provide further functional benefit. The preferred antimicrobial is Taurolidine, which can be added to the matrix as a micro particle powder, or encapsulated in liposomes, microspheres, or nanospheres. It should be appreciated that numerous active agents and drugs can be added to the thixotropic gel including sterilants, lysing agents (such as Urokinase), imaging enhancers, catheter surface modifiers, antibiotics and antimicrobial chemicals.

A hydrogel comprises a three-dimensional molecular network containing large quantities of water giving them good biocompatibility with material consistency that is soft solid-like with high diffusive properties to gases, chemicals and proteins. Suitable hydrogels include natural polymers including serum albumin, collagen, or alginates, polyvinyl alcohol, poly(ethylene oxide) or poly (hydroxyethylene) and polyelectrolytes, such as poly(acrylic acid), poly(styrene sulfonate), and carboxymethylcellulose (CMC).

One preferred form of the antiseptic solution includes Taurolidine with Salicylic acid or Sodium Salicylate in an aqueous solvent. Salicylic Acid and Sodium Salicylate are drugs that have been used with antibiotic locks in catheters to enhance the biocidal action of the antibiotic alone and to inhibit the attachment of microbes to surfaces. This last attribute is especially important because the initiation of a Biofilm expression and growth require that the individual bacteria must first attach themselves to the underlying surface. By stopping attachment, Biofilm formation is blocked.

Sodium salicylate has been demonstrated to have remarkable antibacterial activity, including the ability to enhance the activities of certain antibiotics. This drug inhibits adherence, growth and Biofilm formation.

EDTA Containing Antiseptic Solutions

In one preferred antiseptic solution of the present invention provides antimicrobial, antifungal, anti-viral and anti-amoebic properties and may also serve as an anti-coagulant. Specified salts and compositions of ethylene diamine tetraacetic acid (EDTA) ($C_{10}H_{12}N_2Na_4O_8$) are used at specified concentrations and pH levels.

The EDTA formulations of the present invention are safe for human administration and are biocompatible and non-corrosive. They may also have anticoagulant properties and are thus useful for preventing and/or treating a variety of catheter-related infections. In one embodiment, antiseptic solutions of the present invention have at least four, and preferably at least five, of the following properties: anticoagulant properties; inhibitory and/or bactericidal activity against a broad spectrum of bacteria in a planktonic form; inhibitory and/or fungicidal activity against a spectrum of fungal pathogens; inhibitory and/or bactericidal activity against a broad spectrum of bacteria in a sessile form;

inhibitory activity against protozoan infections; inhibitory activity against Acanthamoeba infections; safe and biocompatible, at least in modest volumes, in contact with a patient; safe and biocompatible, at least in modest volumes, in a patient's bloodstream; and safe and compatible with industrial objects and surfaces. The antiseptic solution can have a pH higher than physiological pH such as a pH of >8.0, or at a pH>8.5, or at a pH>9, or at a pH>9.5.

In another preferred form of the invention, the antiseptic solution contain a sodium EDTA salt (or combination of sodium salts) in solution at a pH in the range between 8.5 and 12.5 and, in another embodiment, at a pH of between 9.5 and 11.5 and, in yet another embodiment, at a pH of between 10.5 and 11.5.

When used herein, the term "EDTA salt" may refer to a single salt, such as a di-sodium or tri- sodium or tetra-sodium salt, or another EDTA salt form, or it may refer to a combination of such salts. The composition of EDTA salt(s) depends both on the EDTA salts used to formulate the composition, and on the pH of the composition. For antiseptic solutions of the present invention consisting of sodium EDTA salt(s), and at the desired pH ranges (specified above), the sodium EDTA salts are predominantly present in both the tri-sodium and tetra-sodium salt forms.

In one embodiment, the antiseptic solution contains a combination of at least the tri-sodium and tetra-sodium salts of EDTA, and more preferably solutions containing at least 10% of the EDTA in the composition is present in the tetra-sodium salt form. In yet another embodiment, at least 50% and, more preferably at least 60%, of the EDTA in the composition is present in the tri-sodium salt form.

EDTA solutions of the present invention are preferably provided in a sterile and non-pyrogenic form and may be packaged in any convenient fashion. The compositions may be prepared under sterile, aseptic conditions, or they may be sterilized following preparation and/or packaging using any of a variety of suitable sterilization techniques.

Formulation and production of antiseptic compositions of the present invention is generally straightforward. In one embodiment, desired antiseptic solutions of the present invention are formulated by dissolving one or more EDTA salt(s) in an aqueous solvent, such as purified water, to the desired concentration and adjusting the pH of the EDTA salt solution to the desired pH. The antiseptic solution may then be sterilized using conventional means, such as autoclaving, UV irradiation, filtration and/or ultrafiltration, and other means. The preferred osmolarity range for EDTA solutions is from 240-500 mOsM/Kg, more preferably from 300-420 mOsM/Kg. The solutions are preferably formulated using USP materials.

Antiseptic solutions containing sodium salts of EDTA other than tri- and tetra-sodium salts, such as di-sodium EDTA, is also contemplated. For example di-sodium EDTA solutions can be used but such solutions have a lower pH in solution than the desired pH range of compositions of the present invention but, upon pH adjustment to the desired range using a pH adjustment material, such as sodium hydroxide, sodium acetate, and other well-known pH adjustment agents, EDTA solutions prepared using di-sodium salts are converted to the preferred combination di- and/or tri- and/or tetra-sodium salt EDTA solutions of the present invention. Thus, different forms and combinations of EDTA salts may be used in the preparation of EDTA compositions of the present invention, provided that the pH of the composition is adjusted to the desired pH range prior to use. In one embodiment, antiseptic compositions consisting of a mixture of primarily tri-and tetra-sodium EDTA is provided by dissolving di-sodium EDTA in an aqueous solution, 3%-5% on a weight/volume basis, and adding sodium hydroxide in a volume and/or concentration sufficient to provide the desired pH of>8.5 and <12.0.

Antibacterial Enzyme Containing Antiseptic Solutions

"Antibacterial enzyme" refers to any proteolytic, pore-forming, degradative or inhibitory enzyme that kills or damages a bacterial species or particular strain thereof. The result may be achieved by damaging the cell wall of the bacteria, disrupting cell membranes associated with the cell wall or within the bacteria, inhibiting protein synthesis within the bacteria, disrupting the sugar backbone, or by any other mechanism attributed to a peptide or protein considered by those skilled in the art to be an antibacterial enzyme. The enzyme may be a natural, wild-type enzyme, modified by conventional techniques, conjugated to other molecules, recombinantly expressed, or synthetically constructed.

One example of an antibacterial enzyme is lysostaphin. Lysostaphin is important because it is effective in the treatment of staphylococci and biofilms formed therefrom. "Lysostaphin," and "lysostaphin analogues" are defined as including lysostaphin (wild type), any lysostaphin mutant or variant, any recombinant, or related enzyme (analogue) or any synthetic version or fragment of lysostaphin (whether synthetic or otherwise) that retains the proteolytic ability, in vivo and in vitro, to cleave the cross-linked polyglycine bridges in the cell wall peptidoglycan of *staphylococci*. The enzymes may be generated by post-translational processing of the protein (either by enzymes present in a producer strain or by means of enzymes or reagents introduced at any stage of the process) or by mutation of the structural gene. Mutations may include site deletion, insertion, domain removal and replacement mutations.

The lysostaphin may be synthetically constructed, expressed in mammalian cells, insects, bacteria, yeast, reptiles or fungi, recombinantly expressed from a cell culture or higher recombinant species such as a mouse, or otherwise. This would include the activity-retaining synthetic construction including synthetic peptides and polypeptides or recombinant expression of portions of the lysostaphin enzyme responsible for its activity against *staphylococci* as part of a larger protein or peptide, include chimeric proteins, containing the active sites of one or more other antibacterial enzymes that are effective either against *staphylococci* or other biofilmforming bacteria species.

The antibacterial enzymes may also be coated on the surface of the devices described herein by immersion of the device in a solution of the enzyme for a length of time sufficient to form a biofilm-formation inhibiting coating of the enzyme on the susceptible surface. Even the most minimal concentration of enzyme will confer some protection. Typically, a concentration of from about 10 µg/ml to about 100 mg/ml can be used. With device surfaces, the coatings may also be formed by covalent attachment of the enzyme thereto.

Antiseptic Coatings

It is contemplated that the devices described herein can be coated with an antiseptic coating by any suitable technique such as immersion of the part into an antiseptic solution, by spray coating the part with the antiseptic solution, by blending the antiseptic solution or material into the polymeric material used to fabricate the device.

In one preferred form of the invention, a quantity of physiological, antimicrobial metal compound is added to the resin for direct molding of an article. Physiological, antimicrobial metals are meant to include the precious metals, such as silver, gold and platinum, and copper and zinc. Physiological, antimicrobial metal compounds used herein include oxides and salts of preferably silver and also gold, for example: silver acetate, silver benzoate, silver carbonate, silver citrate, silver chloride, silver iodide, silver nitrate, silver oxide, silver sulfadiazine, silver sulfate, gold chloride and gold oxide. Platinum compounds such as chloroplatinic acid or its salts (e.g., sodium and calcium chloroplatinate) may also be used. Also, compounds of copper and zinc may be used, for example: oxides and salts of copper and zinc such as those indicated above for silver. Single physiological, antimicrobial metal compounds or combinations of physiological, antimicrobial metal compounds may be used.

Preferred physiological, antimicrobial metal compounds used in this invention are silver acetate, silver oxide, silver sulfate, gold chloride and a combination of silver oxide and gold chloride. The particles of the silver compounds are sufficiently able to be extracted to form a zone of inhibition to prevent and kill bacteria growth.

In another preferred form of the invention the devices herein are impregnated with triclosan and silver compounds or triclosan and chlorhexidine.

Figure 62:
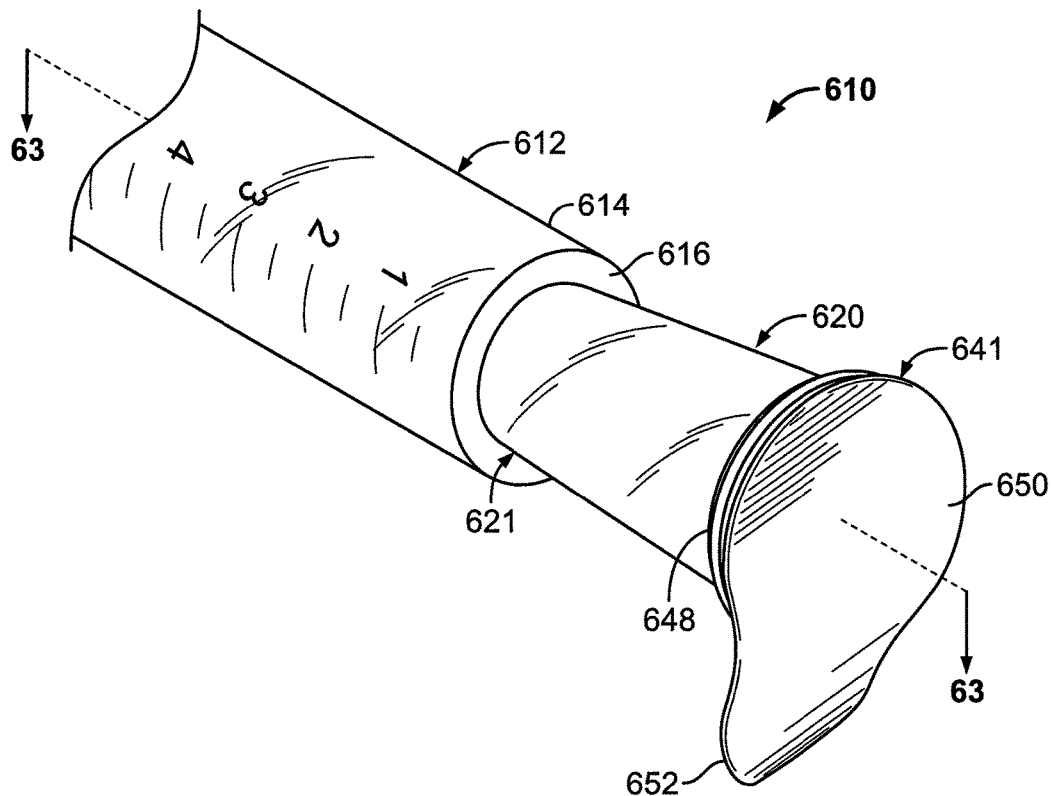
FIG. 62 is a perspective view of a tip cap assembly having an antiseptic cap attached to a syringe.
Figure 63:
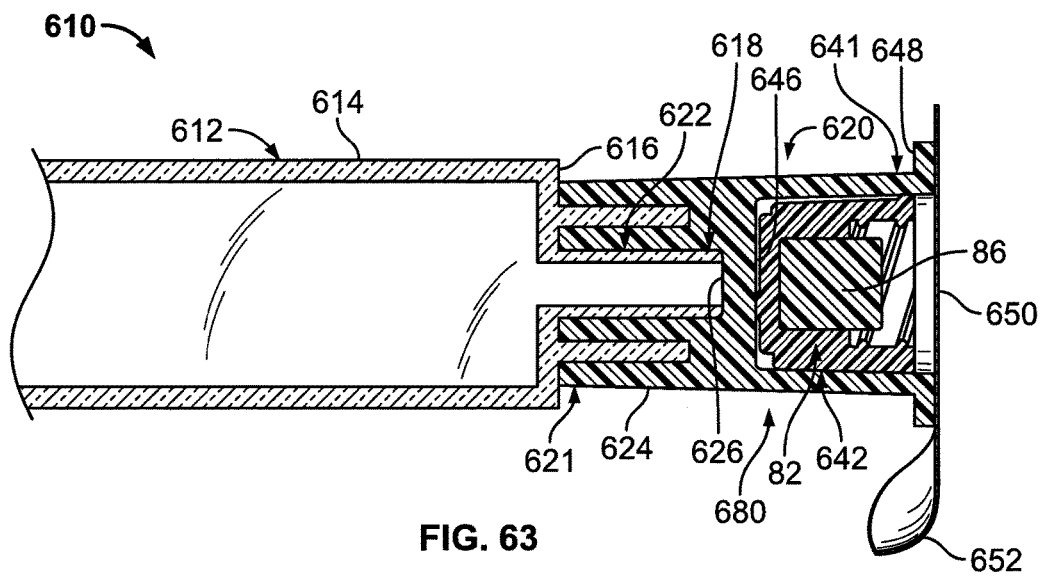
FIG. 63 is a cross-sectional view of a tip cap having an antiseptic cap attached to a syringe.

Referring to FIGS. 62 and 63, a syringe having a tip cap with an antiseptic cap disposed thereon is generally indicated at 610. This arrangement facilitates use of the antiseptic cap by providing the cap in a convenient location at the proper time it can be used. The syringe 612 includes a barrel 614 having a forward end 616. The forward end of the syringe 612 is configured with an access point connection 618 for attachment to an access point to deliver a fluid or medicament to a patient. Prior to use, the syringe access point connection 618 is covered with a tip cap 620. The tip cap 620 has a proximal end 621 that is attached to the access point connection of the syringe 612. The tip cap 620 also has a distal end 641 that carries an antiseptic cap 82. The antiseptic cap 82 could contain an absorbent material such as a sponge 86. The sponge 86 could be made from bonded fiber such as the bonded fiber material which is available from Filtrona Porous Technologies, based in Richmond, Va. The sponge 86 can store an antiseptic liquid.

As can be seen in FIGS. 62 and 63, a cap assembly 680 is sealed by a cover or film 650 which is attached to the surface of the tip cap 620 such as to a flange 648. A pull tab 652 may be provided for facilitating removal of the film 650 to provide access to the antiseptic cap 82.

Referring to FIG. 63, it can be seen that the tip cap 620 has proximal and distal chambers 622 and 642 respectively, positioned within a cylindrical or tapered side wall 624. The side wall 624 is shown to be continuous but it could have discrete areas of different sizes to accommodate chambers of different sizes. The side wall 624 could include ribs or gripping surfaces to facilitate handling thereof. The proximal chamber 622 is configured for attachment to the access point connection 618 on the forward end 616 of the barrel 614 of the syringe 612 as is known. As shown, the proximal chamber 622 of the tip cap 620 receives and releasably engages the central male extension of the access point connection 618, as well as the annular surface that extends thereabout. The configuration of the proximal chamber 622 can be varied in accordance with what is known in the art. The proximal chamber 622 could have a base wall 626.

Figure 64:
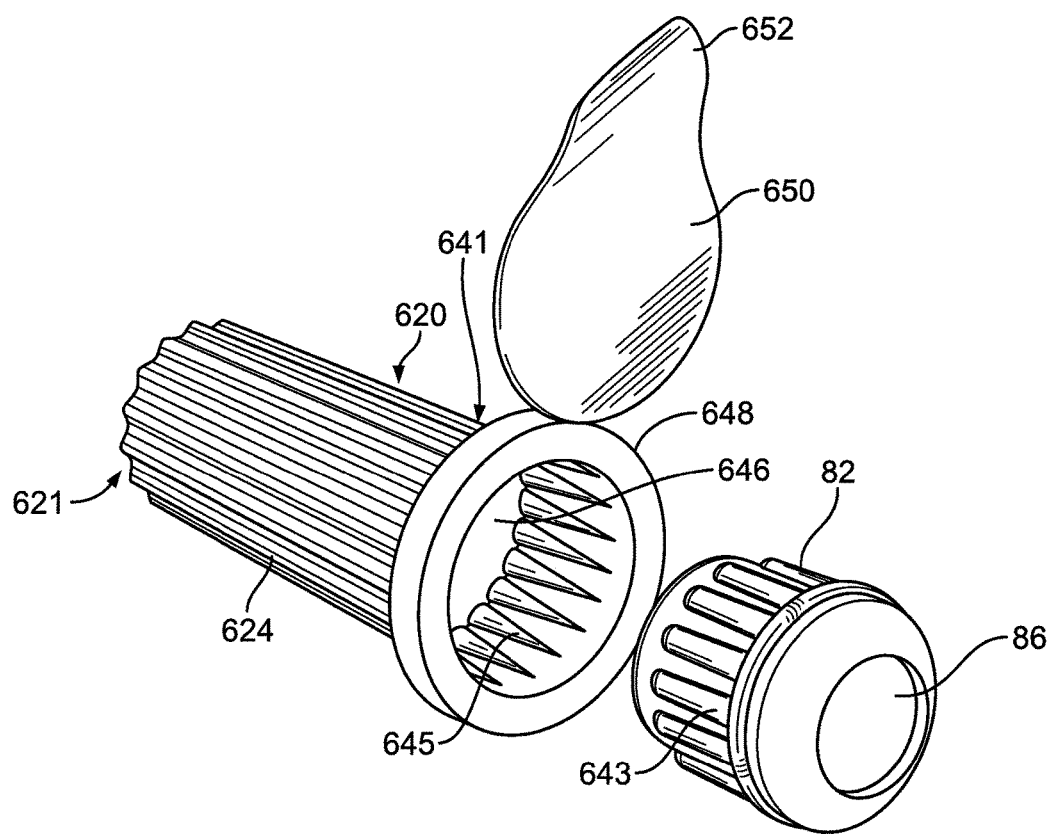
FIG. 64 is an exploded, perspective view showing an antiseptic cap and a tip cap.

The distal chamber 642 is sized and configured to receive an antiseptic cap 82. The distal chamber 642 could have a base wall 646. As with the plunger equipped antiseptic cap previously described, the antiseptic cap 82 could have one or more ribs 643 as shown in FIG. 64, and the inner wall of the distal chamber 642 could have corresponding ribs 645 to prevent relative rotational movement between the distal chamber 642 and the antiseptic cap 82.

In use, a syringe with an antiseptic cap 82 is provided with a fluid or medicament for delivery to a patient through an access point. The tip cap 620 is removed from the syringe 612 and the syringe 612 is connected to the access point and actuated to deliver the fluid or medicament. The syringe 612 is then disconnected from the access point, the tip cap 620 is accessed, and the pull tab 652 is used to remove the cover 650 to provide access to the antiseptic cap 82. Then, gripping the tip cap 620, one places the antiseptic cap 82 on the access point and pushes and/or twists the antiseptic cap 82 onto the access point. Once the antiseptic cap 82 is attached to the access point, the tip cap 620 can be removed such that the antiseptic cap 82 is withdrawn from the distal chamber 642 and remains attached to the access point where it disinfects and protects the access point until the next time the access point is accessed.

Figure 65:
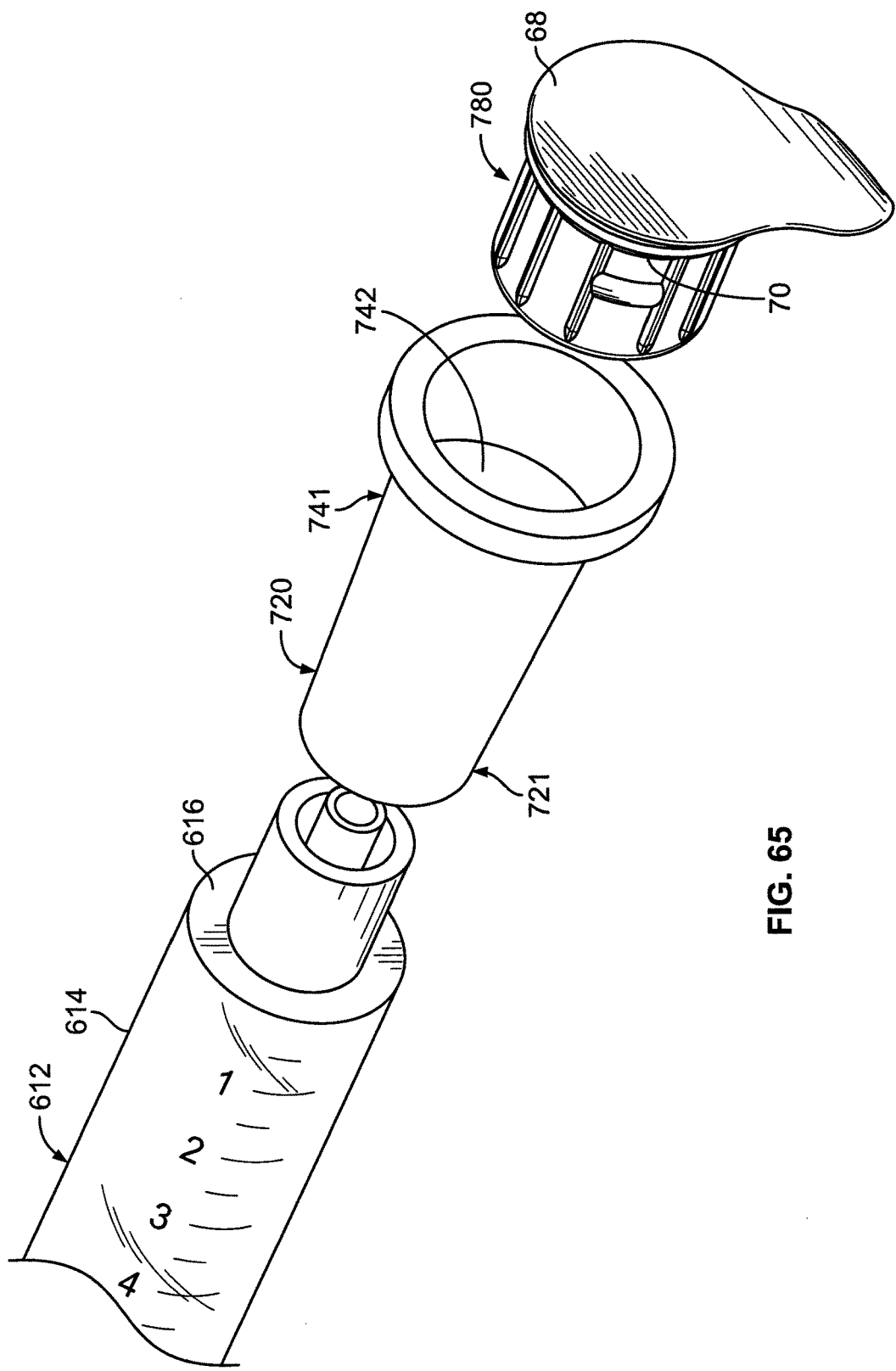
FIG. 65 is an exploded, perspective view showing an antiseptic cap holder assembly, a tip cap, and a syringe.

FIG. 65 shows another aspect of a tip cap 720 wherein a distal chamber 742 is configured to receive a cap holder assembly 780 having an antiseptic cap. The tip cap 720 has a proximal end 721 and a distal end 741. In this aspect, the distal chamber 742 is configured in accordance with the configuration of the chamber of the plunger equipped antiseptic cap previously described and receives the cap holder assembly 780 therein. The antiseptic cap can be used as discussed previously, or the cap holder assembly 780 can be removed from the tip cap 720 and used directly.

Figure 66:
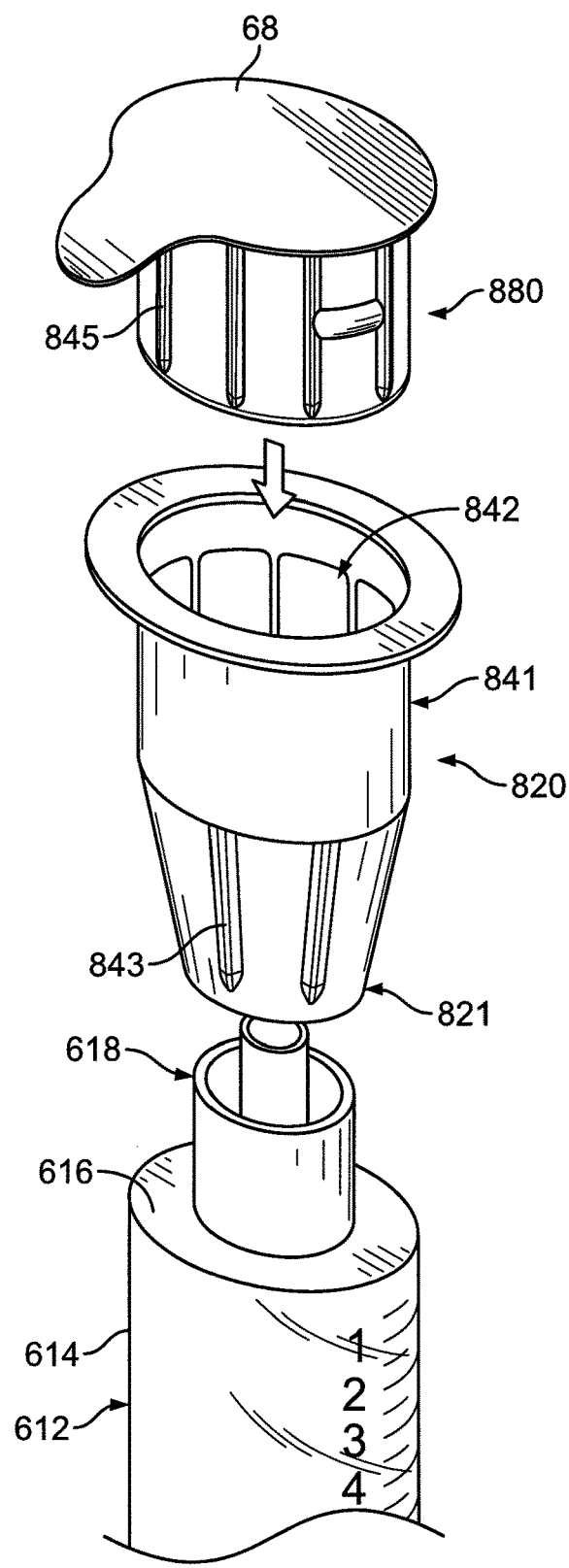
FIG. 66 is an exploded, perspective view showing an antiseptic cap holder assembly, a tip cap, and a syringe.

FIG. 66 shows another aspect of a tip cap 820 wherein a distal chamber 842 is configured to receive a cap holder assembly 880 having an antiseptic cap. The tip cap 820 has a proximal section 821 and a distal section 841. As illustrated, the proximal section 821 and the distal section 841 can be two discrete sections of varying shape and size. For example, the proximal section 821 could have a cylindrical or tapered side wall, as shown. The discrete sections of varying shape or size can accommodate chambers of different sizes. Further, the discrete sections, e.g., the proximal section 821 and the distal section 841, could include ribs 843 or gripping surfaces to facilitate handling thereof. In this aspect, the tip cap 820 is configured to change geometry from the proximal section 821 to the distal section 841. Specifically, the proximal section 821 is shown to have a truncated conical shape and configured to attach to the access point connection 618 of a syringe 612, while the distal section 841 is designed and configured to receive the cap holder assembly 880. The cap holder assembly 880 may have ribs 845 that coact with ribs 843 on the distal chamber 842 to prevent rotation of the cap holder assembly 880 with respect to the tip cap 820. The antiseptic cap can be used as discussed previously, or the cap holder assembly 880 can be removed from the tip cap 820 and used directly.

Figure 67A:
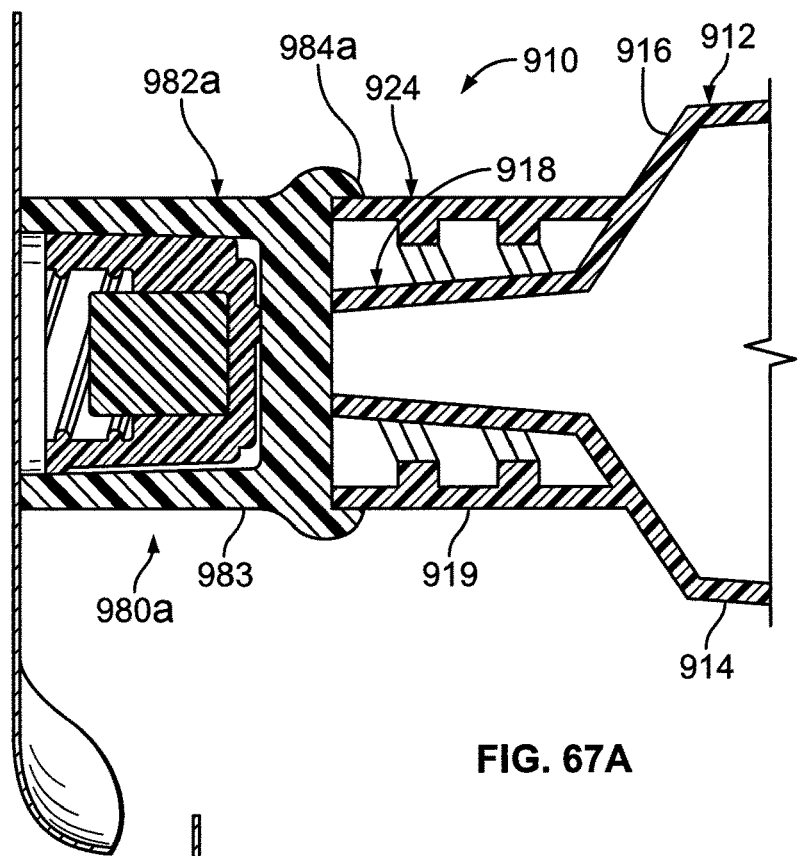
FIG. 67A is a cross-sectional view of an antiseptic cap assembly attached to a syringe.
Figure 67B:
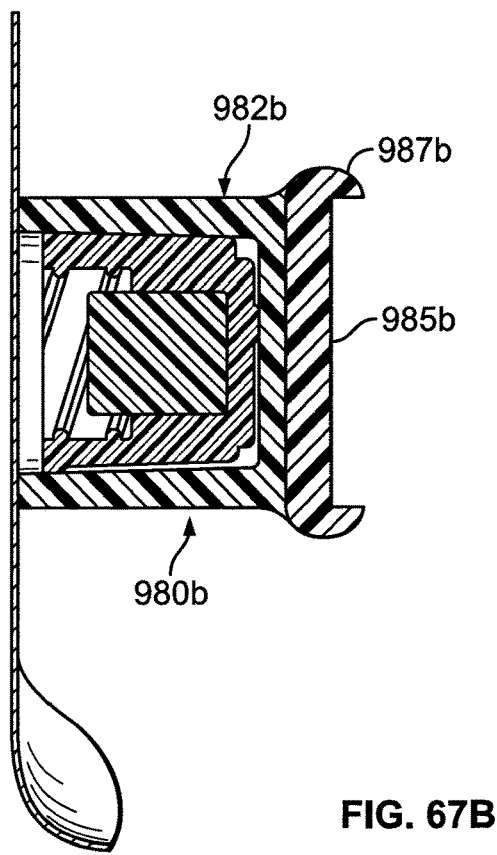
FIG. 67B is a cross-sectional view of an antiseptic cap assembly and a flexible cap.

FIG. 67A is a cross-sectional view showing a syringe with an antiseptic cap assembly 980a disposed thereon generally indicated at 910. The syringe 912 includes a barrel 914 having a forward end 916. The forward end 916 of the syringe 912 is configured with an access point connection 918 and a cylindrical wall 919 for attachment to an access point to deliver a fluid or medicament to a patient. Prior to use, the syringe access point connection 918 is covered with a cap assembly 980a that engages the cylindrical wall 919. The cap assembly 980a includes an antiseptic cap 982a and a flexible ring 984a. The flexible ring 984a could be formed by an extension of the outer surface 983 of the cap assembly 980 or, the flexible ring 984a could be in the form of a flexible cap having a top 985b and a circular ring 987b with a cap assembly 980b attached to the top 985b, as shown in FIG. 67B. The cap assembly 980 is attached to the cylindrical wall 919 of the syringe 612 by stretching the flexible ring 984 around the cylindrical wall 919 such that the flexible ring 984 forms around and engages the cylindrical wall 919. The flexible ring 984 is biased towards a normal diameter that is smaller than, or equal to, the diameter of the cylindrical wall 919, such that the cap assembly 980 is secured to the syringe 912.

Figure 68:
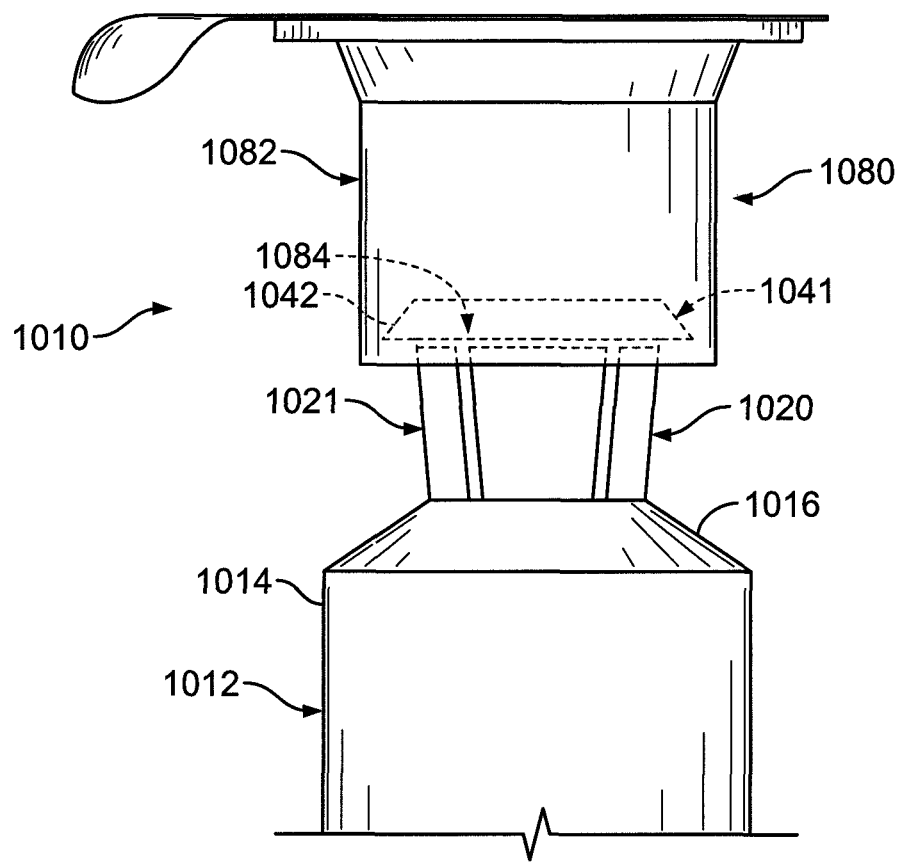
FIG. 68 is a side view of an antiseptic cap holder assembly attached to a tip cap attached to a syringe.
Figure 69:
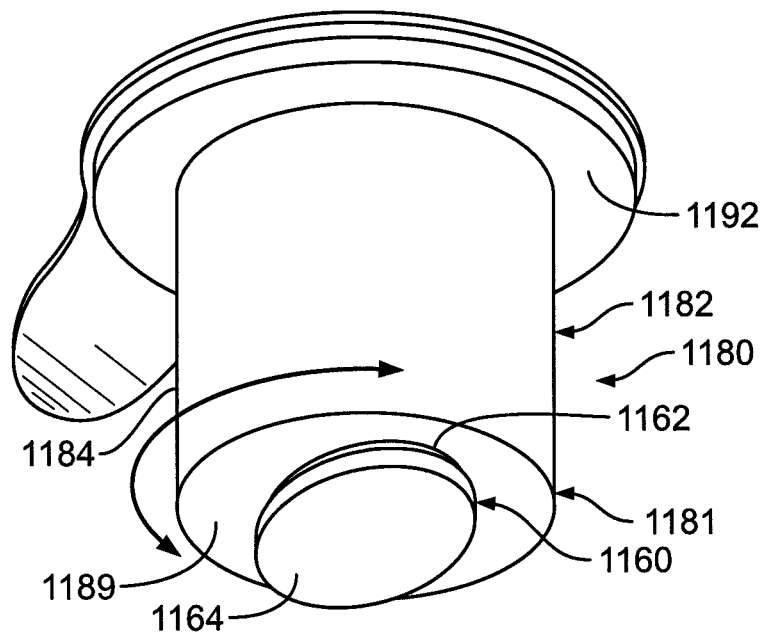
FIG. 69 is a perspective view of an antiseptic cap holder assembly.
Figure 70:
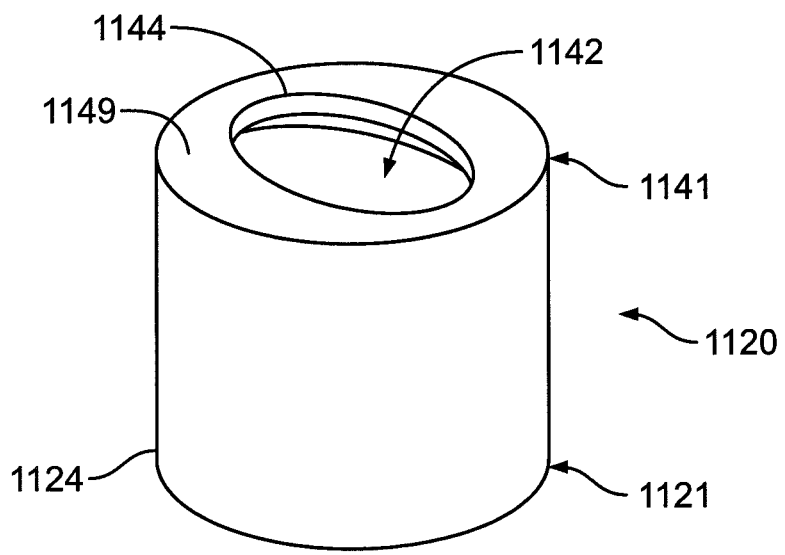
FIG. 70 is a perspective view of a tip cap.

FIG. 68 is a side view showing a syringe with an antiseptic cap assembly attached to a tip cap disposed thereon generally indicated at 1010. The syringe 1012 includes a barrel 1014 having a forward end 1016. The forward end 1016 of the syringe 1012 is configured with an access point connection for attachment to an access point to deliver a fluid or medicament to a patient. Prior to use, the syringe access point connection is covered with a tip cap 1020. The tip cap 1020 has a proximal end 1021 that is attached to the access point connection of the syringe 1012. The tip cap 1020 also has a distal end 1041 comprising a snap-fit flange 1042. A cap holder assembly 1080 carries an antiseptic cap 1082 and includes a snap-fit chamber 1084 located at a bottom thereof. The snap-fit chamber 1084 is configured to mate with the snap-fit flange 1042. In use, the antiseptic cap 1082 could be applied while the antiseptic cap holder assembly 1080 is attached to the tip cap 1020 or the antiseptic cap holder assembly 1080 can be removed from the tip cap 1020 and used separately.

Referring to FIGS. 69-72, a tip cap and cap holder assembly combination are generally indicated at 1110. The tip cap 1120 has a proximal end 1121 that is attached to the access point connection of a syringe and a distal end 1141 comprising a distal end wall 1149 having a distal locking chamber 1142 disposed therein. A cap holder assembly 1180 has a proximal end 1181. The proximal end 1181 of the cap holder assembly 1180 includes a locking protrusion 1160 comprising a stem 1162 and a locking flange 1164, discussed in greater detail below.

Figure 71:
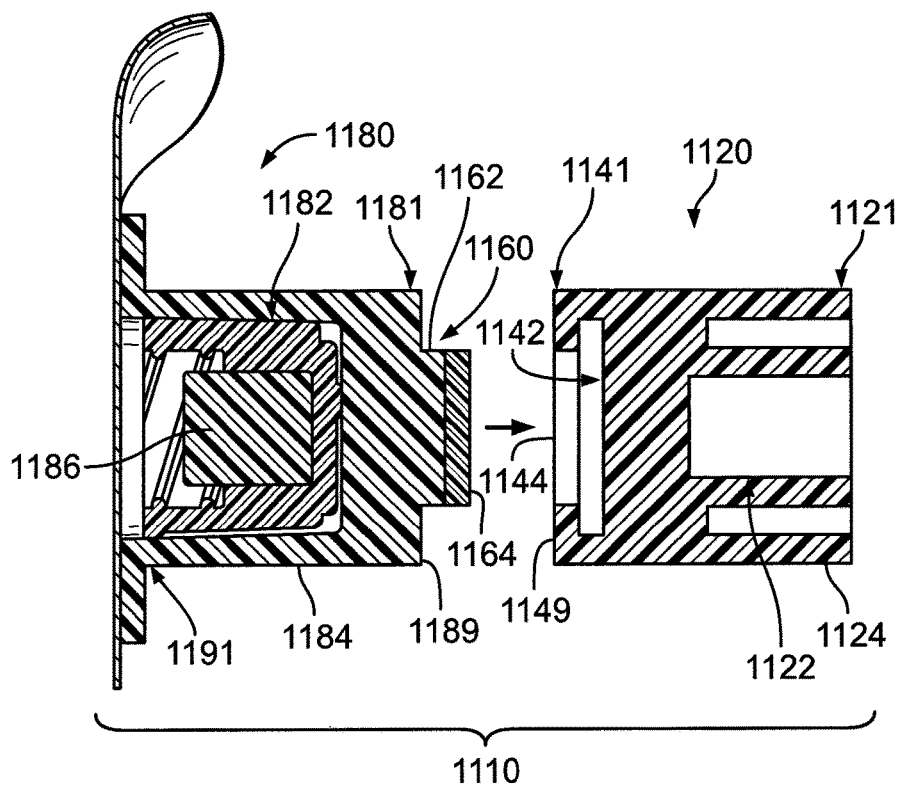
FIG. 71 is a cross-sectional view of the antiseptic cap holder assembly of FIG. 69 and the tip cap of FIG. 70 disengaged and unlocked.
Figure 72:
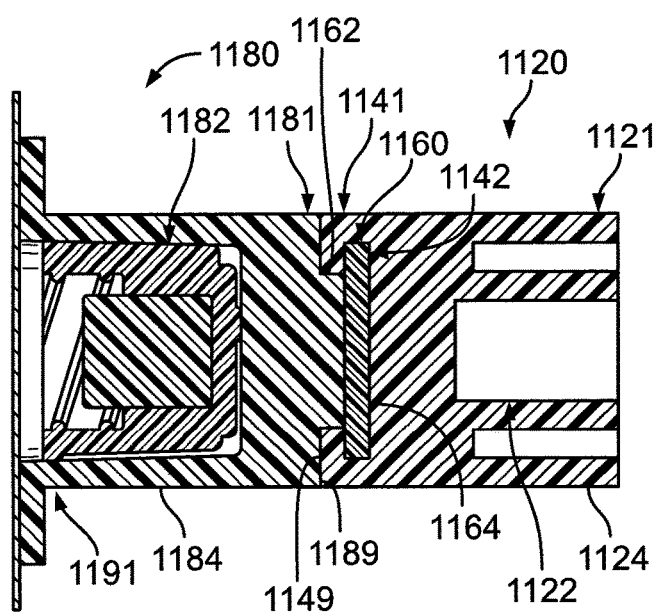
FIG. 72 is a cross-sectional view of the antiseptic cap holder assembly of FIG. 69 and the tip cap of FIG. 70 engaged and locked.

Referring to FIGS. 71 and 72, it can be seen that the tip cap 1120 includes a proximal chamber 1122 and the distal locking chamber 1142 positioned within a cylindrical or tapered side wall 1124. The side wall 1124 could include ribs or gripping surfaces to facilitate handling thereof. The proximal chamber 1122 is configured for attachment to an access point connection on a forward end of a barrel of a syringe as is known. The configuration of the proximal chamber 1122 can be varied in accordance with what is known in the art.

The distal locking chamber 1142 comprises a circular chamber having an oblong or oval entrance 1154. The locking flange 1164 on the locking protrusion 1160 of the cap holder assembly 1180 has an oblong or oval shape configured to match the shape of the entrance 1154 of the distal locking chamber 1142. The stem 1162 preferably has a wall thickness that matches the distal end wall 1149 of the tip cap 1120. This configuration allows the locking flange 1164 to be inserted into the distal locking chamber 1142. After the locking flange 1164 is inserted into the distal locking chamber 1142, the cap holder assembly 1180 can be rotated, such as by 90 degrees, such that the locking flange 1164 rotates in the circular distal locking chamber 1142, to retain the locking flange 1164 in the chamber 1142 such that the locking flange 1164 cannot be pulled therefrom because of the oblong or oval entrance 1154. In such an arrangement, the cap holder assembly 1180 is locked to the tip cap 1120 until it is rotated an additional 90 degrees. Importantly, other locking flange 1164 and entrance or cut out 1154 geometries are contemplated, and they are not limited to solely oblong or oval geometries. Instead, the locking flange 1164 and the entrance or cut out 1154 may be matching asymmetrical designs, rectangular, triangular, or any other geometric arrangement. In use, the antiseptic cap 1182 could be applied while the antiseptic cap holder assembly 1180 is attached to the tip cap 1120 or the antiseptic cap holder assembly 1180 can be removed from the tip cap 1120 and used separately.

Figure 73:
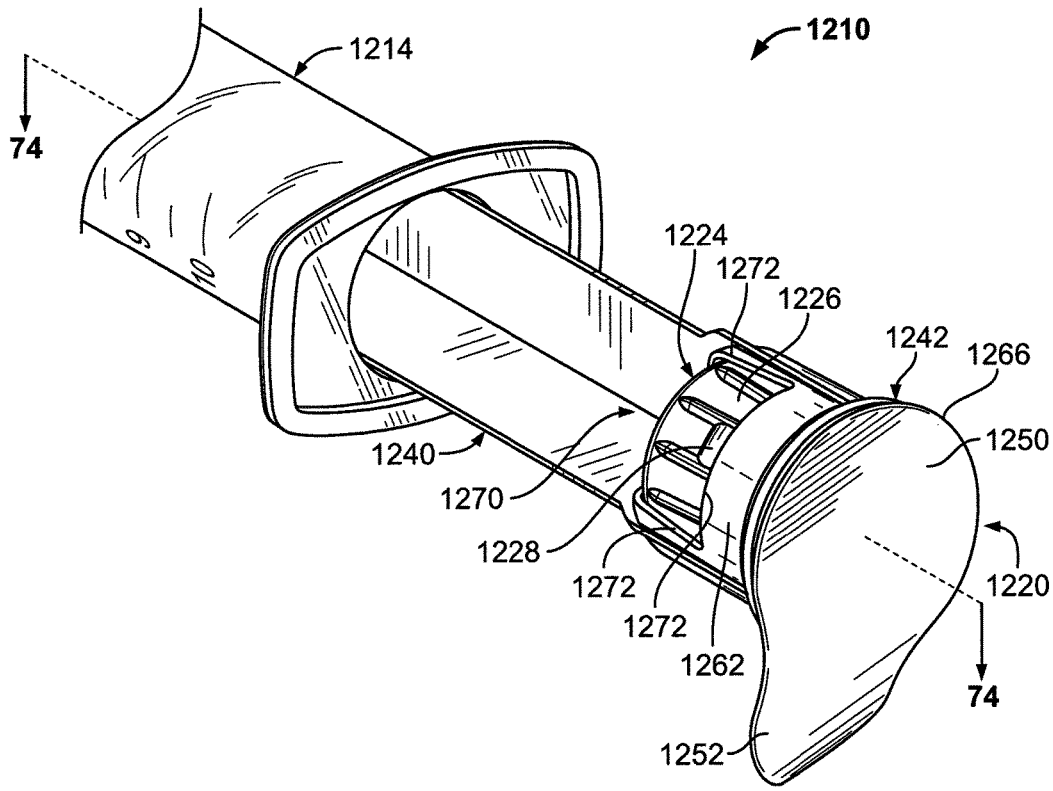
FIG. 73 is a perspective view of a syringe having a plunger with a cap holder assembly that is manually removable from the plunger.
Figure 74:
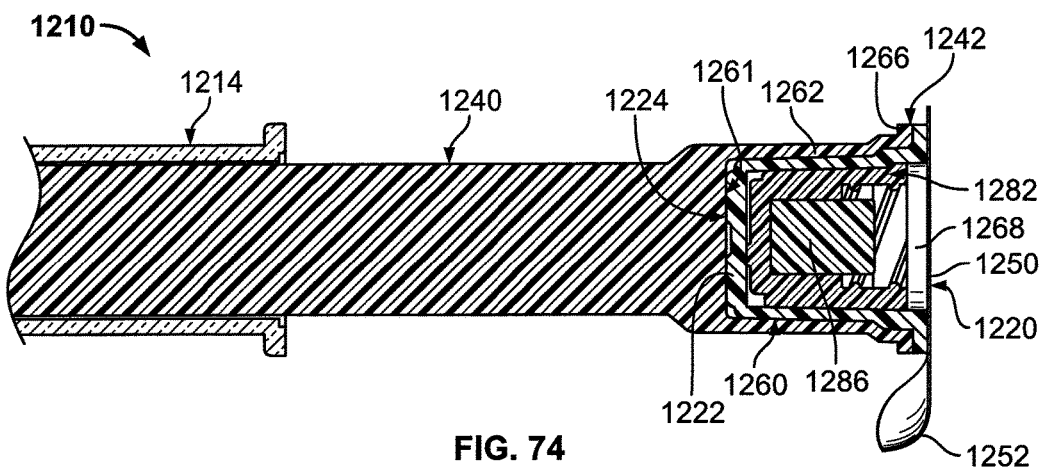
FIG. 74 is a cross-sectional view of the syringe, plunger, and cap holder assembly of FIG. 73.

Referring to FIGS. 73-76, a syringe assembly having a plunger configured for removably receiving an antiseptic cap is shown generally at 1210. As shown in FIGS. 73 and 74, the syringe 1210 has a barrel 1214 and a plunger 1240. The plunger 1240 has a proximal end 1242 that includes a chamber 1260, sized to receive and removably hold a cap holder assembly 1220. Referring to FIG. 74, the chamber 1260 is defined by a bottom wall 1261, and an annular sidewall 1262 that has a peripheral proximal end 1266 that defines an opening 1268 through which the cap holder assembly 1220 can be inserted into the chamber 1260.

The cap holder assembly 1220, as previously discussed herein, comprises a cap holder 1222, an antiseptic cap 1282, a sponge 1286 in some cases, an antiseptic material, and a cover or film 1250. A pull tab 1252 could be provided for facilitating removal of the film 1250 from the cap holder 1222 to provide access to the antiseptic cap 1282. The cap holder 1222 could have a distal end 1224 and one or more bulges 1228 on the outer surface 1226 to secure the cap holder assembly 1220 in the chamber 1260.

The sidewall 1262 of the plunger 1240 includes one or more apertures 1270 defined by edges 1272. The one or more apertures 1270 provide access to the chamber 1260 and facilitate removal of the cap holder assembly 1220 from the plunger 1240 as will be described hereinafter.

Figure 75:
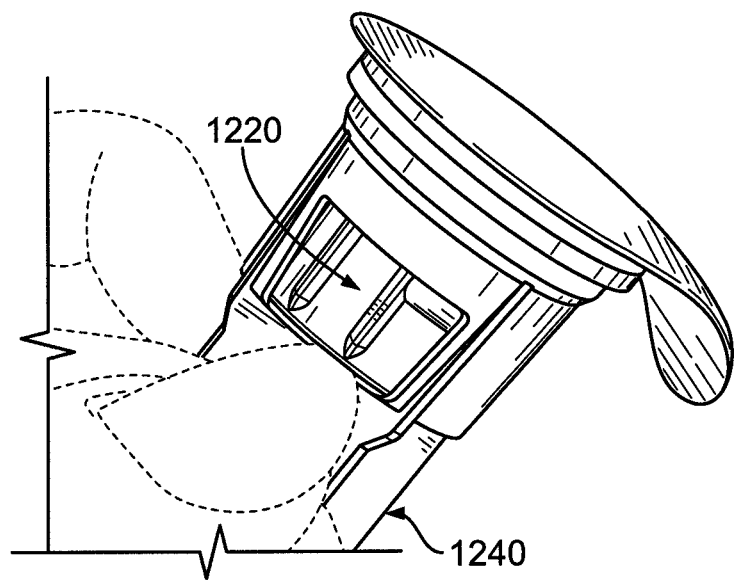
FIGS. 75 and 76 are sequential views, showing the process of manually removing the cap holder assembly from a chamber of the plunger.
Figure 76:
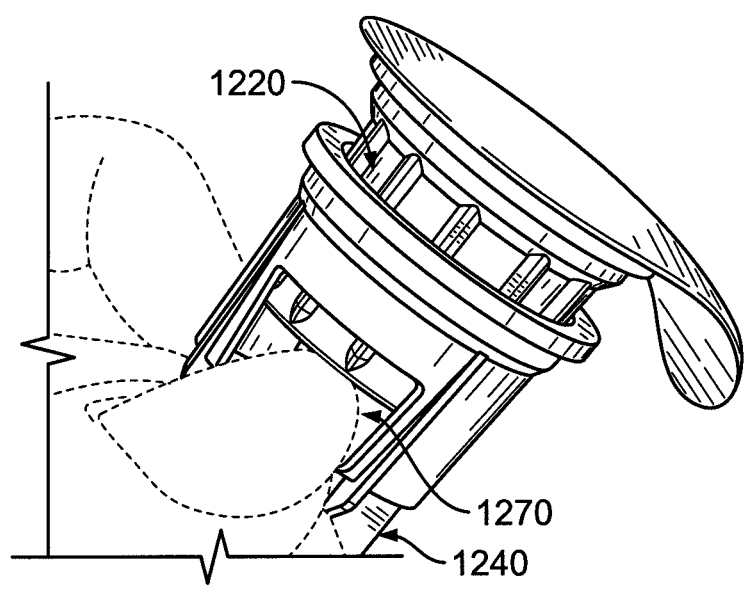
Figure 77:
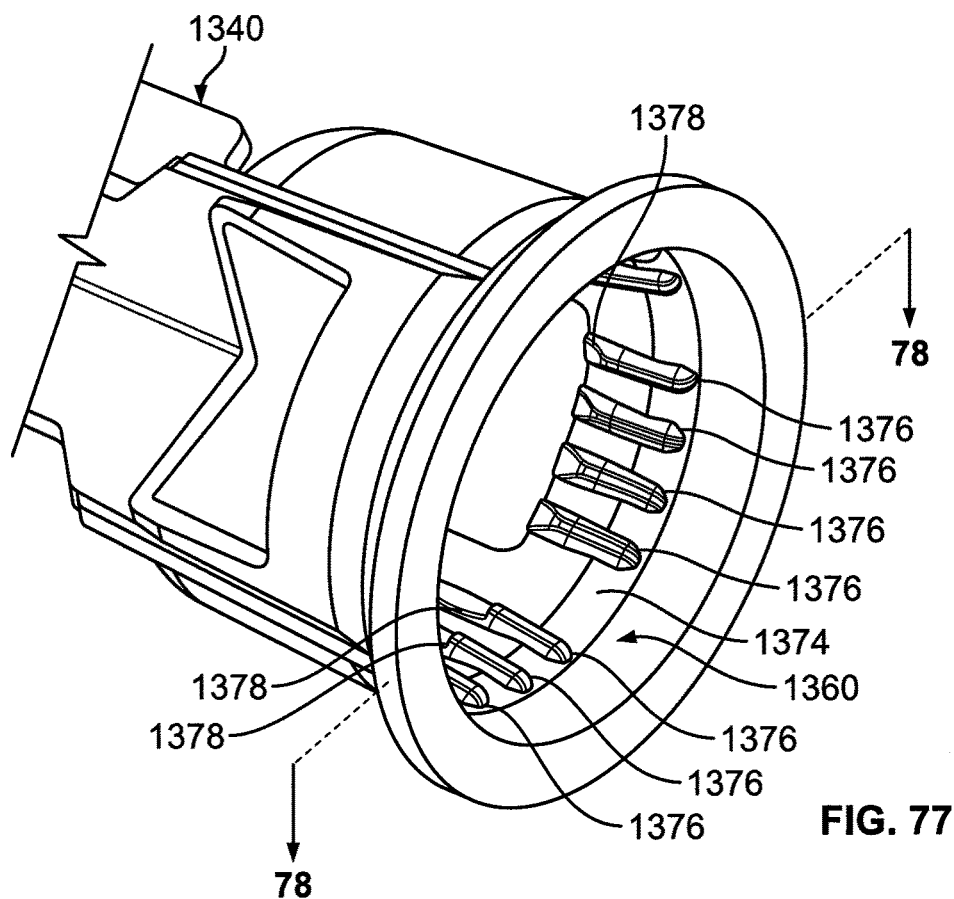
FIG. 77 is a perspective view of another embodiment of a chamber of a plunger with ribs having grooves.
Figure 78:
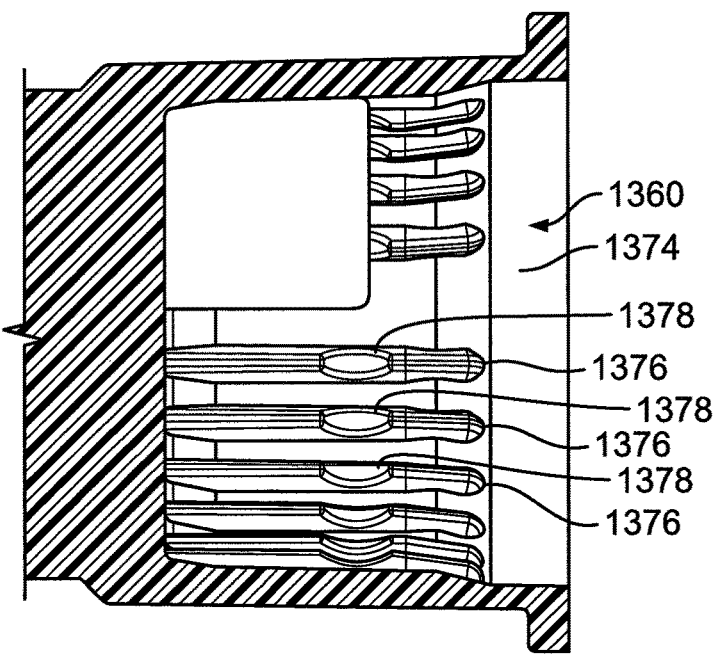
FIG. 78 is a cross-sectional view of the chamber of FIG. 77.
Figure 79:
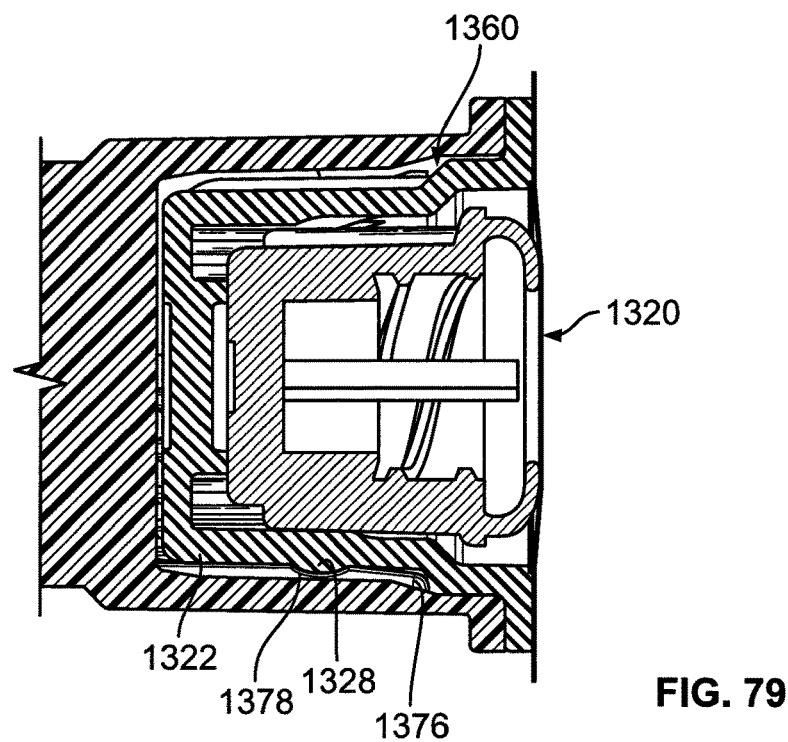
FIG. 79 is a cross-sectional view of a cap holder assembly positioned within the chamber shown in FIG. 78.

The cap holder assembly 1220 can be removed from the plunger 1240 and the process thereof is shown in FIGS. 75 and 76. As shown in FIG. 75, removal of the cap holder assembly 1220 from the plunger 1240 involves placing one's thumb or finger through the one or more apertures 1270 against a lower surface of the the cap holder assembly 1220. As shown in FIG. 76, one thereafter pushes against the cap holder assembly 1220 with a finger or thumb to urge the cap holder assembly 1220 out of the chamber 1260. Ultimately, the cap holder assembly 1220 is ejected from the chamber 1260. In this way, the antiseptic cap 1282 could be conveniently used at a different time than the syringe 1210.

Figure 80:
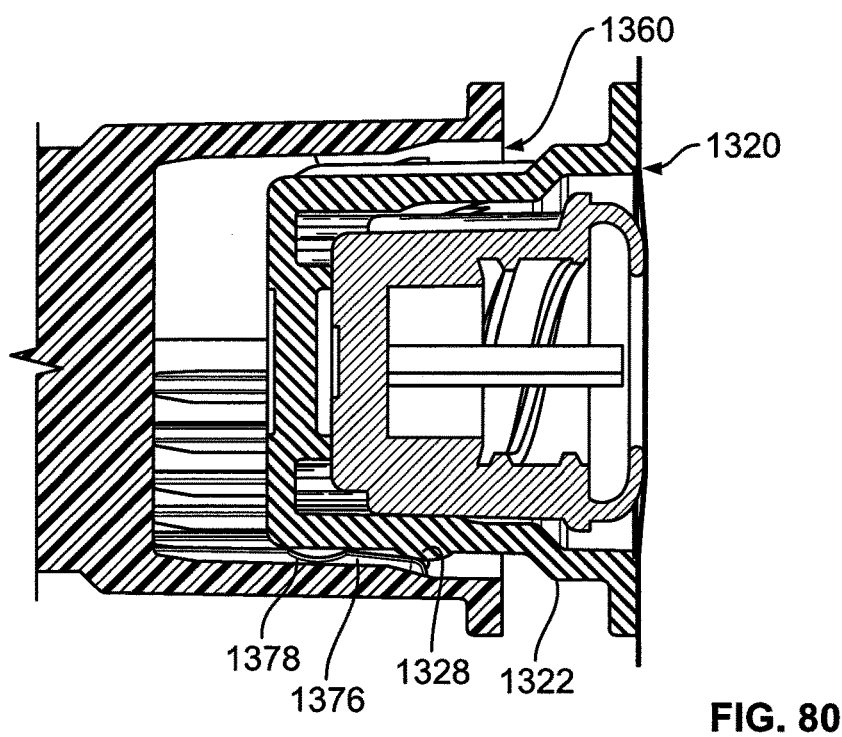
FIG. 80 is a cross-sectional view of a cap holder assembly partially removed from the chamber shown in FIG. 78.

FIGS. 77-80 show another embodiment of a chamber 1360 of a plunger 1340 wherein an interior surface 1374 of the chamber 1360 of the plunger 1340 could have a plurality of circumferentially spaced ribs 1376 that contact the cap holder assembly 1320 to secure the cap holder assembly 1320 in the chamber 1360. As shown in FIGS. 77-80, the ribs 1376 could each contain a first groove 1378 shaped to accept the bulge 1328 of the cap holder 1322 to further secure the cap holder assembly 1320 within the chamber 1360. As such, applying pressure to the cap holder assembly 1320, disengages the bulge 1328 from the groove 1378, as shown in FIG. 80. Further pressure against the cap holder assembly 1320 continues the removal process. The ribs 1376 could also be tapered to facilitate the controlled removal of the cap holder assembly 1320, and prevent the cap holder assembly 1320 from ejecting too rapidly. The ribs 1376 can provide a decreasing amount of resistance against the bulge 1328 of the cap holder 1322 as the cap holder assembly 1320 is urged out of the chamber 1360.

Figure 81:
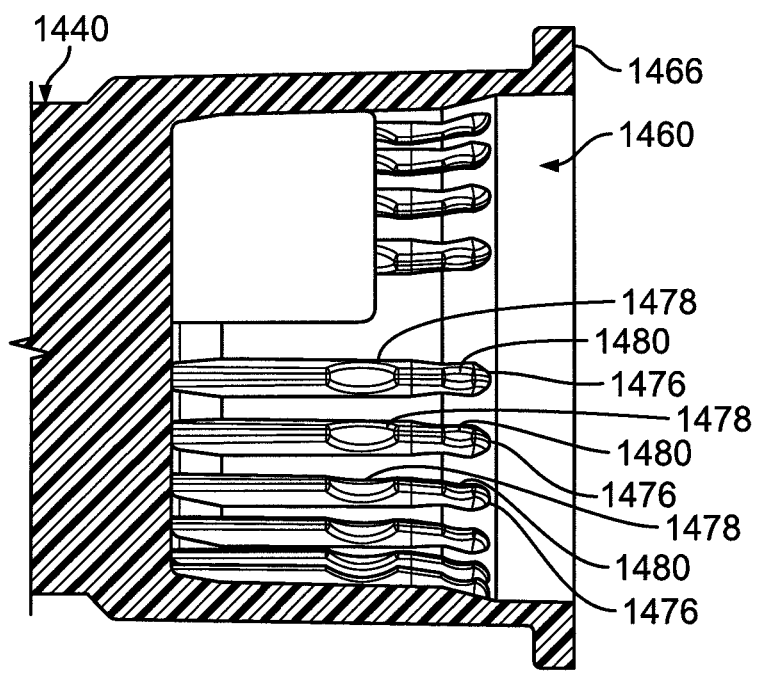
FIG. 81 is a cross-sectional view of another embodiment of a chamber of a plunger with ribs having two sets of grooves.
Figure 82:
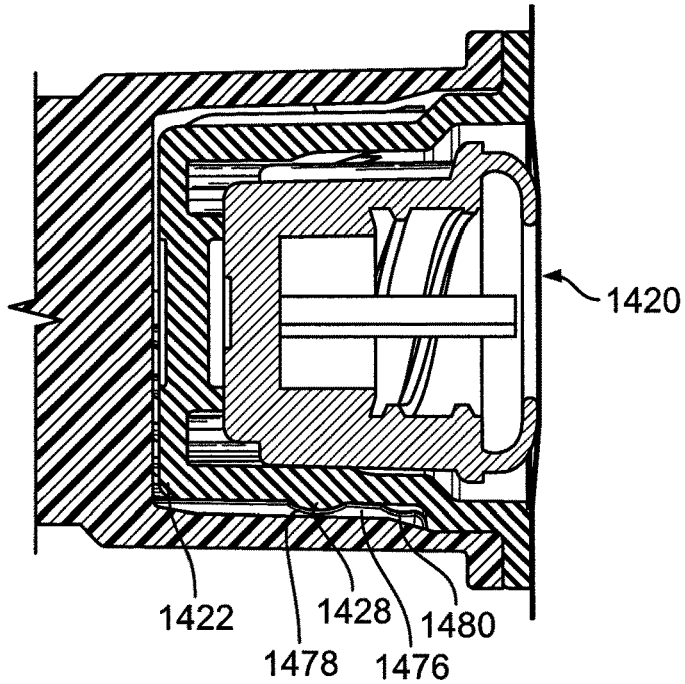
FIG. 82 is a cross-sectional view of a cap holder assembly positioned within the chamber shown in FIG. 81.
Figure 83:
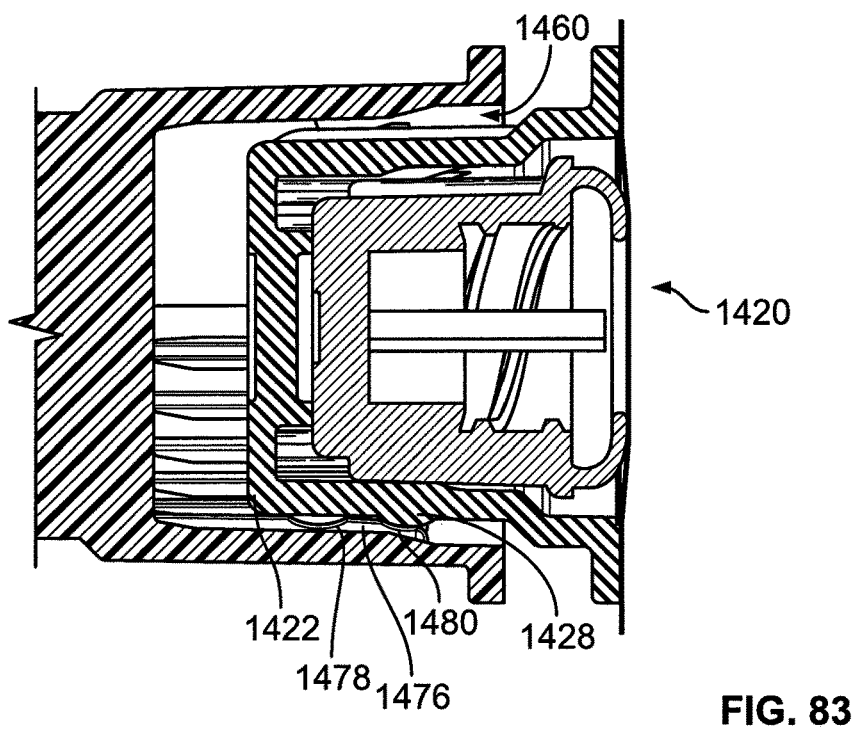
FIG. 83 is a cross-sectional view of a cap holder assembly partially removed from the chamber shown in FIG. 81.

FIGS. 81-83 show another embodiment of a chamber 1460 of a plunger 1440. Like the chamber 1360 of the plunger 1340, the chamber 1460 includes a plurality of ribs 1476. In this embodiment the ribs 1476 of the chamber 1460 could each contain a first groove 1478 and a shallower second groove 1480 closer to the proximal end 1466 of the chamber 1460 and shaped to accept the bulge 1428 of the cap holder 1422 of the cap holder assembly 1420. As shown in FIGS. 82 and 83, as the cap holder assembly 1420 is urged out of the chamber 1460, the bulge 1428 disengages the first groove 1478, and then, after continued pressure, engages the second groove 1480, and then is removed entirely. The second groove 1480 facilitates the controlled ejectment of the cap holder assembly 1420 from the chamber 1460 because less force is required to disengage the cap holder assembly 1420 from the second groove 1480 than from the first groove 1478.

Figure 84:
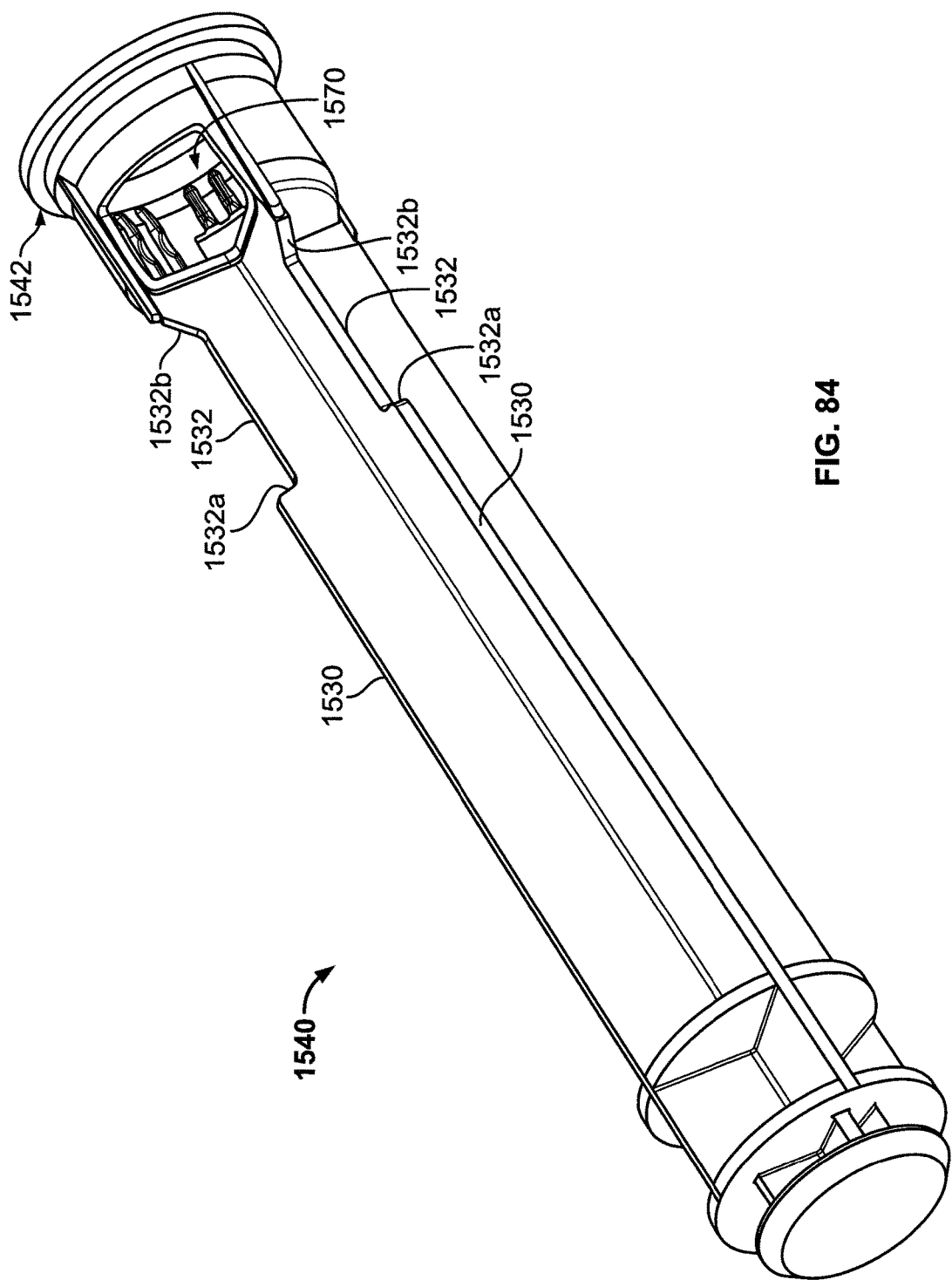
FIG. 84 is a perspective view of another embodiment of a plunger having sidewalls with recessed areas.

FIG. 84 is a perspective view showing a plunger 1540 having four support walls 1530 extending at 90 degree angles with respect to each other from a common point. Towards the proximal end 1542 of the plunger 1540, one or more support walls 1530 has a recessed area 1532 proximal the one or more apertures 1570 to facilitate removal of the cap holder assembly by providing more clearance for a user to place his or her thumb beneath the cap holder assembly as previously shown in FIGS. 75 and 76. The outermost edge of the recessed area 1532 is closer to the common point than the outermost edge of the rest of the sidewall 1530. The recessed area 1523 could be defined by a flat edge 1532*a*, sloped edge 1532*b*, or both, as shown in FIG. 84.

Figure 85:
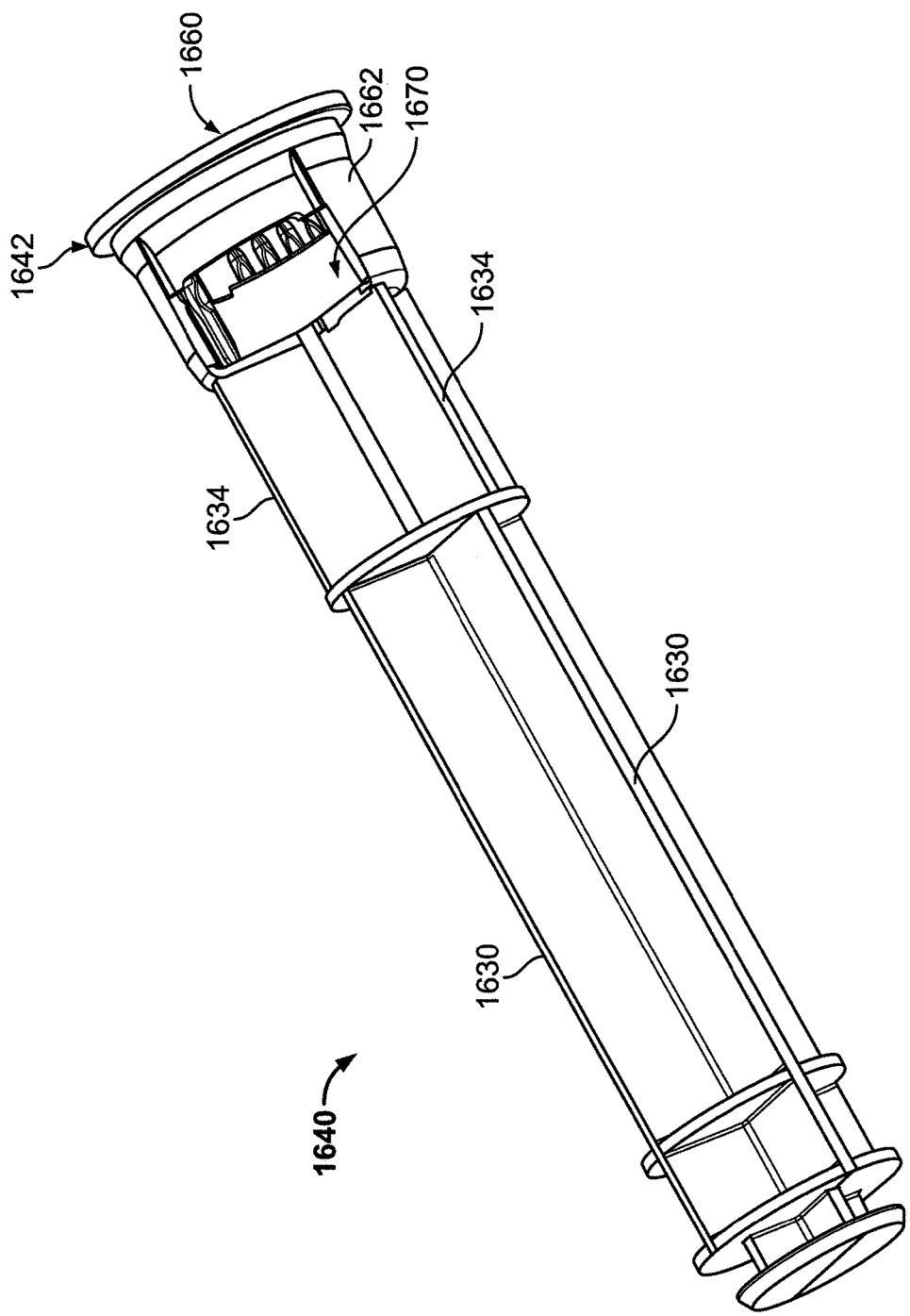
FIG. 85 is a perspective view of another embodiment of a plunger having two or more sidewalls positioned at angles of greater than ninety degrees from each other to provide access to the chamber.

FIG. 85 shows a plunger 1640 having a first set of four support walls 1630 at 90 degrees with respect to each other positioned at a distal portion of the plunger, and a second set of four support walls 1634 at a proximal portion 1642, some of which are spaced apart at a greater angle with respect to each other to allow a wider aperture 1670 in the sidewall 1662 of the chamber 1660. At least two of the support walls flank the aperture of the chamber, which facilitates access to, and removal of, the cap holder assembly by providing more clearance for a user's finger or thumb or other removal tool, if any.

Figure 86:
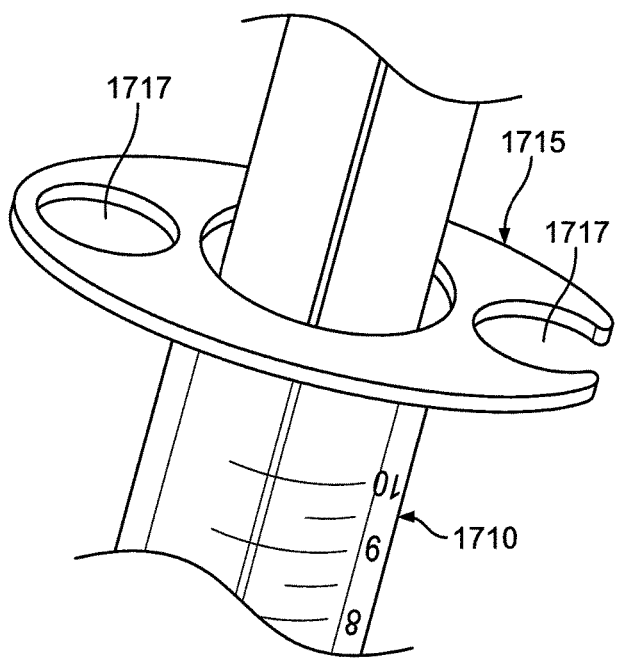
FIG. 86 is a perspective view of another embodiment of a syringe having a flange with receptacles for receiving a cap holder assembly.
Figure 87:
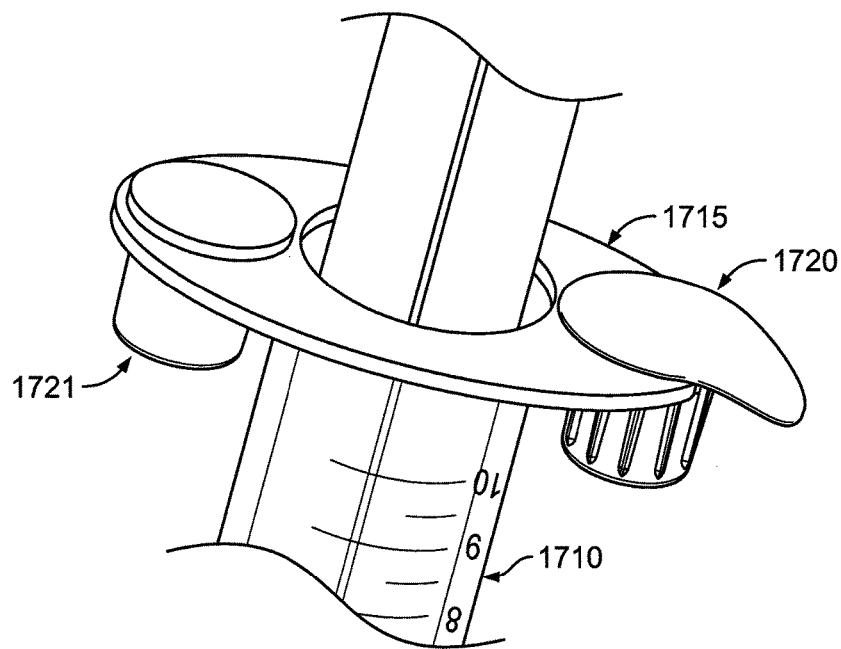
FIG. 87 is a perspective view of the syringe shown in FIG. 86 with a cap holder assembly positioned in a receptacle.

Shown in FIGS. 86 and 87 is a syringe having a gripping flange 1715 with one or more storage receptacles. Specifically, the gripping flange 1715 of the syringe 1710 includes one or more fully or partially bounded apertures 1717 capable of receiving and holding a cap holder assembly 1720 and/or a pre-cleaner 1721. The pre-cleaner 1721 could be used where an access site was not previously disinfected by an antiseptic cap of the present invention, if at all. In such a circumstance, the pre-cleaner 1721 would disinfect the access site, the access site would be used, and then the antiseptic cap would be applied. The cap holder assembly 1720 can be attached within the aperture by a friction fit and the flange about the cap opening can contact the syringe gripping flange 1715, or the cap holder assembly could be otherwise engaged within the aperture.

Figure 89:
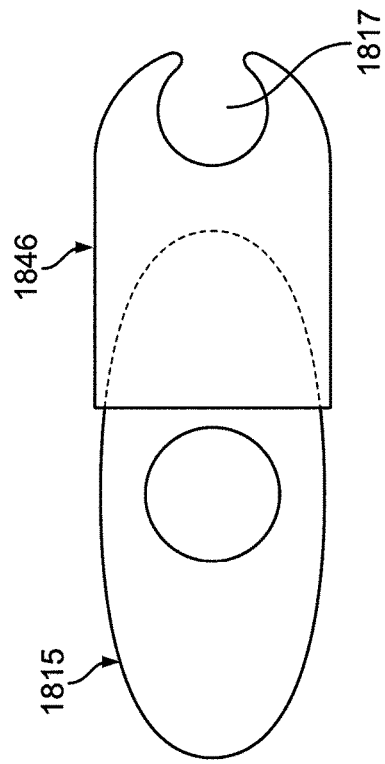
FIG. 89 is a top view of the flange connector panel of FIG. 88 connected to a gripping flange of a syringe.
Figure 91:
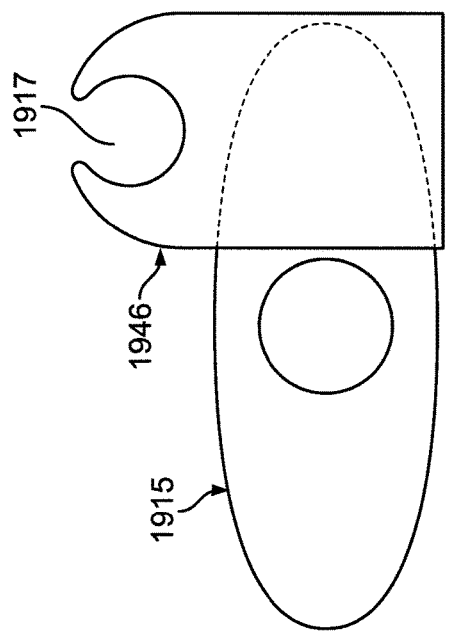
FIG. 91 is a top view of the flange connector panel of FIG. 90 connected to a gripping flange of a syringe.
Figure 88:
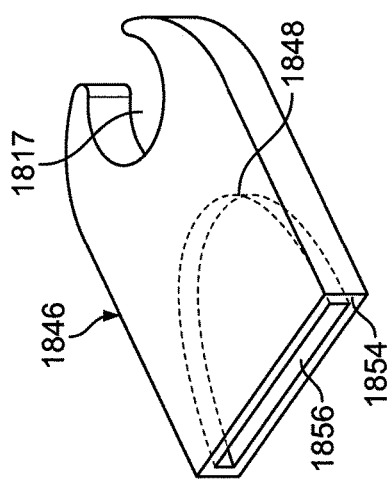
FIG. 88 is a perspective view of a flange connector panel having a cap holder assembly receptacle and a flange slot in a sidewall.
Figure 90:
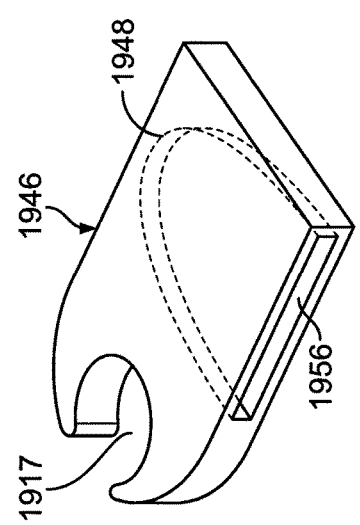
FIG. 90 is a perspective view of another embodiment of a flange connector panel having a flange slot in another sidewall.

Referring to FIGS. 88-95, flange connector panels for receiving a cap holder assembly can be attached to standard gripping flanges of syringes. As shown in FIGS. 88 and 89, a flange connector panel 1846 could have an aperture capable of receiving and holding a cap holder assembly. As shown, the aperture 1817 could have a portion along the outer edge of the flange connector panel 1846 that is unbounded, or the aperture could be completely bounded by the flange connector panel 1846 (not shown). The flange connector panel 1846 includes a slot 1856 in a sidewall 1854 providing access to a sleeve portion 1848. The sidewall 1854 and sleeve portion 1848 are configured to receive a portion of a gripping flange 1815 of a syringe and thereby attach the connector panel 1846 to the syringe. For example, the gripping flange 1815 is curved, and sleeve portion 1848 is similarly curved. This attachment could be maintained by a friction fit, or other means. FIGS. 90 and 91 show a similar device having an aperture 1917, where the slot 1956 providing access to the sleeve portion 1948 to receive a portion of the gripping flange 1915 is on another sidewall of the connector panel 1946.

Figure 92:
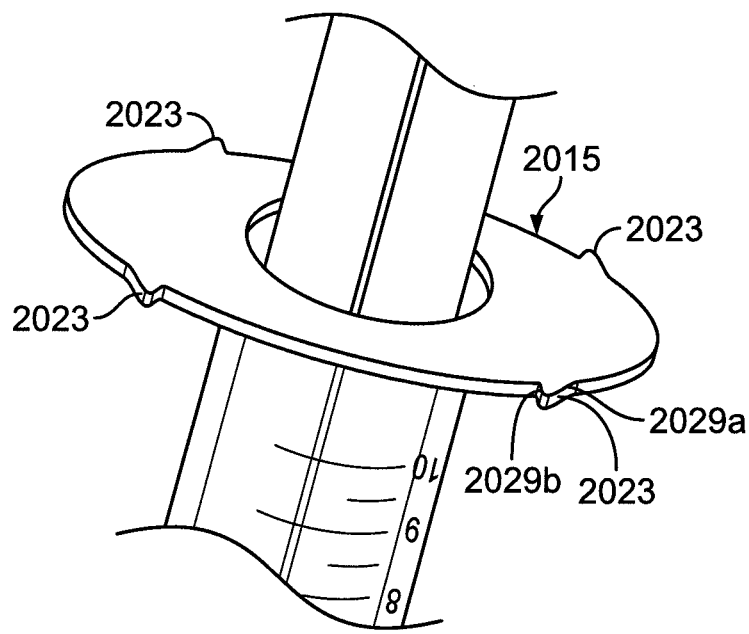
FIG. 92 is a perspective view of another embodiment of a syringe with a gripping flange having engagement teeth.
Figure 93:
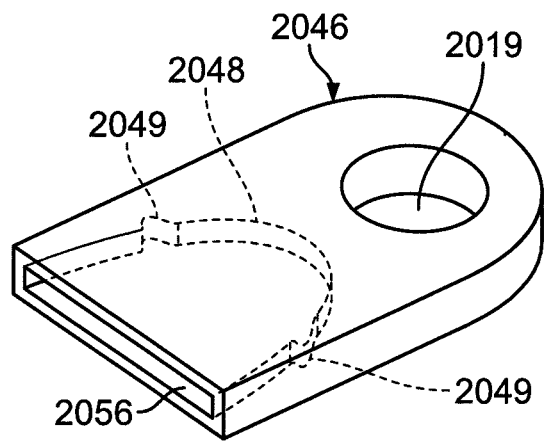
FIG. 93 is a perspective view of a flange connector panel that engages with the gripping flange of FIG. 92.

In another embodiment, shown in FIGS. 92 and 93, a flange connector panel 2046 comprises an aperture 2019 completely bounded by the flange connector panel 2046, and capable of receiving and holding a cap holder assembly. The flange connector panel 2046 includes a slot 2056 providing access to a sleeve portion 2048 having sockets 2049. The sockets 2049 correspond in shape and location to engagement teeth 2023 on a gripping flange 2015 extending from the perimeter of the gripping flange 2015. In this way, when the flange connector panel 2046 is engaged with the gripping flange 2015, the engagement teeth 2023 are received by the sockets 2049 to retain the flange connector panel 2046 on the gripping flange 2015. The teeth 2023 of the gripping flange can have two different sides: a gradually angled side 2029*a*, farthest from the plunger 2040, and a sharply angled side 2029*b*. The sockets 2049 can have corresponding angles. The gradually angled sides 2029*a* of the teeth 2023 and sockets 2049 provide for easy engagement of the connector panel 2046 to the gripping flange 2015, which the sharply angled sides 2029*b* of the teeth 2023 and sockets 2049 prevent disengagement, thereby locking the connector panel 2046 to the gripping flange 2015.

Figure 94:
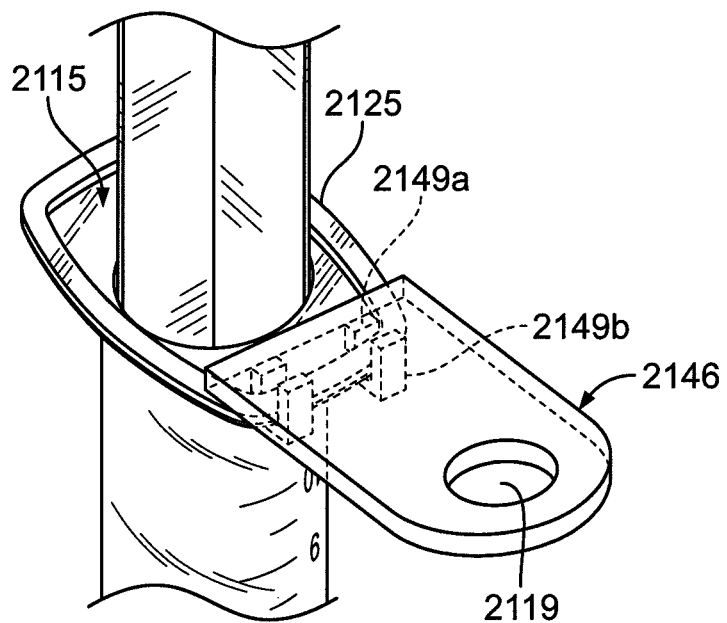
FIG. 94 is a perspective view of another embodiment of a flange connector panel for connection with a gripping flange having a lip.
Figure 95:
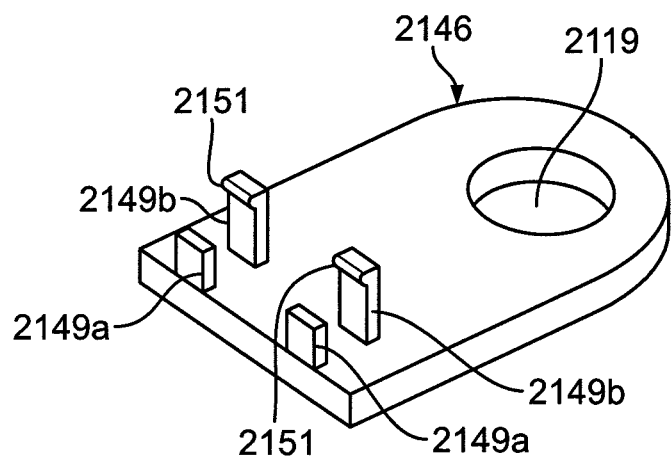
FIG. 95 is a perspective view of a flange connector panel that attaches to the gripping flange of FIG. 94.

In a further embodiment, shown in FIGS. 94 and 95, a gripping flange 2115 includes a lip 2125 along its outer perimeter. A flange connector panel 2146 that includes an aperture 2119, a first pair of fingers 2149*a*, and a second pair of fingers 2149*b* extending from the bottom of the connector 2146 and configured to connect to the lip 2125 of the gripping flange 2115. The distance between the first pair of fingers 2149*a* and second pair of fingers 2149*b* could correspond to the width of the lip 2125 of the gripping flange 2115, such that the first and second pair of fingers 2149*a*, 2149*b* bear against the lip 2125 of the gripping flange 2115. The first pair of fingers 2149*a* could contact the top surface of the gripping flange 2125. The second pair of fingers 2149*b* could be longer than the first pair of fingers 2149*a* and comprise flanges 2151 configured to extend down and contact the bottom surface of the gripping flange 2115. Additionally, as shown, the four fingers 2149*a*, 2149*b* are in a rectangular formation. However, the fingers could be of varying numbers, sizes (e.g., length or width), and/or formations, such as two fingers, six fingers, or a trapezoidal formation.

FIGS. 96 and 97 show a cap holder assembly 2220 connected to the proximal end 2242 of plunger 2240 by a frangible attachment 2236. The frangible attachment 2236 can be made of plastic, and a user can remove the cap holder assembly 2220 from the plunger 2240 by breaking the frangible attachment 2236, such as by bending or twisting. In this way, the cap holder assembly 2220 could be conveniently used at a different time than the syringe 2210. The cap holder 2222 could have an annular protrusion 2238 extending from its distal end 2224 and encircling the frangible attachment 2236 to protect a user from contact and potential injury from the frangible attachment 2236 after breaking the frangible attachment 2236.

Figure 98:
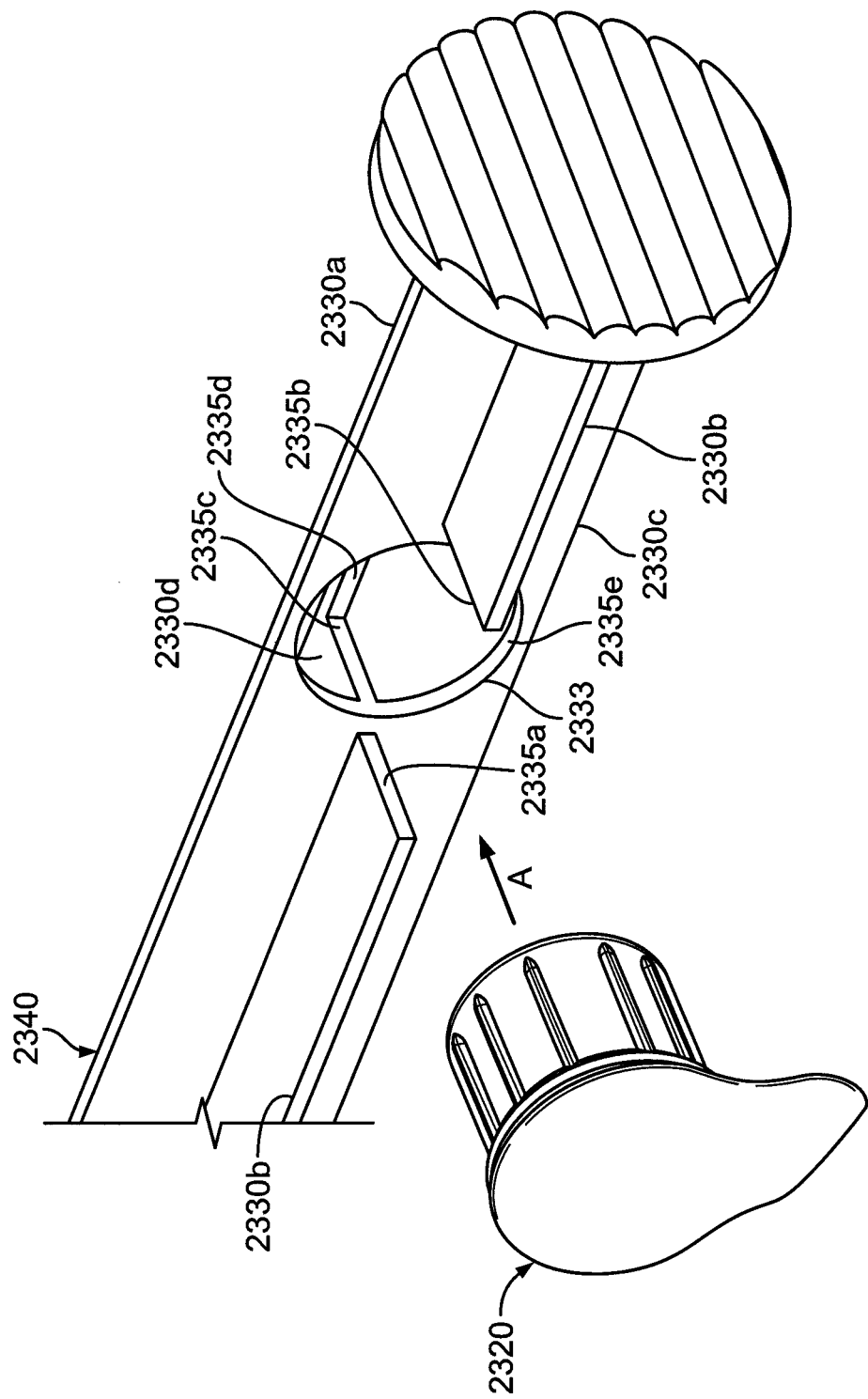
FIG. 98 is an exploded view of a plunger having a transverse opening to receive a cap holder assembly.

FIG. 98 is a perspective view of a plunger 2340 having a receptacle 2333 extending transverse to the plunger 2340. As in previous embodiments, the plunger 2340 has four support walls 2330*a*, 2330*b*, 2330*c*, and 2330*d* extending at 90 degree angles with respect to each other from a common point. One support wall 2330*b* has a discontinuance defined by end walls 2335*a* and 2335*b*. The support wall 2330*d* on the opposite sides has an internal recess defined by distal end wall 2335*c*, lateral end wall 2335*d*, and proximal end wall (not shown). Transverse support walls 2330*a* and 2330*c* have an inner circular wall 2335*e* forming an aperture that extends through walls 2330*a* and 2330*c* between the discontinuance in wall 2330*b* and the recess in wall 2330*d*, creating a receptacle in the plunger. The receptacle is shaped to receive a cap holder assembly 2320. Arrow A illustrates the path of insertion of the cap holder assembly 2320 into the receptacle in the plunger. As shown, the receptacle is circular, but the receptacle could be a variety of shapes. The lateral end wall 2335*d* of the cutout provides structure and rigidity and prevents over insertion of the cap holder assembly 2320. The cap holder assembly 2320 can be retained in the plunger 2340 by a friction fit, or other means.

Figure 100:
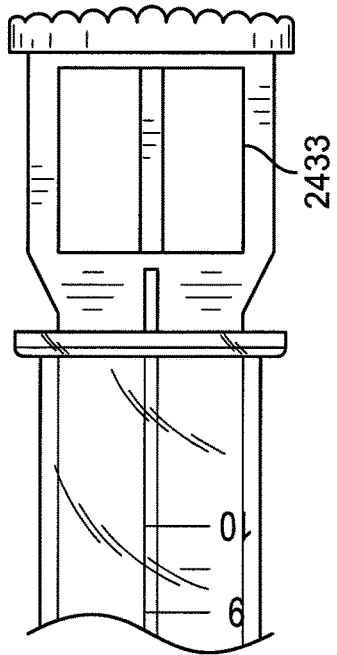
FIG. 100 is a front view of the plunger of FIG. 99.
Figure 101:
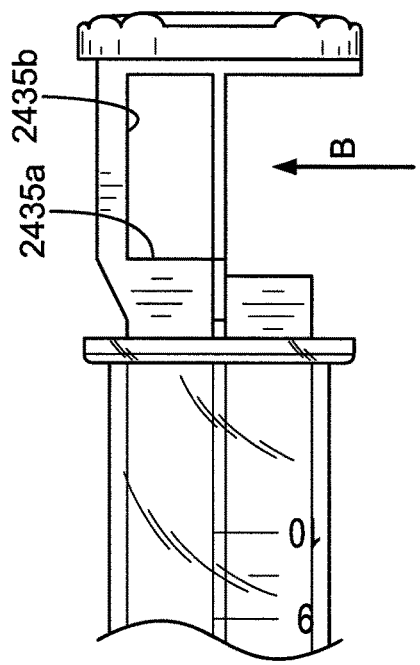
FIG. 101 is a side view of the plunger of FIG. 99.
Figure 99:
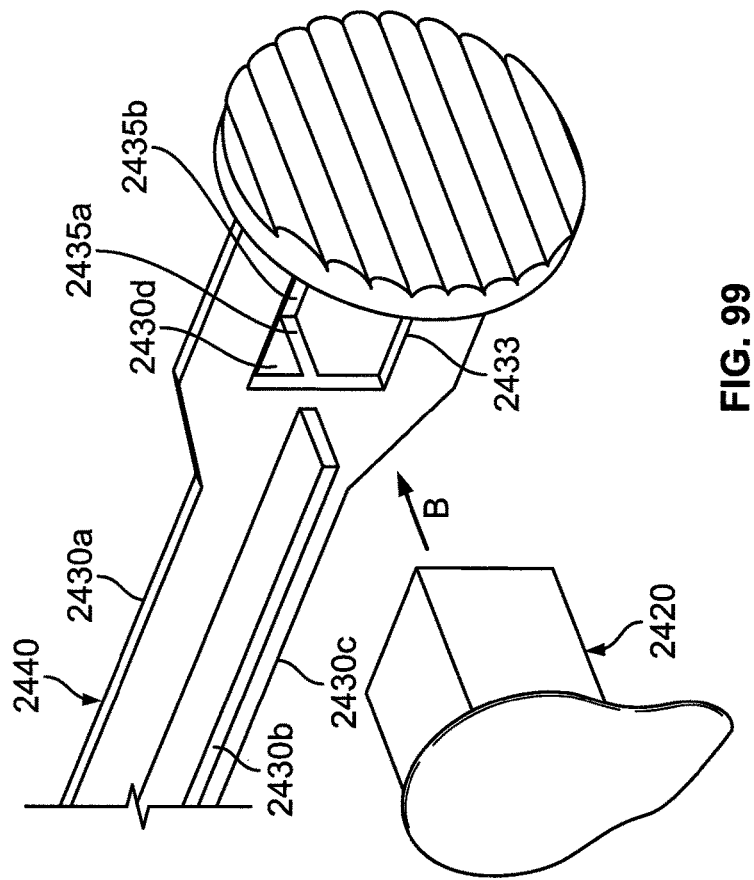
FIG. 99 is an exploded view of another embodiment of a plunger having a transverse opening for receiving a cap holder assembly.
Figure 102:
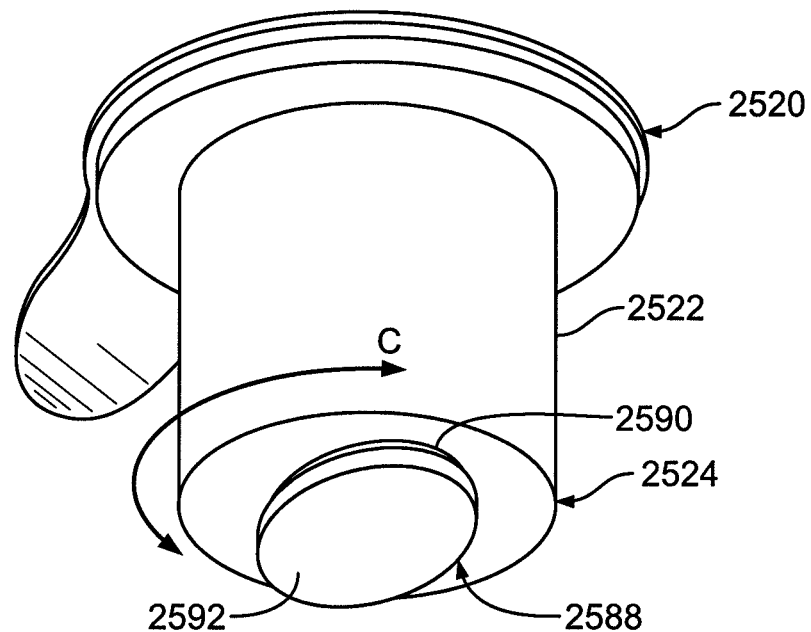
FIG. 102 is a perspective view of another embodiment of a cap holder assembly having a locking flange.
Figure 103:
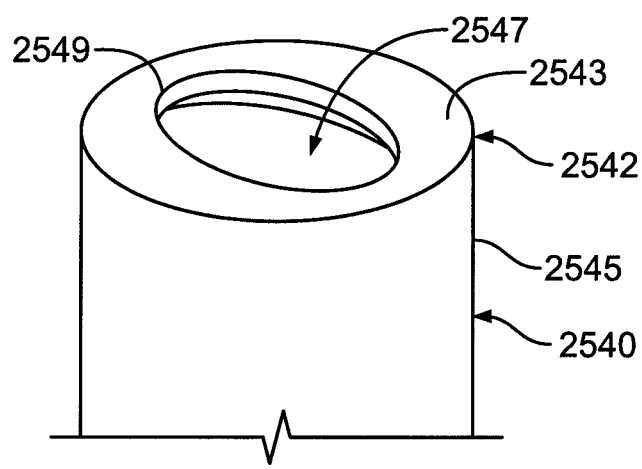
FIG. 103 is a partial perspective view of a plunger having a locking chamber.
Figure 104:
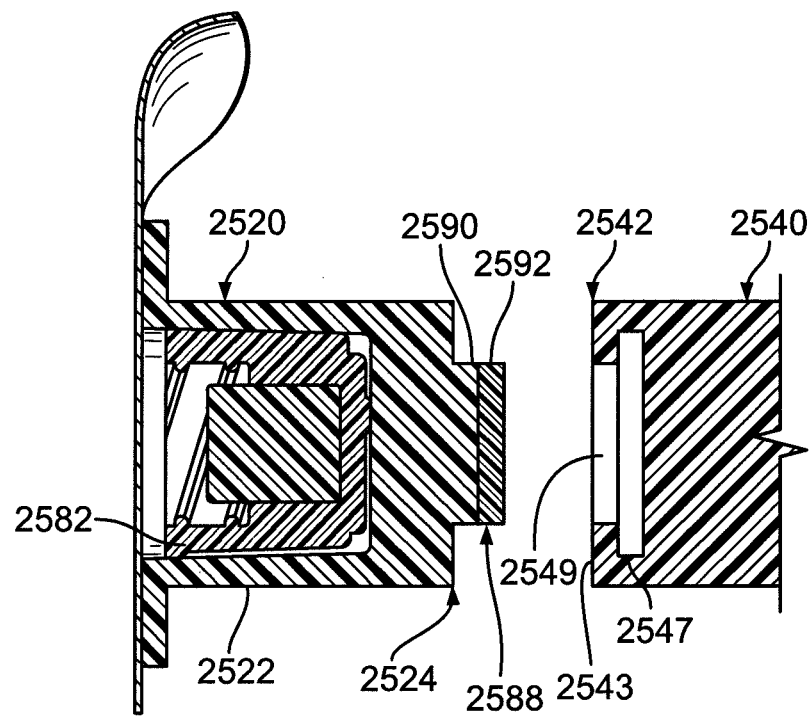
FIG. 104 is a partial cross-sectional view of the cap holder assembly of FIG. 102 and the plunger of FIG. 103 disengaged and unlocked.
Figure 105:
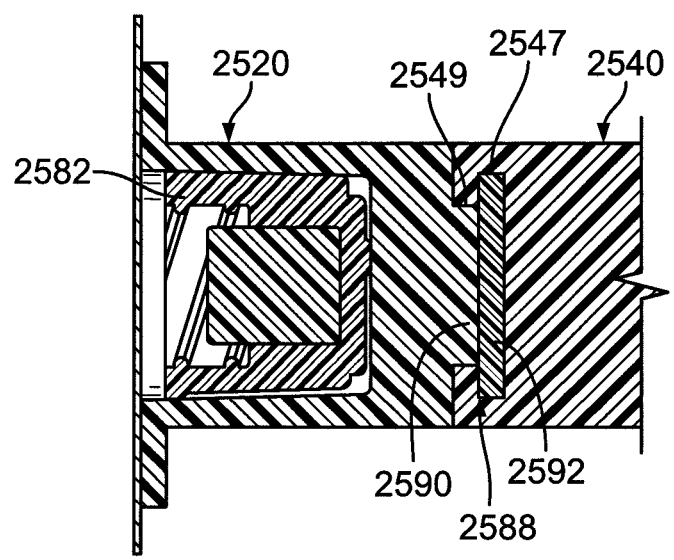
FIG. 105 is a cross-sectional view of the cap holder of the cap holder assembly of FIG. 102 and the plunger of FIG. 103 engaged and locked.

Shown in FIGS. 99-101 is a plunger 2440 having a receptacle 2433 at a proximal end extending transverse to the plunger 2440. The plunger 2440 has four support walls 2430*a*, 2430*b*, 2430*c*, and 2430*d* extending at 90 degree angles with respect to each other from a common point. Support walls 2430*a* and 2430*c* define the receptacle 2433 and could be square or rectangular to accommodate a square or rectangular cap holder of the cap holder assembly 2420. Arrow B illustrates the path of insertion of the plunger cap holder assembly 2420. Support wall 2430*b* has a break providing clearance for engagement of the cap holder assembly 2420 with the receptacle 2433. The support walls 2430 could include a cutout defining sidewalls 2435*a* and a bottom wall 2435*b*. As with the previous embodiment, the sidewalls 2435*a* of the cutout provide clearance for engagement of the cap holder assembly 2420 with the receptacle 2433. The bottom wall 2435*b* of the cutout provides structure and rigidity to the plunger 2440 and prevents over insertion of the cap holder assembly 2420. As with the previous embodiment, the cap holder assembly 2420 can be secured in the receptacle by a friction fit, or other means.

Referring to FIGS. 102-105, another embodiment of the present invention is shown where a proximal end 2542 of a plunger 2540 comprises a proximal end wall 2543 having a proximal locking chamber 2547 disposed therein. The proximal locking chamber 2547 comprises a recessed circular chamber having an oblong or oval entrance 2549. The sidewall 2545 could include ribs or gripping surfaces (not shown) to facilitate handling thereof.

The distal end 2524 of the cap holder 2522 comprises a locking protrusion 2588 having a circular stem 2590 and an oblong or oval locking flange 2592 that matches the shape of the entrance 2549 of the distal locking chamber 2547. The stem 2590 preferably has a wall thickness that matches the proximal end wall 2543 of the plunger 2540. This configuration allows the locking flange 2592 to be aligned with the entrance and inserted into the proximal locking chamber 2547. After the locking flange 2592 is inserted into the proximal locking chamber 2547, the cap holder assembly 2520 can be rotated (e.g., 90 degrees), as illustrated by Arrow C, such that the locking flange 2592 rotates in the circular proximal locking chamber 2547, to retain the locking flange 2592 in the chamber 2547 such that the locking flange 2592 cannot be pulled therefrom because of the oblong or oval entrance 2549. A friction fit could be provided to prevent accidental rotation/disengagement. In such an arrangement the cap holder assembly 2520 could lock to the plunger 2540 until it is rotated an additional 90 degrees with respect to the plunger.

Importantly, other locking flanges 2592, entrances 2549, and cutout geometries are contemplated, and they are not limited to solely oblong or oval geometries. Instead, the locking flange 2592 and the entrance 2549 or cutout may be matching asymmetrical designs, rectangular, triangular, or any other geometric arrangement. In use, the antiseptic cap 2582 could be applied while the cap holder assembly 2520 is attached to the plunger 2540 or the cap holder assembly 2520 can be removed from the plunger 2540 and used separately.

Figure 108:
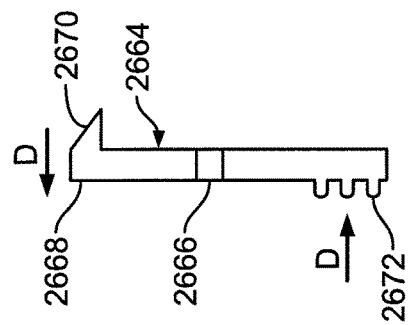
FIG. 108 is a side view of the locking lever of FIGS. 106 and 107.
Figure 107:
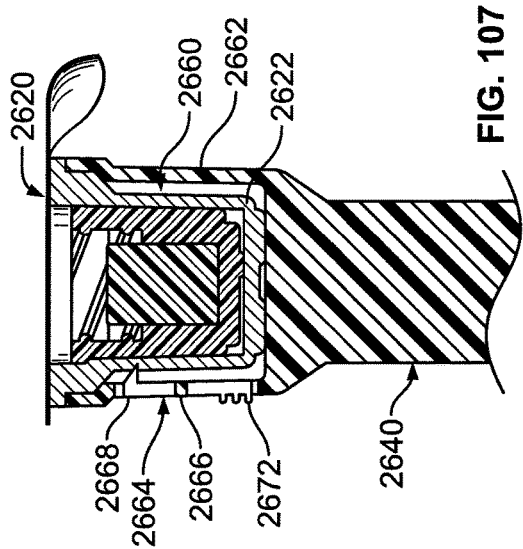
FIG. 107 is a cross-sectional view of the plunger and cap holder assembly of FIG. 106.
Figure 106:
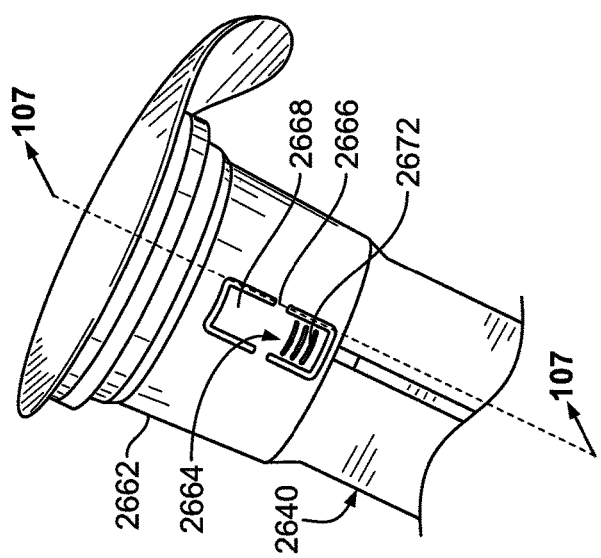
FIG. 106 is a perspective view of another embodiment of a plunger having a locking lever and a cap holder assembly disposed therein.

Another embodiment of the present invention is shown in FIGS. 106-108. A sidewall 2662 of a chamber 2660 of a plunger 2640 comprises a locking lever 2664 having a proximal end 2668 and a distal end 2672, and is connected to the sidewall 2662 by a living hinge 2666, which acts as a fulcrum. The proximal end 2668 comprises a locking protrusion 2670 that engages a groove in the cap holder 2622 of the cap holder assembly 2620, thus locking it when the cap holder 2622 is secured within the chamber 2660 of the plunger 2640. By pushing on the distal end 2672 of the locking lever 2664, the proximal end 2668 rotates about the living hinge 2666, illustrated by lines D, causing the locking protrusion 2670 to disengage from the groove in the cap holder 2622, thereby allowing removal of the cap holder assembly 2620 from the chamber 2660.

Figure 110:
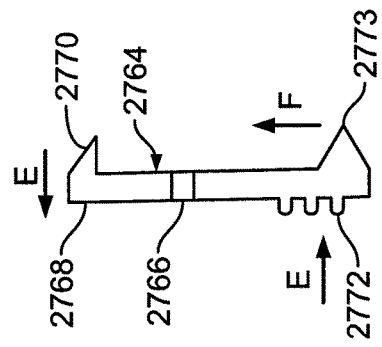
FIG. 110 is a side view of the locking lever of FIG. 109.
Figure 109:
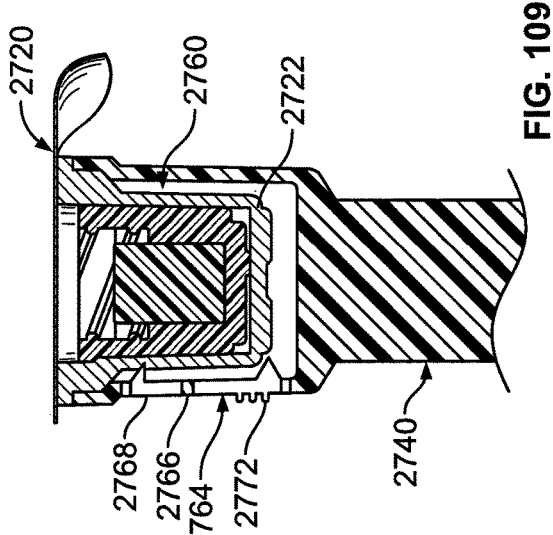
FIG. 109 is a cross-sectional view of another embodiment of the plunger and cap holder assembly that includes a locking lever with a toe.

Moreover, shown in FIGS. 109 and 110, the distal end 2772 of the locking lever 2764 could have a toe 2773 to facilitate removal of the cap holder assembly 2720 from the chamber 2760 of the plunger 2740. When the distal end 2772 of the locking lever 2764 is pressed and the proximal protrusion 2770 of the proximal end 2768 rotates about the living hinge 2766, illustrated by lines E, and disengages from the cap holder 2722, the toe 2773 pushes against the cap holder assembly 2720 and the shape of the toe 2773 urges the cap holder assembly 2720 out of the chamber 2760, illustrated by line F.

Referring to FIG. 111, another embodiment of the present invention is shown where a first adhesive material 2894*a* is fixed to the distal end 2824 of a cap holder assembly 2820 and a second adhesive material 2894*b* is fixed to the proximal end 2842 of the plunger 2840 of the syringe. The two adhesive materials 2894*a*, 2894*b* are removably attachable to one another. The adhesive materials 2894*a*, 2894*b* could be any suitable adhesive or could be another type of material that can form a connection, such as hook and loop fasteners where material 2894*a* could be comprised of hooks, and material 2894*b* could be comprised of loops. In this way, the cap holder assembly 2820 could be repeatedly attached to the plunger 2840. Further, when the cap assembly 2820 is attached to the plunger 2840, the cap may be removed from the cap assembly 2820, without first having to remove the cap holder assembly 2820 from the plunger 2840.

Another embodiment is shown in FIGS. 112 and 113, where a proximal end of the plunger comprises an axially compressible material 2998, such as foam or accordion folded plastic, defining a cavity. As shown in FIG. 112, a cap holder assembly 2920 could be inserted into the cavity, such as by the path illustrated by Arrow G, and secured therein by the frictional radial force of the compressible material 2998 against the outer surface 2926 of the cap holder 2922. As shown in FIG. 113, when the compressible material 2998 is compressed, as illustrated by Arrows H, the cap holder assembly 2920 is easily gripped and removed.

Figure 114:
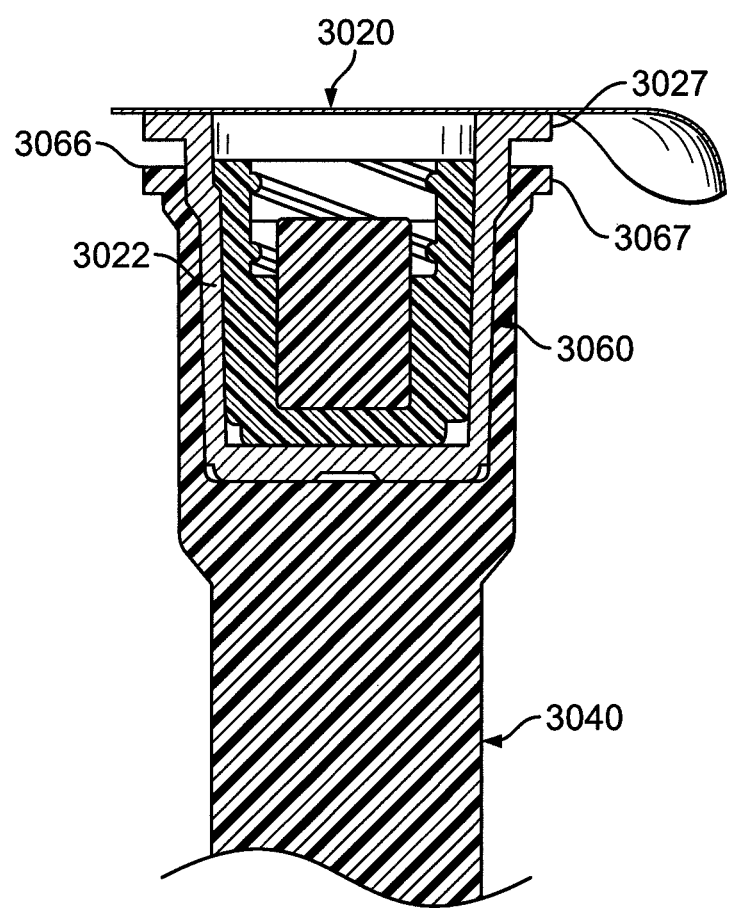
FIG. 114 is a cross-sectional view of a plunger and a cap holder assembly, wherein the cap holder assembly flange is positioned a distance away from the plunger flange.

Referring to FIG. 114, another embodiment of the present invention is shown. A plunger 3040 could have an annular flange 3067 at a peripheral proximal end 3066 of a chamber 3060 and a cap holder 3022 could have an annular flange 3027. When the cap holder assembly 3020 is fully inserted into the chamber 3060 of the plunger 3040 the two flanges 3027, 3067 are spaced apart by a distance. The spaced distance allows a user to grip the flange 3027 of the cap holder 3022, and thus easily remove the cap holder assembly 3020 from the chamber 3060.

Figure 116:
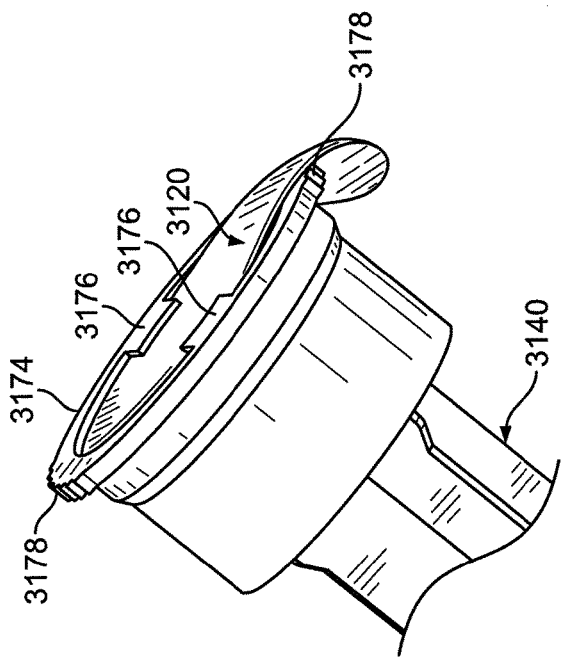
FIG. 116 is a perspective view of the plunger and the cap holder assembly of FIG. 115 disposed in the plunger.
Figure 118:
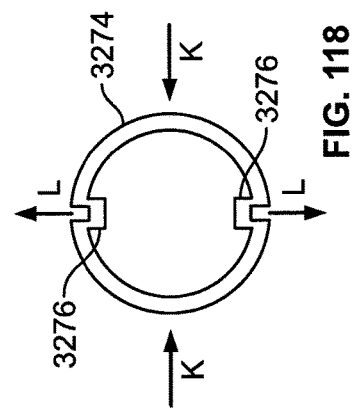
FIG. 118 is a top view of another embodiment of the locking flange of FIGS. 115 and 116.
Figure 115:
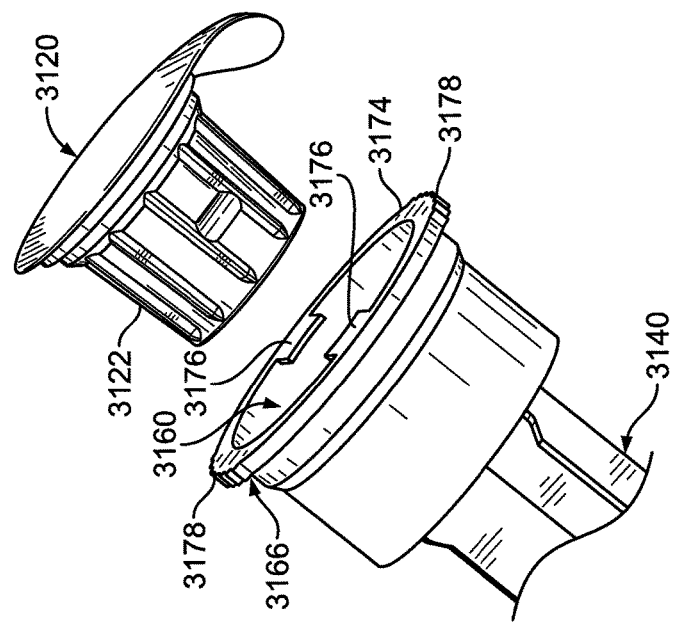
FIG. 115 is an exploded view of a plunger having a locking flange attached thereto and a cap holder assembly.
Figure 117:
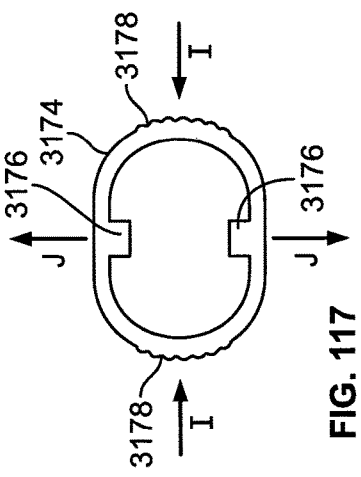
FIG. 117 is a top view of the locking flange of FIGS. 115 and 116.

FIGS. 115-118 show another embodiment of the present invention comprising a radially compressible locking ring 3174 attached to a peripheral proximal end 3166 of a plunger 3140. The locking ring comprises press tabs 3178 and diametrically opposed locking tabs 3176. As shown in FIG. 116, the distance between the locking tabs 3176 is less than the diameter of the cap holder 3122, thus securing the cap holder assembly 3120 in the chamber 3160 of the plunger 3140. When a diametrically opposed force is applied at the press points 3178, as shown by Arrows I, the locking ring 3174 deforms and the locking tabs 3176 separate from each other, shown by Arrows J, sufficient to allow the removal of the cap holder assembly 3120 from the chamber 3160 of the plunger 3140. FIG. 118 shows another embodiment of the locking ring 3274 comprising locking tabs 3276 where the locking ring 3274 is generally circular in shape, and where a force applied, illustrated by lines K, results in the tabs 3276 separating, illustrated by lines L.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. An antiseptic cap assembly for use with an access site comprising:
   a cap comprising:
      a generally cylindrical cap side wall comprising a cap inner surface and a cap external surface, the generally cylindrical cap side wall defining a cap chamber having a cap open end and a cap closed end,
      a cap flange extending radially outwardly from the generally cylindrical cap side wall, and
   an absorbent material within the cap having an antiseptic substance prior to contacting a distal surface of the access site; and
   a housing comprising:
      a housing outer wall and a first housing inner surface defining a first housing chamber having a first housing opening and a first housing chamber closed end, the first housing chamber being configured to receive the cap,
      a housing end wall and a second housing inner surface defining a second housing chamber having a second housing opening and a second housing chamber closed end, the second housing chamber being configured to receive at least a portion of a medical article, and
      a foil seal removably attached to the housing outer wall to maintain the cap in an antiseptic state prior to use.

2. The antiseptic cap of claim 1, wherein the medical article comprises a syringe having a plunger, and wherein the second housing chamber is configured to receive at least a portion of the plunger to attach the antiseptic cap assembly to the syringe.

3. The antiseptic cap of claim 1, wherein the housing further comprises one or more attaching members configured to attach the housing to the medical article.

4. The antiseptic cap of claim 3, wherein the one or more attaching members comprise a plurality of circumferentially spaced tabs extending from the second housing inner surface.

5. The antiseptic cap of claim 1, wherein the cap further comprises a plurality of circumferentially spaced cap ribs on the cap external surface, and wherein the plurality of circumferentially spaced cap ribs extending radially outwardly from and axially along the generally cylindrical cap side wall.

6. The antiseptic cap of claim 5, wherein the plurality of circumferentially spaced cap ribs are proximate to the cap flange and extend towards the cap closed end, and wherein each of the plurality of circumferentially spaced cap ribs have a bottom surface on the generally cylindrical cap side wall and a ridge wall that extends away from the generally cylindrical cap side wall to form an elongated protrusion.

7. The antiseptic cap assembly of claim 5, wherein the plurality of circumferentially spaced cap ribs extend from the cap closed end.

8. The antiseptic cap assembly of claim 7, wherein the plurality of circumferentially spaced cap ribs extend to the cap flange.

9. The antiseptic cap of claim 5, wherein the housing further comprises a plurality of circumferentially spaced housing ribs on the first housing inner surface, and wherein the plurality of circumferentially spaced housing ribs are configured to engage the plurality of circumferentially spaced cap ribs.

10. The antiseptic cap of claim 9, wherein the plurality of circumferentially spaced housing ribs extend from the first housing chamber closed end.

11. The antiseptic cap of claim 1, wherein the housing further comprises a housing flange extending radially outwardly from the housing outer wall.

12. The antiseptic cap assembly of claim 1, wherein the absorbent material is positioned within the cap chamber against the cap closed end.

13. The antiseptic cap assembly of claim 12, wherein the antiseptic substance comprises a liquid, and wherein the liquid is releasably retained within the absorbent material.

14. The antiseptic cap assembly of claim 1, wherein the antiseptic substance comprises a coating on at least a portion of the generally cylindrical cap side wall.

15. The antiseptic cap assembly of claim 1, wherein the cap further comprises a set of threads on the cap inner surface.

16. The antiseptic cap assembly of claim 1, wherein the cap flange is proximate to the cap open end.

* * * * *